United States Patent [19]
Burkholder et al.

[11] Patent Number: 5,977,139
[45] Date of Patent: Nov. 2, 1999

[54] CARBOXYSUBSTITUTED CYCLIC CARBOXAMIDE DERIVATIVES

[75] Inventors: Timothy P. Burkholder, Carmel, Ind.; George D. Maynard, Westbrook; Elizabeth M. Kudlacz, Groton, both of Conn.

[73] Assignee: Hoechst Marion Roussel, Inc., Cincinnati, Ohio

[21] Appl. No.: 08/971,891

[22] Filed: Nov. 17, 1997

Related U.S. Application Data XX
[60] Provisional application No. 60/088,366, Dec. 15, 1996.

[51] Int. Cl.$^6$ .................................................. A01N 43/40
[52] U.S. Cl. .................. 514/316; 514/227.8; 514/235.5; 514/236.2; 514/255; 514/318; 514/326; 544/60; 544/129; 544/364; 546/187; 546/193; 546/208; 546/210
[58] Field of Search ............................ 544/60, 129, 364; 546/187, 193, 208, 210; 514/227.8, 235.5, 236.2, 255, 316, 318, 326

[56] References Cited

U.S. PATENT DOCUMENTS

| | | | |
|---|---|---|---|
| 5,236,921 | 8/1993 | Emonds-Alt | 514/252 |
| 5,317,020 | 5/1994 | Edmonds-Alt | 514/255 |
| 5,340,822 | 8/1994 | Emonds-Alt | 514/316 |
| 5,444,074 | 8/1995 | Baker et al. | 514/326 |
| 5,446,052 | 8/1995 | Emonds-Alt | 514/318 |
| 5,459,270 | 10/1995 | Williams et al. | 546/152 |
| 5,635,510 | 6/1997 | Burkholder et al. | 514/278 |
| 5,648,366 | 7/1997 | Burkholder et al. | 514/326 |

FOREIGN PATENT DOCUMENTS

| | | |
|---|---|---|
| 1490995 | 3/1995 | Australia . |
| 0714891 | 11/1995 | European Pat. Off. . |
| 9426735 | 11/1994 | WIPO . |

OTHER PUBLICATIONS

Barnes, et al., TIPS 11:185–189 (May 1990).
Ichinose, et al., The Lancet 340:1248–1251 (Nov. 21 1992).
Cammack, et al. J. Heterocyclic Chem., 23 73–75 (1986).
Kudlacz, et al., "In Vitro and in vivo characterization of MDL 105,212A, a nonpepetide NK–1/NK–2 tachykinin rectptor Antagonist", J. Pharm. & Exp. Ther., 277 (2) 840–851 (1996).

Burkholder, et al., "Identification and chemical synthesis of MDL 105,212, a non–peptide tachykinin antnagonist with high affinity for NK1 and NK2 receptaors", Bioorganic & Med. Chem. Letters, 6 (8), 951–956 (1996).

Kudlacz, et al., "the NK–1/NK–2 tachykinin receptor antagonist MDL 105,172A inhibits capsaicin–induced respiratory effects in guinea pigs", 8th Inter. Con., Inflammation Res. Assoc., 1996.

Burkholder, et al., "NK1/NK2 receptor antagonists", Tachykinins & their Antagonists Conference, 1996.

Burkholder, et al., "Identification and chemical synthesis of MDL 105212 a non–selective nonpeptide tachykinis receptor antagonist", Tachykinis '95 from Basic Science to Clinical Application Conference, 1995.

Ward, et al., J. Med. Chem. 38, 4985–4992 (1995).

Armour, et al., Bioorganic & Med. Chem Letters 6 (9) 1015–1020 (1996).

Kudlacz, et al., Journal of Autonomic Pharmacology 17 (2) 109–119 (1997).

*Primary Examiner*—Ceila Chang
*Attorney, Agent, or Firm*—David M. Stemerick

[57] ABSTRACT

The present invention relates to novel carboxy substituted cyclic carboxamide derivatives of formula (1),

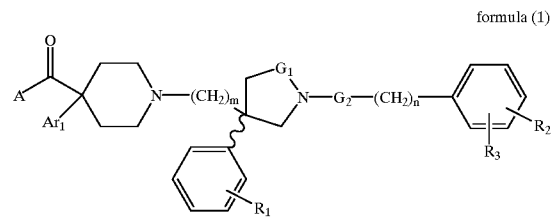

formula (1)

and stereoisomers and pharmaceutically acceptable salts thereof and their use as tachykinin receptor antagonists. Such antagonists are useful in the treatment of tachykinin-mediated diseases and conditions disclosed herein including: asthma, coughs and bronchitis.

64 Claims, No Drawings

CARBOXYSUBSTITUTED CYCLIC CARBOXAMIDE DERIVATIVES

This application claims the benefit of U.S. provisional application No. 60/088,366, filed Dec. 15, 1996.

The present invention relates to novel carboxy substituted cyclic carboxamide derivatives (herein referred to as compounds or compounds of formula (1)), and stereoisomers thereof, and pharmaceutically acceptable salts thereof and their use as tachykinin receptor antagonists. Such antagonists are useful in the treatment of tachykinin-mediated diseases and conditions disclosed herein including: asthma, cough, and bronchitis.

SUMMARY OF THE INVENTION

The present invention relates to novel carboxy substituted cyclic carboxamide derivatives of formula (1):

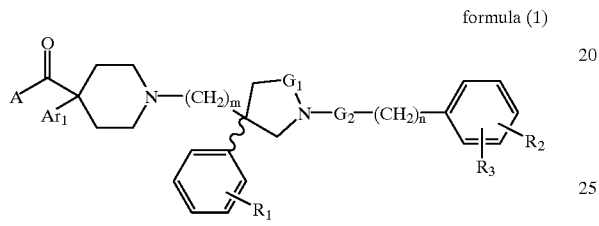

formula (1)

wherein
$G_1$ is $CH_2$ or $C(O)$;
$G_2$ is $CH_2$ or $C(O)$;
m is 2 or 3;
n is 0 or 1;
$R_1$ is from 1 to 3 substituents each independently chosen from the group consisting of hydrogen, halogen, —$CF_3$, $C_1$–$C_6$ alkyl, and $C_1$–$C_6$ alkoxy;
$R_2$ is from 1 to 3 substituents each independently chosen from the group consisting of hydrogen, halogen, cyano, —$CF_3$, $C_1$–$C_6$ alkyl, and $C_1$–$C_6$ alkoxy; $R_3$ is hydrogen or the radical selected from the group consisting of

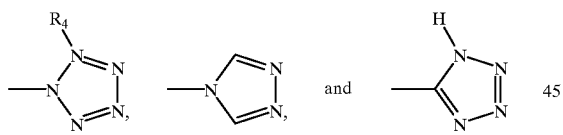

wherein
$R_4$ is selected from the group consisting of hydrogen, $C_1$–C4 alkyl, and —$CF_3$;
$Ar_1$ is a radical selected from the group consisting of

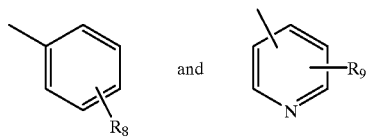

wherein
$R_8$ is from 1 to 3 substituents each independently chosen from the group consisting of hydrogen, halogen, —$CF_3$, $C_1$–$C_6$ alkyl, and $C_1$–$C_6$ alkoxy;
$R_9$ is from 1 to 2 substituents each independently chosen from the group consisting of hydrogen, halogen, $C_1$–$C_6$ alkyl, and $C_1$–$C_6$ alkoxy;

A is a radical selected from the group consisting of

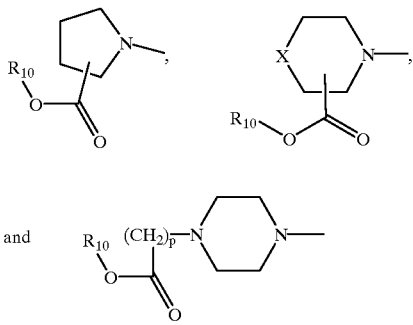

and

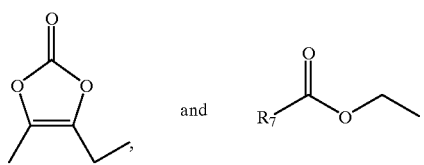

wherein
p is 1, 2, 3, or 4;
X is —O—, —S(O)k— or —$CH_2$—,
wherein k is 0, 1, or 2;
$R_{10}$ is hydrogen, $C_1$–$C_6$ alkyl or a radical selected from the group consisting of

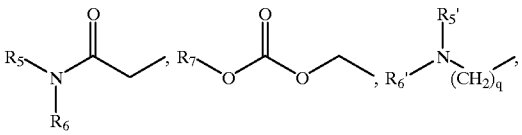

wherein
q is 2 or 3;
$R_5$ is $C_1$–$C_4$ alkyl or —$(CH_2)_2OH$;
$R_6$ is $C_1$–$C_4$ alkyl, —$(CH_2)_2OH$ or —$(CH_2)_2N(CH_3)_2$;
$R_5'$ is $C_1$–$C_4$ alkyl;
$R_6'$ is $C_1$–$C_4$ alkyl;
$R_7$ is $C_1$–$C_6$ alkyl;
provided that when $G_1$ is —C(O)— then $G_2$ is —$CH_2$—;
further provided that when $G_2$ is —C(O)— then $G_1$ is —$CH_2$—;
and stereoisomers, and pharmaceutically acceptable salts thereof.

As is appreciated by one of ordinary skill in the art the compounds of the formula (1) exist as stereoisomers. Any reference in this application to one of the compounds of the formula (1) is meant to encompass either specific stereoisomers or a mixture of stereoisomers. Where indicated, the compounds follow the (+)- and (−)-designation or the Cahn-Ingold-Prelog designation of (R)- and (S)- for the stereochemistry of compounds represented by formula (1) and intermediates thereof. It is specifically recognized that the novel carboxy substituted cyclic carboxamide derivatives of the present invention are asymmetric in the 3-position of the 3,13-disubstituted pyrrolidine and may exist in the (R)- or (S)- configuration or may be a mixture thereof. It is also specifically recognized that the novel substituted cyclic carboxamide derivatives of the present invention may be asymmetric at the point of attachment of the carboxy substituent on the cyclic carboxamide and that, when asymmetric at that point of attachment, the carboxy substituent may be in either the (R)- or (S)-configuration or may be a mixture thereof.

The specific stereoisomers can be prepared by stereospecific synthesis using enantiomerically pure or enantiomerically enriched starting materials. The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are know in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As is readily apparent to those skilled in the art some of the compounds of formula (1) may exists as tautomers. Any reference in this application to one of the tautomers of compounds of the formula (1) is meant to encompass every tautomeric form and mixtures thereof.

As used in this application:

a) the term "halogen" refers to a fluorine atom, chlorine atom, bromine atom, or iodine atom;

b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, sec butyl, t-butyl, pentyl, hexyl, etc;

c) the term "$C_1$–$C_4$ alkyl" refers to a branched or straight chained alkyl radical containing from 1 to 4 carbon atoms, such as methyl, ethyl, n-propyl, isopropyl, n-butyl, isobutyl, sec-butyl, t-butyl, etc;

d) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, sec-butoxy, t-butoxy, pentoxy, hexoxy, etc;

e) the designation "—C(O)—" or "C(O)" refers to a carbonyl group of the formula:

f) the designation "~~~" refers to a bond for which the stereochemistry is not designated;

g) the designation "▬▬" refers to a bond that protrudes forward out of the plane of the page;

h) the designation "∥∥∥" refers to a bond that protrudes backward out of the plane of the page;

i) as used in the preparations and examples the following terms have the indicated meanings; "ng" refers to nanograms; "$\mu$g" refers to micrgrams; "mg" refers to milligrams; "g" refers to grams; "kg" refers to kilograms; "nmole" or "nmol" refers to nanomoles; "mmol" refers to millimoles; "mol" refers to moles; "$\mu$L" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^{20}_D$" refer to specific rotation of the D line of sodium at 20° C. obtained in a 1 decimeter cell; "c" refers to concentration in g/mL; "nM" refers to nanomolar; "$\mu$M"a refers to micromolar; "mM" refers to millimolar; "M" refers to molar; "psi" refers to pounds per square inch; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "AIBN" refers to 2,2'-azobisisobutyronitrile; "$\mu$Ci" refers to microcuries; "i.p." refers to intraperitoneally; "i.v." refers to intravenously; and "DPM" refers to disintegrations per minute;

j) by the designation

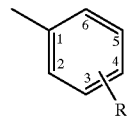

it is understood that the radical is attached at the 1-position and the substituent or substituents represented by R can be attached in any of the 2, 3, 4, 5, or 6 positions;

k) the designation

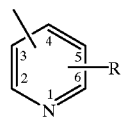

refers to a pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

l) the term "enantiomeric excess" or "ee" refers to the percent by which one enantiomer, E1, is in excess in a mixture of the two enantiomers, E1 plus E2, such that $$\{(E1-E2) \div (E1+E2)\} \times 100\% = ee;$$

m) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (1). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for examples acetic, glycolic, lactic, pyruvic, malonic, succinic, glutaric, fumaric, malic, tartaric, citric, ascorbic, maleic, hydroxymaleicD benzoicD hydroxy-benzoicD phenylacetic, cinnamic, salicyclic, 2-phenoxy-benzoic, p-toluenesulfonic acid; and sulfonic acids such as benzenesulfonic acid, methanesulfonic acid, ethanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

As with any group of structurally related compounds which possesses a particular utility, certain groups and configurations are preferred for the compounds of formula (1) in their end-use application.

Preferred embodiments of formula (1) are given below:

1) Compounds in which m is 2 are preferred;
2) Compounds in which n is 0 are preferred;
3) Compounds in which $G_1$ is —$CH_2$— and $G_2$ is —C(O)— are preferred;
4) Compounds in which m is 2, n is 0, $G_1$ is —$CH_2$—, and $G_2$ is —C(O)— are more preferred;
5) Compounds in which $R_1$ is 3,4-dichloro are preferred;
6) Compounds in which $R_3$ is hydrogen and $R_2$ is 3,4,5-trimethoxy are preferred;
7) For compound in which $R_3$ is not hydrogen, the compounds in which $R_3$ is a radical selected from the group

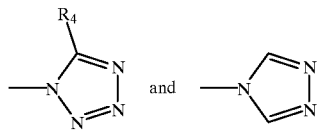

wherein $R_4$ is as defined above, are preferred;
8) For compound in which $R_3$ is not hydrogen, compounds in which $R_3$ is the radical

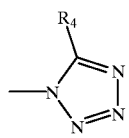

wherein $R_4$ is as defined above, are more preferred;
9) For compound in which $R_3$ is not hydrogen, compounds in which $R_2$ is 2-methoxy and $R_3$ is in the 5-position and is the radical

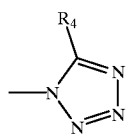

wherein $R_4$ is as defined above, are more preferred;

10) Compounds in which A is a radical selected from the group

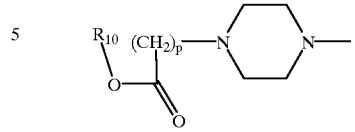

and 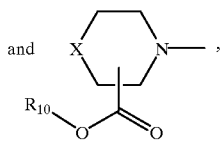

wherein $R_{10}$, p, and X are as defined above, are preferred;
11) Compounds in which A is the radical

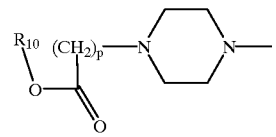

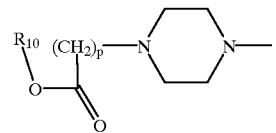

wherein $R_{10}$, p, is as defined above, are more preferred;
12) Compounds in which A is the radical

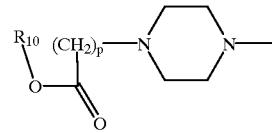

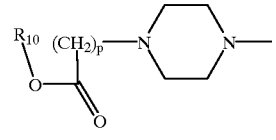

wherein p is 1 and $R_{10}$ is hydrogen or $C_1$–$C_6$ alkyl are even more preferred;
13) Compounds in which A is the radical

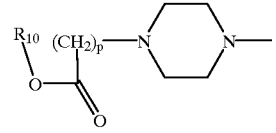

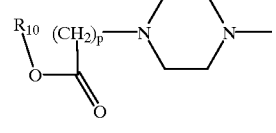

wherein p is 1 and $R_{10}$ is hydrogen or ethyl are most preferred.

It is understood that further preferred embodiments of formula (1) can be selected by requiring one or more of the preferred embodiments 1 through 13 of formula (1) or by reference to examples given herein.

Illustrative of compounds encompassed by the present invention include the following. It is understood that the examples encompass both the (R)-isomers and the (S)-isomers of the compound at both the 3-position of the 3,3-disubstituted pyrrolidine and where applicable, at the point of attachment of the carboxy substituent on the cyclic carboxamide and mixtures thereof. This list is meant to be representative only and is not intended to limit the scope of the invention in any way:

1-(3,4,5-trimethoxybenzoyl)-3-(2-(4-phenyl-4-((4-carboethoxymethylpiperazin-1-yl)carboxamido)piperidin-1-yl)ethyl)-3-phenylpyrrolidine;

1-(3,4,5-trimethoxybenzoyl)-3-(2-(4-phenyl-4-((4-carboethoxymethylpiperazin-1-yl)carboxardido)piperidin-1-yl)ethyl)-3-(3-chlorophenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(3,4-difluorophenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(3-fluorophenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(4-fluorophenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(4-trifluormethylphenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(3,4-dimethylphenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(3,4-dimethoxyphenyl)pyrrolidine;

1-(3,4,5-trimethoxybenzoyl)-3-(2-(4-phenyl-4-((4-carboethoxymethylpiperazin-1-yl)carboxamido)piperidin-1-yl)ethyl)-3-(3-methoxyphenyl)pyrrolidine;

1-benzoyl-3-(2-(4-phenyl-4-((4-carboethoxymethylpiperazin-1-yl)carboxamido)piperidin-1-yl)ethyl)-3-(3,4-dichlorophenyl)pyrrolidine;

1-(4-chlorobenzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(3-(2-propyloxy)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(2-methoxybenzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(3-(1H-tetrazol-1-yl)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(2-methoxy-5-(5-trifluormethyl-1H-tetrazol-1-yl)benzoyl)-3-(2-(4-phenyl-4-((4-carboethoxymethylpiperazin-1-yly1)carboxamido)piperidin-1-yl)ethyl)-3-(3,4-dichlorophenyl)pyrrolidine;

1-(2-methoxy-5-(5-methyl-1H-tetrazol-1-yl)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-(3,5-bis-(trifluoromethyl)benzoyl)-3-(2-(4-phenyl-4-((4-carboethoxymethylpiperazin-1-yl)carboxamido)piperidin-1-yl)ethyl)-3-(3,4-dichlorophenyl)pyrrolidine;

1-benzoyl-3-(2-(4-phenyl-4-((4-carboethoxymethylpiperazin-1-yl)carboxamido)piperidin-1-yl)ethyl)-3-phenylpyrrolidine;

1-benzoyl-3-(2-(4-phenyl-4-((4-carboethoxymethylpiperazin-1-yl)carboxamido)piperidin-1-yl)ethyl)-3-(3,4-dichlorophenyl)pyrrolidine;

1-benzoyl-3-(3-(4-phenyl-4-((4-carboethoxymethylpiperazin-1-yl)carboxamido)piperidin-1-yl)propyl)-3-(3,4-dichlorophenyl)pyrrolidine;

1-(3,5-bis(trifluoromethyl)benzyl)-3-(3-(4-phenyl-4-((4-carboethoxymethylpiperazin-1-yl)carboxamido)piperidin-1-yl)propyl)-3-(3,4-dichlorophenyl)-5-oxopyrrolidine;

1-(3,4,5-trimethoxybenzoyl)-3-(2-(4-(pyrid-4-yl)-4-((4-carboethoxymethylpiperazin-1-yl)carboxamido)piperidin-1-yl)ethyl)-3-(3,4-dichlorophenyl)pyrrolidine;

1-benzoyl-3-(2-(4-(pyrid-4-yl)-4-((4-carboethoxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((4-carboethoxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((4-carboethoxymethylpiperazin-1-yl)carboxamido)piperidin-1-yl)ethyl)-3-(3,4-dichlorophenyl)pyrrolidine;

1-benzoyl-3-(2-(4-(pyrid-4-yl)-4-((4-carboethoxymethylpiperazin-1-yl)carboxamido)piperidin-1-yl)ethyl)-3-phenylpyrrolidine;

1-(3,4,5-trimethoxybenzyl)-3-(2-(4-(pyrid-4-yl)-4-((4-carboethoxymethylpiperazin-1-yl)carboxamido)piperidin-1-yl)ethyl)-3-phenylpyrrolidine;

1-(3,4,5-trimethoxybenzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine;

1-benzoyl-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine;

1-benzoyl-3-(2-(4-(pyrid-3-yl)-4-((4-carboethoxymethylpiperazin-1-yl)carboxamido)piperidin-1-yl)ethyl)-3-phenylpyrrolidine;

1-(3,4,5-trimethoxybenzyl)-3-(2-(4-(pyrid-3-yl)-4-((4-carboethoxymethylpiperazin-1-yl)carboxamido)piperidin-1-yl)ethyl)-3-phenylpyrrolidine;

1-(3,4,5-trimethoxybenzoyl)-3-(2-(4-(pyrid-2-yl)-4-((4-carboethoxymethylpiperazin-1-yl)carboxamido)piperidin-1-yl)ethyl)-3-(3g4-dichlorophenyl)pyrrolidine;

1-benzoyl-3-(2-(4-(pyrid-2-yl)-4-((4-carboethoxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((4-carboethoxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((4-carboethoxymethylpiperazin-1-yl)carboxamido)piperidin-1-yl)ethyl)-3-(3,4-dichlorophenyl)pyrrolidine;

1-benzoyl-3-(2-(4-(pyrid-2-yl)-4-((4-carboethoxymethylpiperazin-1-yl)carboxamido)piperidin-1-yl)ethyl)-3-phenylpyrrolidine;

1-(3,4,5-trimethoxybenzoyl)-3-(2-(4-(pyrid-2-yl)-4-((4-carboethoxymethylpiperazin-1-yl)carboxamido)piperidin-1-yl)ethyl)-3-phenylpyrrolidine;

1-(3,4,5-trimethoxybenzoyl)-3-(2-(4-phenyl-4-((4-carboxymethylpiperazin-1-yl)carboxamido)piperidin-1-yl)ethyl)-3-phenylpyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3-chlorophenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3,4-difluorophenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3-fluorophenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3(4fluorophenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(4-trifulormethylphenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3,4-dimethylphenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3,4-dimhoxphenyl)pyrrolidine;

1-(3,4,5-trimethoxybenzoyl)-3-(2-(4-phenyl-4-((4-carboxymethylpiperazin-1-yl)carboxamido)piperidin-1-yl)ethyl)-3-(3-methoxyphenyl)pyrrolidine;

1-benzoyl-3-(2-(4-phenyl-4-((4-carboxymethylpiperazin-1-yl)carboxamnido)piperidin-1-yl)ethyl)-3-(3,4-dichlorophenyl)pyrrolidine;

1-(4-chlorobenzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(3-(2-propyloxy)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(2-methoxybenzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(3-(1H-tetrazol-1-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(2-methoxy-5-(5-triflurormethyl-1H-tetrazol-1-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(2-methoxy-5-(5-methyl-1H-tetrazol-1-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-(3,5-bis-(trifluoromethyl)benzoyl)-3-(2-(4-phenyl-4-((4-carboxymethylpiperazin-1-yl)carboxamido)piperidin-1-yl)ethyl)-3-(3,4-dichlorophenyl)pyrrolidine;

1-benzoyl-3-(2-(4-phenyl-4-((4-carboxymethylpiperazin-1-yl)carboxamido)piperidin-1-yl)ethyl)-3-phenylpyrrolidine;

1-benzoyl-3-(2-(4-phenyl-4-((4-carboxymethylpiperazin-1-yl)carboxamido)piperidin-1-yl)ethyl)-3-(3,4-dichlorophenyl)pyrrolidine;

1-benzoyl-3-(3-(4-phenyl-4-((4-carboxymethylpiperazin-1-yl)carboxamido)piperidin-1-yl)propyl)-3-(3,4-dichlorophenyl)pyrrolidine;

1-(3,5-bis(trifluoromethyl)benzyl)-3-(3-(4-phenyl-4-((4-carboxymethylpiperazin-1-yl)carboxamido)piperidin-1-yl)propyl)-3-(3,4-dichlorophenyl)-5-oxopyrrolidine;

1-(3,4,5-trimethoxybenzoyl)-3-(2-(4-(pyrid-4-yl)-4-((4-carboxymethylpiperazin-1-yl)carboxamido)piperidin-1-yl)ethyl)-3-(3,4-dichlorophenyl)pyrrolidine;

1-benzoyl-3-(2-(4-(pyrid-4-yl)-4-((4-carboxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((4-carboxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((4-carboxymethylpiperazin-1-yl)carboxamido)piperidin-1-yl)ethyl)-3-(3,4-dichlorophenyl)pyrrolidine;

1-benzoyl-3-(2-(4-(pyrid-4-yl)-4-((4-carboxymethylpiperazin-1-yl)carboxamido)piperidin-1-yl)ethyl)-3-phenylpyrrolidine;

1-(3,4,5-trimethoxybenzyl)-3-(2-(4-(pyrid-4-yl)-4-((4-carboxymethylpiperazin-1-yl)carboxamido)piperidin-1-yl)ethyl)-3-phenylpyrrolidine;

1-(3,4,5-trimethoxybenzoyl)-3-(2-(4-(pyrid-3-yl)-4-((4-carboxymethylpiperazin-1-yl)carboxamido)piperidin-1-yl)ethyl)-3-(3,4-dichlorophenyl)pyrrolidine;

1-benzoyl-3-(2-(4-(pyrid-3-yl)-4-((4-carboxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((4-carboxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((4-carboxymethylpiperazin-1-yl)carboxamido)piperidin-1-yl)ethyl)-3-(3,4-dichlorophenyl)pyrrolidine;

1-benzoyl-3-(2-(4-(pyrid-3-yl)-4-((4-carboxymethylpiperazin-1-yl)carboxamido)piperidin-1-yl)ethyl)-3-phenylpyrrolidine;

1-(3,4,5-trimethoxybenzyl)-3-(2-(4-(pyrid-3-yl)-4-((4-carboxymethylpiperazin-1-yl)carboxamido)piperidin-1-yl)ethyl)-3-phenylpyrrolidine;

1-(3,4,5-trimethoxybenzoyl)-3-(2-(4-(pyrid-2-yl)-4-((4-carboxymethylpiperazin-1-yl)carboxamido)piperidin-1-yl)ethyl)-3-(3,4-dichlorophenyl)pyrrolidine;

1-benzoyl-3-(2-(4-(pyrid-2-yl)-4-((4-carboxymethylpiperazin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((4-carboxymethylpiperazin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((4-carboxymethylpiperazin-1-yl)carboxamido)piperidin-1-yl)ethyl)-3-(3,4-dichlorophenyl)pyrrolidine;

1-benzoyl-3-(2-(4-(pyrid-2-yl)-4-((4-carboxymethylpiperazin-1-yl)carboxamido)piperidin-1-yl)ethyl)-3-phenylpyrrolidine;

1-(3,4,5-trimethoxybenzoyl)-3-(2-(4-(pyrid-2-yl)-4-((4-carboxymethylpiperazin-1-yl)carboxamido)piperidin-1-yl)ethyl)-3-phenylpyrrolidine;

1-(3,4,5-trimethoxybenzoyl)-3-(2-(4-phenyl-4-((4-carboxypiperidin-1-yl)carboxamido)piperidin-1-yl)ethyl)-3-phenylpyrrolidine;

1-(3,4,5-trimethoxybenzoyl)-3-(2-(4-phenyl-4-((4-carboxypiperidin-1-yl)carboxamido)piperidin-1-yl)ethyl)-3-(4-fluorophenyl)pyrrolidine;

1-(3,4,5-trimethoxybenzoyl)-3-(2-(4-phenyl-4-((4-carboxypiperidin-1-yl)carboxamido)piperidin-1-yl)ethyl)-3-(3,4-dichlorophenyl)pyrrolidine;

1-benzoyl-3-(2-(4-phenyl-4-((4-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((4-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((4-carboxypiperidin-1-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((4-carboxypiperidin-1-yl)carboxamido)piperidin-1-yl)ethyl)-3-(3,4-dichlorophenyl)pyrrolidine;

1-benzoyl-3-(2-(4-phenyl-4-((4-carboxypiperidin-1-yl)carboxamido)piperidin-1-yl)ethyl)-3-phenylpyrrolidine;

1-(3,4,5-trimethoxybenzoyl)-3-(2-(4-(pyrid-4-yl)-4-((4-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((4-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((4-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((4-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((4-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((4-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((4-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((4-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((4-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((3-carboxypiperidin-1-yl)carboxamido)piperidin-1-yl)ethyl)-3-phenylpyrrolidine;

1-(3,4,5-trimethoxybenzoyl)-3-(2-(4-phenyl-4-((3-carboxypiperidin-1-yl)carboxamido)piperidin-1-yl)ethyl)-3-(4-fluorophenyl)pyrrolidine;

1-(3,4,5-trimethoxybenzoyl)-3-(2-(4-phenyl-4-((3-carboxypiperidin-1-yl)carboxamido)piperidin-1-yl)ethyl)-3-(3,4-dichlorophenyl)pyrrolidine;

1-benzoyl-3-(2-(4-phenyl-4-((3-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((3-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((3-carboxypiperidin-1-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((3-carboxypiperidin-1-yl)carboxamido)piperidin-1-yl)ethyl)-3-(3,4-dichlorophenyl)pyrrolidine;

1-benzoyl-3-(2-(4-phenyl-4-((3-carboxypiperidin-1-yl)carboxamido)piperidin-1-yl)ethyl)-3-phenylpyrrolidine;

1-(3,4,5-trimethoxybenzoyl)-3-(2-(4-(pyrid-4-yl)-4-((3-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((3-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((3-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((3-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((3-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((3-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((3-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((3-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((3-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((2-carboxypiperidin-1-yl)carboxamido)piperidin-1-yl)ethyl)-3-phenylpyrrolidine;

1-(3,4,5-trimethoxybenzoyl)-3-(2-(4-phenyl-4-((2-carboxypiperidin-1-yl)carboxamido)piperidin-1-yl)ethyl)-3-(4-fluorophenyl)pyrrolidine;

1-(3,4,5-trimethoxybenzoyl)-3-(2-(4-phenyl-4-((2-carboxypiperidin-1-yl)carboxamido)piperidin-1-yl)ethyl)-3-(3,4-dichlorophenyl)pyrrolidine;

1-benzoyl-3-(2-(4-phenyl-4-((2-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((2-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((2-carboxypiperidin-1-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((2-carboxypiperidin-1-yl)carboxamido)piperidin-1-yl)ethyl)-3-(3,4-dichlorophenyl)pyrrolidine;

1-benzoyl-3-(2-(4-phenyl-4-((2-carboxypiperidin-1-yl)carboxamido)piperidin-1-yl)ethyl)-3-phenylpyrrolidine;

1-(3,4,5-trimethoxybenzoyl)-3-(2-(4-(pyrid-4-yl)-4-((2-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((2-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((2-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((2-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((2-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((2-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((2-carboxypiperidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((2-carboxypiperidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((2-carboxypiperidin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((3-carboxypyrrolidin-1-yl)carboxamido)piperidin-1-yl)ethyl)-3-phenylpyrrolidine;

1-(3,4,5-trimethoxybenzoyl)-3-(2-(4-phenyl-4-((3-carboxypyrrolidin-1-yl)carboxamido)piperidin-1-yl)ethyl)-3-(4-fluorophenyl)pyrrolidine;

1-(3,4,5-trimethoxybenzoyl)-3-(2-(4-phenyl-4-((3-carboxypyrrolidin-1-yl)carboxamido)piperidin-1-yl)ethyl)-3-(3,4-dichlorophenyl)pyrrolidine;

1-benzoyl-3-(2-(4-phenyl-4-((3-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((3-carboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((3-carboxypyrrolidin-1-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((3-carboxypyrrolidin-1-yl)carboxamido)piperidin-1-yl)ethyl)-3-(3,4-dichlorophenyl)pyrrolidine;

1-benzoyl-3-(2-(4-phenyl-4-((3-carboxypyrrolidin-1-yl)carboxamido)piperidin-1-yl)ethyl)-3-phenylpyrrolidine;

1-(3,4,5-trimethoxybenzoyl)-3-(2-(4-(pyrid-4-yl)-4-((3-arboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((3-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((3-carboxypyrrolidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((3-carboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((3-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((3-carboxypyrrolidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((3-carboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((3-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((3-carboxypyrrolidin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((2-carboxypyrrolidin-1-yl)carboxamido)piperidin-1-yl)ethyl)-3-phenylpyrrolidine;

1-(3,4,5-trimethoxybenzoyl)-3-(2-(4-phenyl-4-((2-arboxypyrrolidin-1-yl)carboxamido)piperidin-1-yl)ethyl)-3-(4-fluorophenyl)pyrrolidine;

1-(3,4,5-trimethoxybenzoyl)-3-(2-(4-phenyl-4-((2-carboxypyrrolidin-1-yl)carboxamido)piperidin-1-yl)ethyl)-3-(3,4-dichlorophenyl)pyrrolidine;

1-benzoyl-3-(2-(4-phenyl-4-((2-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)bentoyl)-3-(2-(4-phenyl-4-((2-carboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((2-carboxypyrrolidin-1-yl)carboxamido)piperidin-1-yl)ethyl)-3-(3,4-dichiorophenyl)pyrrolidine;

1-(2-methoxy-5-(1H-tetrazol-5-yl)benzoyl)-3-(2-(4-phenyl-4-((2-carboxypyrrolidin-1-yl)carboxamido)piperidin-1-yl)ethyl)-3-(3,4-dichlorophenyl)pyrrolidine;

1-benzoyl-3-(2-(4-phenyl-4-((2-carboxypyrrolidin-1-yl)carboxamido)piperidin-1-yl)ethyl)-3-phenylpyrrolidine;

1-(3,4,5-trimethoxybenzoyl)-3-(2-(4-(pyrid-4-yl)-4-((2-carboxypyrrolidin-1-yl)carboxamido)piperidin-1-yl)ethyl)-3-(3,4-dichorophenyl)pyrroelidine;

1-(2-methoxy-5-(4H-triazol-4-yl)benzoyl)-3-(2-(4-(pyrid-4-yl)-4-((2-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((2-carboxypyrrolidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((2-carboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((2-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((2-carboxypyrrolidin-1-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((2-carboxypyrrolidin-1-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((2-carboxypyrrolidin-1-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((2-carboxypyrrolidin-1-yl)carboxamido)piperidin-1-yl)ethyl)-3-(3,4-dichlorophenyl)pyrrolidine;

1-(3,4,5-trimethoxybenzoyl)-3-(2-(4-phenyl-4-((3-carboxymorpholin-4-yl)carboxamido)piperidin-1-yl)ethyl)-3-phenylpyrrolidine;

1-(3,4,5-trimethoxybenzoyl)-3-(2-(4-phenyl-4-((3-arboxymorpholin-4-yl)carboxamido)piperidin-1-yl)ethyl)-3-(4-fluorophenyl)pyrrolidine;

1-(3,4,5-trimethoxybenzoyl)-3-(2-(4-phenyl-4-((3-arboxymorpholin-4-yl)carboxamido)piperidin-1-yl)ethyl)-3-(3,4-dichlorophenyl)pyrrolidine;

1-benzoyl-3-(2-(4-phenyl-4-((3-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((3-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((3-carboxymorpholin-4-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((3-carboxymorpholin-4-yl)carboxamido)piperidin-1-yl)ethyl)-3-(3,4-dichlorophenyl)pyrrolidine;

1-benzoyl-3-(2-(4-phenyl-4-((3-carboxymorpholin-4-yl)carboxamido)piperidin-1-yl)ethyl)-3-phenylpyrrolidine;

1-(3,4,5-trimethoxybenzoyl)-3-(2-(4-(pyrid-4-yl)-4-((3-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((3-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((3-carboxymorpholin-4-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((3-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((3-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((3-carboxymorpholin-4-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((3-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((3-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((3-carboxymorpholin-4-yl)carboxamido)piperidin-1-yl)ethyl)-3-(3,4-dichlorophenyl)pyrrolidine;

1-(3,4,5-trimethoxybenzoyl)-3-(2-(4-phenyl-4-((2-carboxymorpholin-4-yl)carboxamido)piperidin-1-yl)ethyl)-3-phenylpyrrolidine;

1-(3,4,5-trimethoxybenzoyl)-3-(2-(4-phenyl-4-((2-carboxymorpholin-4-yl)carboxamido)piperidin-1-yl)ethyl)-3-(4-fluorophenyl)pyrrolidine;

1-(3,4,5-trimethoxybenzoyl)-3-(2-(4-phenyl-4-((2-carboxymorpholin-4-yl)carboxamido)piperidin-1-yl)ethyl)-3-(3,4-dichlorophenyl)pyrrolidine;

1-benzoyl-3-(2-(4-phenyl-4-((2-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-((2-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-phenyl-4-((2-carboxymorpholin-4-yl)carboxamido)piperidin-1-yl)ethyl)-3-(3,4-dichlorophenyl)pyrrolidine;

1-(2-methoxy-5-(1H-tetrazol-5-yl)benzoyl)-3-(2-(4-phenyl-4-((2-carboxymorpholin-4-yl)carboxamido)piperidin-1-yl)ethyl)-3-(3,4-dichlorophenyl)pyrrolidine;

1-benzoyl-3-(2-(4-phenyl-4-((2-carboxymorpholin-4-yl)carboxamido)piperidin-1-yl)ethyl)-3-phenylpyrrolidine;

1-(3,4,5-trimethoxybenzoyl)-3-(2-(4-(pyrid-4-yl)-4-((2-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-4-yl)-4-((2-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-((2-carboxymorpholin-4-yl)carboxamido)piperidin-1-yl)ethyl)-3-(3,4-dichlorophenyl)pyrrolidine;

1-(3,4,5-trimethoxybenzoyl)-3-(2-(4-(pyrid-3-yl)-4-((2-arboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-3-yl)-4-((2-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-((2-carboxymorpholin-4-yl)carboxamido)piperidin-1-yl)ethyl)-3-(3,4-dichlorophenyl)pyrrolidine;

1-(3,4,5-trimethoxybenzoyl)-3-(2-(4-(pyrid-2-yl)-4-((2-carboxymorpholin-4-yl)carboxamido)piperidin-1-yl)ethyl)-3-(3,4-dichlorophenyl)pyrrolidine;

1-(2-methoxy-5-(4H-triazol-4-yl)benzoyl)-3-(2-(4-(pyrid-2-yl)-4-((2-carboxymorpholin-4-yl)carboxamido)piperidin-1-yl)ethyl)-3-(3,4-dichlorophenyl)pyrrolidine;

1-(2-methoxy-5-(1H-tetrazol-1-yl)benzoyl)-3-(2-(4-(pyrid-2-yl)-4-((2-carboxymorpholin-4-yl)carboxamido)piperidin-1-yl)ethyl)-3-(3,4-dichlorophenyl)pyrrolidine.

A general synthetic procedure is set forth in Reaction Scheme A for preparing these compounds of formula (1). The reagents and starting materials are readily available to one of ordinary skill in the arts In Reaction Scheme A, all substituents, unless otherwise indicated, are as previously defined.

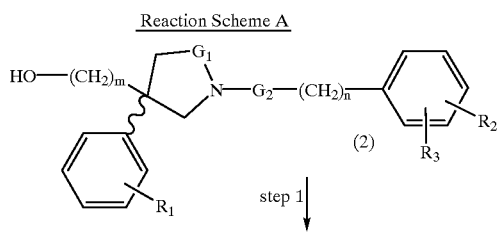

Reaction Scheme A

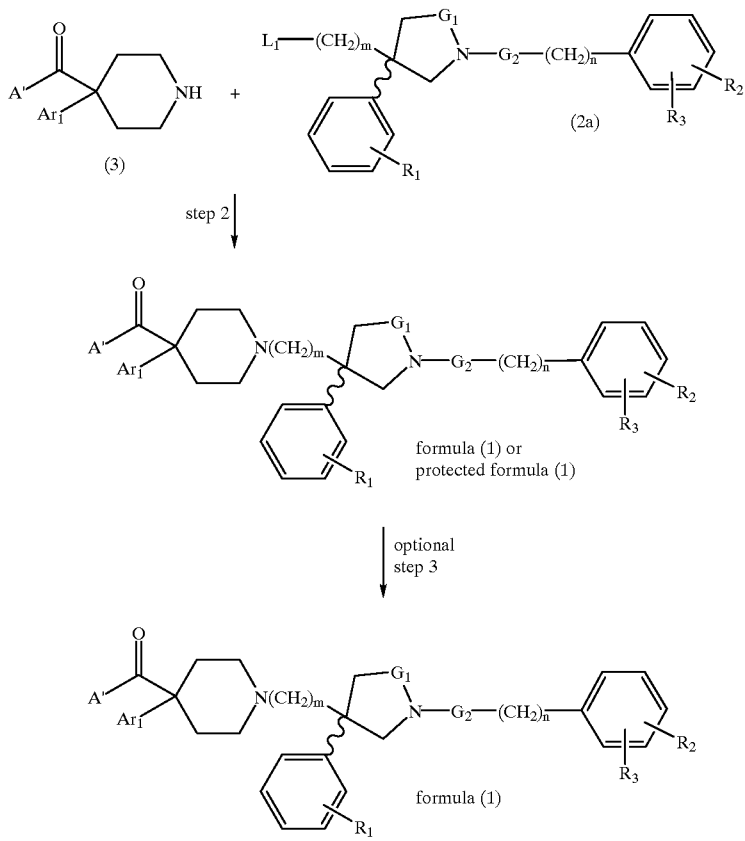

In Reaction Scheme A. step 1 the hydroxy group of an appropriate 3-(ω-hydroxyalkyl)pyrrolidine of formula 2 is converted to an appropriate leaving group, $L_1$. An appropriate 3-(ω-hydroxyalkyl)pyrrolidine of formula 2 is one in which m, n, $G_1$, $G_2$, $R_1$, $R_2$, and $R_3$ are as desired in the final product of formula (1). An appropriate 3-(ω-hydroxyalkyl) pyrrolidine of formula 2 may also have the stereochemistry as desired in the final product of formula (1). Appropriate compounds of formula 2 can be prepared as described herein and as described in U.S. Pat. Nos. 5,340,822 and 576357510 and PCT WO 94/26735 and WO 96/06094. An appropriate leaving group, $L_1$, is one which can be displaced by a piperidine of formula 3 to give a compound of formula (1) or protected compound of formula (1) Appropriate leaving groups, $L_1$, include but are not limited to chloro, bromom iodo, mesylate, tosylate, and the like, with mesylate being preferred. The conversion of hydroxy groups to leaving groups such as chloro, bromo, iodo, mesylate, and tosylate is well known and appreciated in the art.

For example, compounds in which $L_1$ is bromo are formed by contacting an appropriate 3-(ω-hydroxyalkyl) pyrrolidine of formula 2 with 1.0 to 1.5 molar equivalents of carbon tetrabromide and 1.0 to 1.75 molar equivalents triphenylphosphine. (P. J. Kocienski et al. *J. Org. Chem.* 42, 353–355 (1977)). The reaction is carried out by combining the 3-(ω-hydroxyalkyl)pyrrolidine of formula 2 with carbon tetrabromide in a suitable solvent, such as dichloromethane or chloroform and then adding a solution of triphenylphosphine in a suitable solvents such as dichloromethane or chloroform. Generally the reaction is carried out at temperatures of from −10° C. to ambient temperature. Generally, the reactions require from 5 minutes to 24 hours. The product can be isolated and purified by techniques well known in the arts such as extraction, evaporation, trituration, chromatography, and recrystallization.

Compounds in which $L_1$ is bromo are also formed by contacting an appropriate 3-(ω-hydroxyalkyl)pyrrolidine of formula 2 with a slight molar excess of triphenylphosphine dibromide. (R. F Borch et al. *J. Am. Chem. Soc.* 99, 1612–1619 (1977)). The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporations trituration, chromatography, and recrystallization.

Alternately, for example, compounds in which $L_1$ is mesylate are formed by contacting an appropriate 3-(ω-hydroxyalkyl)pyrrolidine of formula 2 with 1 to 2 molar equivalents of methanesulfonyl chloride. The reaction is carried out in a suitable solvent, such as dichloromethane, chloroform, toluene, benzene, or pyridine. The reaction is carried out in the presence of a suitable base, such as triethylamine, N,N-diisopropylethylamine, N-methylmorpholine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of formula 2a in which $L_1$ is iodo can be prepared from compounds of formula 2a in which $L_1$ is mesylate, chloro, or bromo by an exchange reaction, such as the Finkelstein reaction.

For example, a compound of formula 2a in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone or butanone. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A, step 2, an appropriate 3-($\omega$-$L_1$-alkyl)pyrrolidine of formula 2a reacts with an appropriate ipiperidine compound of formula 3 or salt thereof. An appropriate piperidine compound of formula 3 is one in which $Ar_1$ is as desired in the final product of formula (1) and A' is either A as desired in the final product of formula (1), gives rise after deprotection to A as desired in the final product of formula (1), or gives rise after amidation to A as desired in the final product of formula (1).

For example, an appropriate 3-($\omega$-$L_1$-alkyl)pyrrolidine of formula 2a is contacted with an appropriate piperidine compound of formula 3 or salt thereof to give a compound of formula (1) or a protected compound of formula (1). The reaction is carried out in a suitable substantially anhydrous solvent, such as tetrahydrofuran, pyridine, acetonitrile, toluene, or dimethylformamide using from 1.0 to 6.0 molar equivalents of a suitable base, such as triethylamine, pyridine, or N,N-diisopropylethylamine. When a salt of an appropriate piperidine of formula 3 is used, an additional molar excess of a suitable base is used. The reaction may be facilitated by the addition of a catalytic amount, 0.1 to 0.5 molar equivalents, of an iodide salt, such as sodium iodide or potassium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

Alternately, the reaction is carried out in a suitable mixed solvent, such as toluene/water mixtures, ethyl acetate/water mixtures, or tetrahydrofuran/water mixtures, using from 1.0 to 6.0 molar equivalents of a suitable base, such as sodium hydroxide, potassium hydroxide, sodium carbonate, sodium bicarbonate, potassium carbonate, or potassium bicarbonate. As above, when a salt of an appropriate piperidine of formula 3 is used, an additional molar excess of a suitable base is used. The reaction may be facilitated by the addition of a catalytic amount, 0.1 to 0.5 molar equivalents, of an iodide salt, such as sodium iodide or potassium iodide. The reaction is generally carried out at temperatures of from ambient temperature to the refluxing temperature of the mixed solvent. Generally, the reactions require 1 to 150 hours. The product can be isolated and purified by techniques well known in the art, such as extraction, evaporation, trituration, chromatography, and recrystallization.

In Reaction Scheme A, optional step 3, a protected compound of formula (1) is deprotected to give a compound of formula (1). A deprotection reaction, such as deprotection of a carboxy protecting group utilizing suitable protecting groups such as those described in *Protecting Groups in Organic Synthesis* by T. Greene is well known and appreciated in the art.

In addition, pharmaceutically acceptable salts of a compound of formula (1) are readily prepared from compounds of formula (1) by methods and techniques well known and appreciated in the art.

Reaction Scheme B is a general scheme for preparing alcohols of structure 2 used as a starting material in Reaction Scheme A. The reagents and starting materials are readily available to one of ordinary skill in the art. In Reaction Scheme B, all substituents, unless otherwise indicated, are as previously defined.

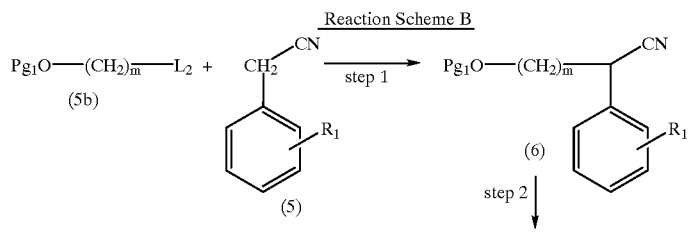

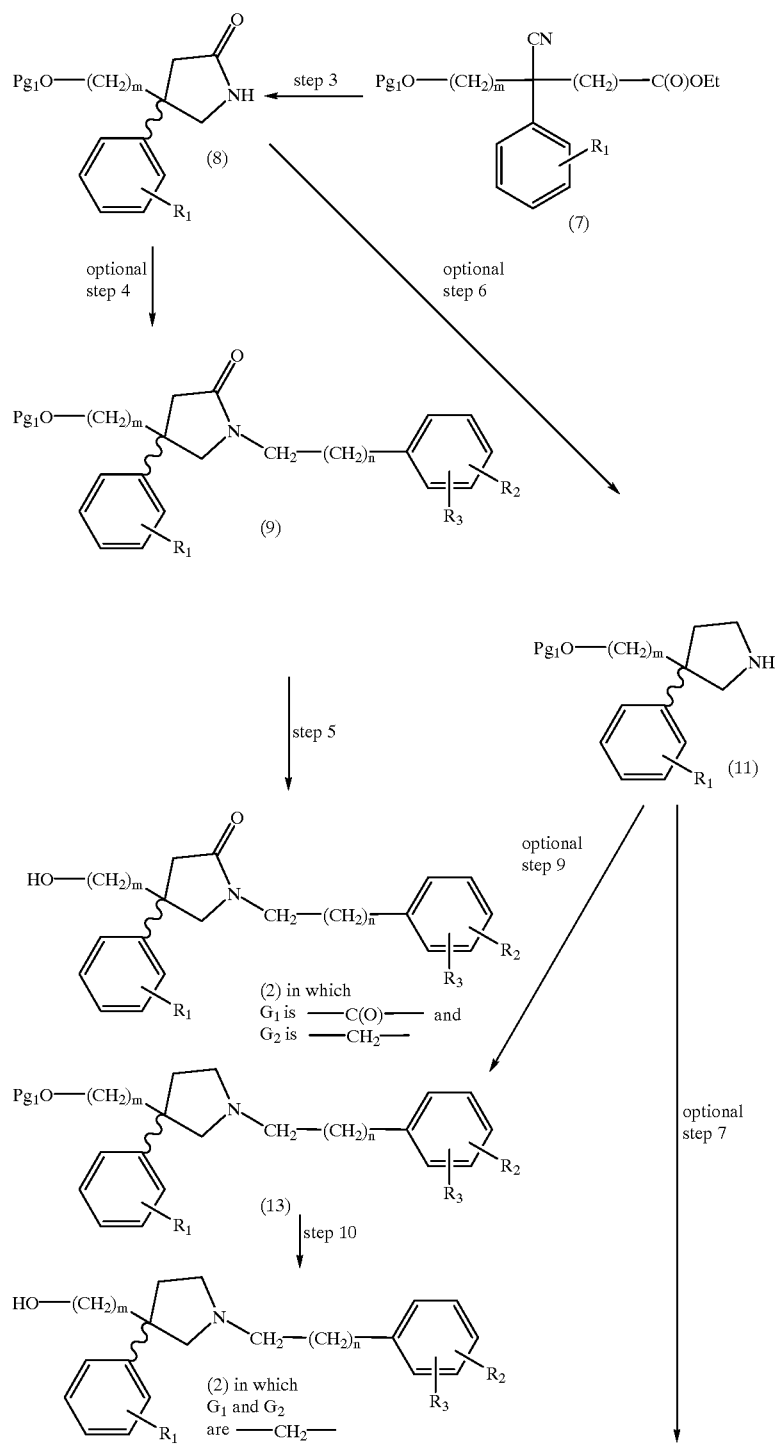

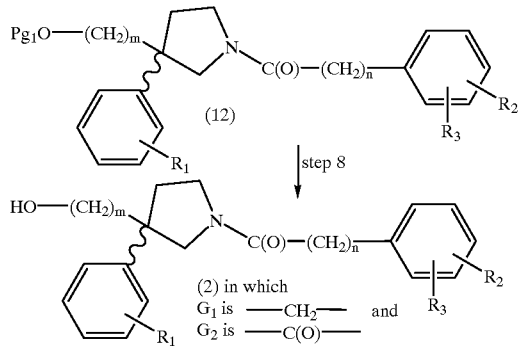

In Reaction Scheme B, step 1, an appropriate nitrile of structure 5 is alkylated with an appropriate protected alcohol of structure 5b to give an ω-(protectedhydroxy) alkylnitrile of structure 6.

An appropriate nitrile of structure 5 is one in which RI is as desired in the final product of formula (1). An appropriate protected alcohol of structure 5b is one in which m is as desired in the final product of formula (1) and the leaving groupb, $L_2$, is one which can be displaced by an anion derived from an appropriate nitrile of structure 5. Suitable leaving groups include but are not limited to chlorol bromob, iodo, and mesylate with iodo and bromo being preferred. The selection and use of a suitable hydroxy protecting groupb, $Pg_1$, such as those described in *Protecting Groups in Organic Synthesis* by T. Greene are well known and appreciated in the art. In Reaction Scheme B, step 1, the use of tetrahyropyran-2-yl and t-butyldimethylsilyl protecting groups are generally preferred.

For example, the appropriate nitrile of structure 5 is contacted with 10 to 1.2 molar equivalents of the appropriate protected alcohol of structure 5b. The reaction is carried out in the presence of approximately an equimolar amount of a suitable base, such as sodium hydrideb, sodium bis-(trimethylsilyl)amideb, potassium t-butoxide, or lithium diisopropylamide with sodium hydride and sodium bis-(trimethylsilyl)amide being preferred. The reaction is carried out in a solvent, such as dimethylformamide or tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme B, step 2, the ω-(protectedhydroxy) alkylnitrile of structure 6 is alkylated with ethyl bromoacetate to give a nitrile ester compound of structure 7.

For example, the ω-(protectedhydroxy)alkylnitrile of structure 6 is contacted with approximately a molar equivalent of ethyl bromoacetate. The reaction is carried out in the presence of approximately a molar equivalent of a suitable base, such as sodium bis-(trimethylsilyl)amide or lithium diisopropylamide. The reaction is carried out in a suitable solvent, such as tetrahydrofuran. The reaction is generally carried out at temperatures of from −78° C. to 0° C. Generally the reactions require 1 to 72 hours. The product can be isolated and purified by techniques well known in the art, such as extraction, evaporation, trituration, chromatography, and recrystallization.

In Reaction Scheme B, step 3, the nitrile ester compound of structure 7 is reduced and cyclized to give an 3-ω-(protectedhydroxy)alkyl-5-oxopyrrolidine compound of structure 8. The cyclization may occur spontaneously after the reduction or may be carried out in a separate step after the isolation of the intermediate amine.

For example, the nitrile ester compound of structure 7 is contacted with an excess of an appropriate reducing agent, such as sodium borohydride in the presence of cobalt (II) chloride hexahydrate or hydrogen in the presence of a suitable catalyst, such as Raney nickel or platinum oxide.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. Generally, the cyclization occurs spontaneously under these conditions. The product can be isolated and purified by techniques well known in the art, such as extraction with aqueous acid, evaporation, trituration, chromatography, and recrystallization.

When Raney nickel is used, the reaction is carried out in a suitable solvent containing ammonia, such as ethanol/aqueous ammonium hydroxide or methanol/aqueous ammonium hydroxide. The reaction is generally carried out at temperatures of from ambient temperature to 70° C. The reaction is carried out with hydrogen at pressures of from 15 psi to 120 psi in an apparatus designed for carrying out reactions under pressure, such as a Parr hydrogenation apparatus. Generally, the cyclization occurs spontaneously under these conditions The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, an amine intermediate is obtained under these conditions and is isolated by carefully removing the catalyst by filtration and evaporation. The amine intermediate is cyclized by heating in a suitable solvent, such as ethanol, methanol, toluene, or chlorobenzene. The reaction is generally carried out at temperatures of from 50° C. to the refluxing temperature of the solvent. Generally, the reaction requires 8 to 48 hours. The product can be purified by extraction, evaporation, trituration, chromatography, and recrystallization.

In Reaction Scheme B, optional step 4, the 3-(ω-(protectedhydroxy)alkyl)-5-oxopyrrolidine compound of structure 8 is alkylated with an appropriate alkylating agent to give a compound of structure 9. An appropriate alkylating agent, $X_1$—$CH_2$—$(CH_2)_n$—$Ph_1$, is one in which $X_1$ is methanesulfonyl, chloro, bromob, or iodo, n is as desired in the final product of formula (1) and $Ph_1$ is phenyl or substituted phenyl having $R_2$ and $R_3$ as desired in the final product of formula (1).

For example, the 3-(ω-(protectedhydroxy)alkyl)-5-oxopyrrolidine compound of structure 8 is contacted with from 1 to 5 molar equivalents of an appropriate alkylating agent. The reaction is carried out in a suitable solvent, such as tetrahydrofuran, dimethyl sulfoxide, or dimethylformamide. The reaction is carried out in the presence of a base, such as sodium hydride, potassium t-butoxide, potassium bis(trimethylsilyl)amide, or lithium diisopropylamide with sodium hydride and potassium bis(trimethylsilyl)amide being preferred The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme B, step 5, compound of structure 9 is deprotected to give an alcohol of structure 2 in which $G_1$ is —C(O)— and $G_2$ is —$CH_2$—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme B, optional step 6, the 3-(ω-(protectedhydroxy)alkyl)-5-oxopyrrolidine compound of structure 8 is reduced to give a 3-(ω-(protectedhydroxy)alkyl)pyrrolidine compound of structure 11.

For example, the 3-(ω-(protectedhydroxy)alkyl)-5-oxopyrrolidine compound of structure 8 is contacted with an excess of a suitable reducing agent, such as lithium aluminum hydride, aluminum hydride, or borane dimethyl sulfide complex. The reaction is carried out in a suitable solvent, such as tetrahydrofuran. The reaction is generally carried out at temperatures of from 0° C. to the refluxing temperature of the solvent. Generally, the reactions require 1 to 72 hours. The product can be isolated and purified by techniques well known in the art, such as quenching of borane or aluminum complexes, extraction, evaporation, trituration, chromatography, and recrystallization.

In Reaction Scheme B, optional step 7, the 3-(ω-(protectedhydroxy)alkyl)pyrrolidine compound of structure 11 is aroylated with an appropriate aroyl acid, aroyl ester, aroyl halide, aroyl anhydride, or aroyl mixed anhydride, $X_2$—C(O)—$(CH_2)_n$—$Ph_2$, to give a compound of structure 12. An appropriate aryl acid, aryl ester, aroyl halide, aroyl anhydride, or aroyl mixed anhydride, $X_2$—C(O)—$(CH_2)_n$—$Ph_2$, is one in which $X_2$ is hydroxyl; an activated ester, such as O-hydroxysuccinimide, O-hydroxybenztriazole; an activated leaving group, such as chloro, bromo; or a group which forms an anhydride; or mixed anhydride, n is as desired in the final product of formula (1), and $Ph_2$ is phenyl or substituted phenyl having $R_2$ and $R_3$ as desired in formula (1).

For example, the 3-(ω-(protectedhydroxy)alkyl) pyrrolidine compound of structure 11 is contacted with 1 to 1.5 molar equivalents of an appropriate aroyl acid, aroyl ester, aroyl halide, aroyl anhydride, or aroyl mixed anhydride. The reaction is carried out in a suitable solvent, such as dichloromethane, tetrahydrofuran, acetonitrile, dimethylformamide, or pyridine. The reaction is carried out in the presence of a base, such as triethylamine, N-methylmorpholine, N,N-diisopropylethylamine, or pyridine. The reaction is generally carried out at temperatures of from −20° C. to 50° C. Generally, the reactions require 1 to 6 hours. The product can be isolated and purified by techniques well known in the art, such as extraction, evaporation, trituration, chromatography, and recrystallization.

Alternately, for example, the 3-(ω-(protectedhydroxy) alkyl)pyrrolidine compound of structure 11 is contacted with 1 to 1.5 molar equivalents of an appropriate aroyl acid, aryl ester, aryl halide, aroyl anhydride, or aryl mixed anhydride. The reaction is carried out in a suitable mixed solvent, such as tetrahydrofuran/water, acetone/water, or ethyl acetate/water. The reaction is carried out in the presence of a base, such as sodium carbonate, sodium bicarbonate, potassium carbonate, potassium bicarbonate, sodium hydroxide, or potassium hydroxides The reaction may be carried out in the presence of a suitable catalyst, such as sodium iodide or potassium iodide. The reaction is generally carried out at temperatures of from −20° C. to 50° C. Generally, the reactions require 1 to 24 hours. The product can be isolated and purified by techniques well known in the art, such as extraction, evaporation, trituration, chromatography, and recrystallization.

In Reaction Scheme B, step 8, the compound of structure 12 is deprotected to give an an alcohol of structure 2 in which $G_1$ is —$CH_2$— and $G_2$ is —C(O)—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme B, optional step 9, the 3-(ω-(protectedhydroxy)alkyl)pyrrolidine compound of structure 11 is alkylated with an appropriate alkyl halide, $X_3$—$CH_2$—$(CH_2)_n$—$Ph_3$, to give a compound of structure 13. An appropriate alkyl halide is one in which $X_3$ is chloro, bromo, or mesylate and n is as desired in the final product of formula (1), and $Ph_3$ is phenyl or substituted phenyl having $R_2$ and $R_3$ as desired in formula (1).

For example, the 3-(ω-(protectedhydroxy)alkyl) pyrrolidine compound of structure 11 is contacted with from 1.0 to 1.2 molar equivalents of an appropriate alkyl halide. The reaction is carried out in a suitable solvent, such as tetrahydrofuran, dimethyl sulfoxide, acetonitrile, toluene, or dimethylformamide. The reaction is carried out in the presence of a base, such as sodium carbonate, sodium bicarbonate, potassium carbonate, triethylamine, N,N-diisopropylethylamine, or pyridine. The reaction is generally carried out at temperatures of from 0° C. to reflux temperature of the solvent. Generally, the reactions require 1 to 72 hours. The product can be isolated and purified by techniques well known in the art, such as extraction, evaporation, trituration, chromatography, and recrystallization.

Alternately, for example, the 3-(ω-(protectedhydroxy) alkyl)pyrrolidine compound of structure 11 is contacted with from 1.0 to 1.2 molar equivalents of an appropriate alkyl halide. The reaction is carried out in a suitable mixed solvent, such as tetrahydrofuran/water, toluene/water, or ethyl acetate/water The reaction is carried out in the presence of a base, such as sodium carbonate, sodium bicarbonate, potassium carbonate, or potassium bicarbonate. The reaction is generally carried out at temperatures of from 0° C. to reflux temperature of the solvent. Generally, the reactions require 1 to 72 hours. The product can be isolated and purified by techniques well known in the art, such as extraction, evaporation, trituration, chromatography, and recrystallization.

In Reaction Scheme B, step 10, the compound of structure 13 is deprotected to give an alcohol of structure 2 in which $G_1$ and $G_2$ are —$CH_2$—. A deprotection reaction, such as the removal of hydroxy protecting groups utilizing suitable protecting groups such as those described in *Protecting Groups in Organic Synthesis* by T. Greene is well known and appreciated in the art.

Reaction Scheme C sets forth a synthetic procedure for preparing alcohols of structure 2 in which m is 2 and intermediates of structure 8 in which m is 2 used in Reaction Scheme Bb. For preparing alcohols of structure 2 in which m is 2 the method of Reaction Scheme C is generally preferredb. In Reaction Scheme C, the reagents and starting materials are readily available to one of ordinary skill in the art and all substituents, unless otherwise indicated, are as previously defined.

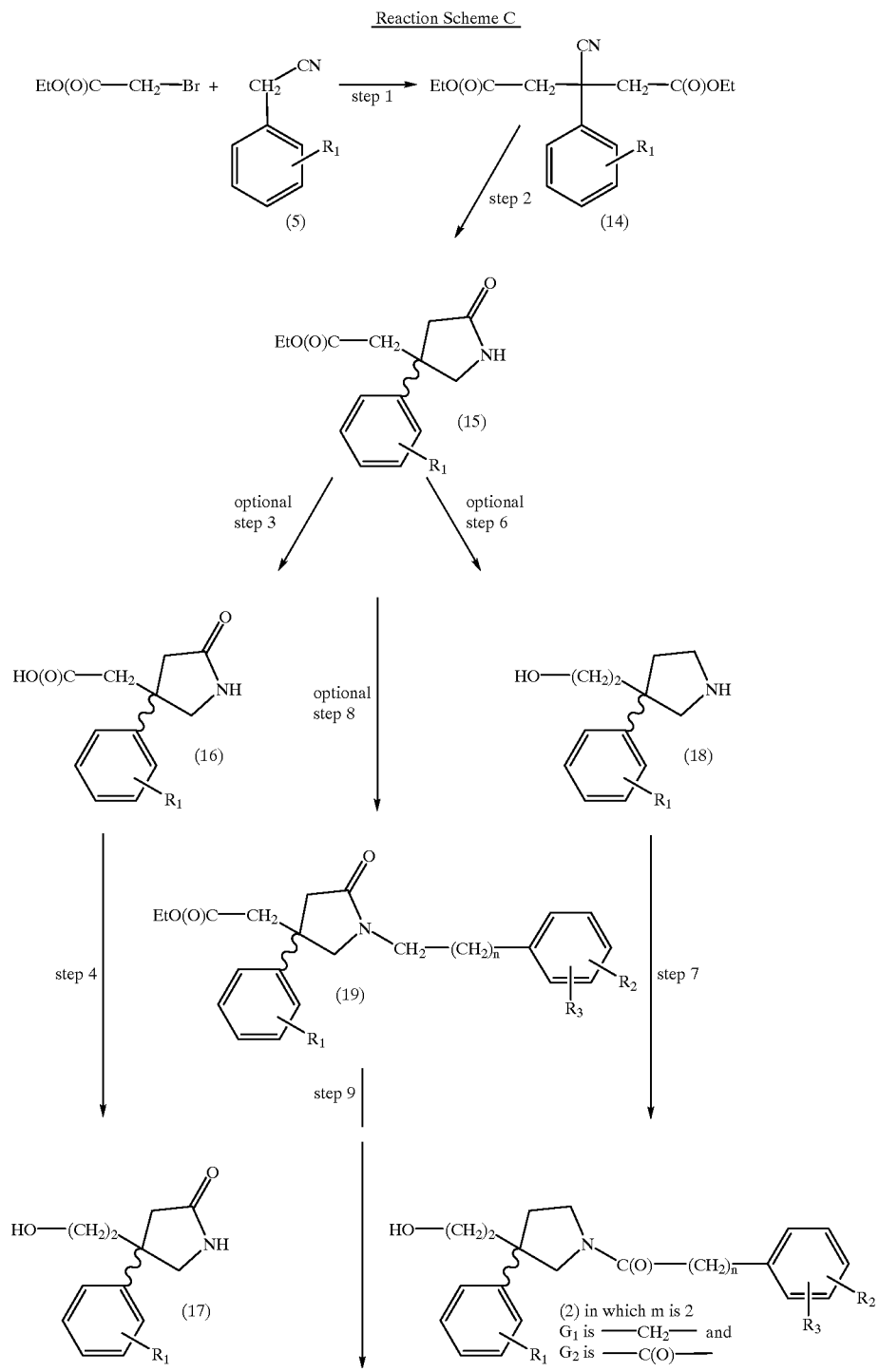

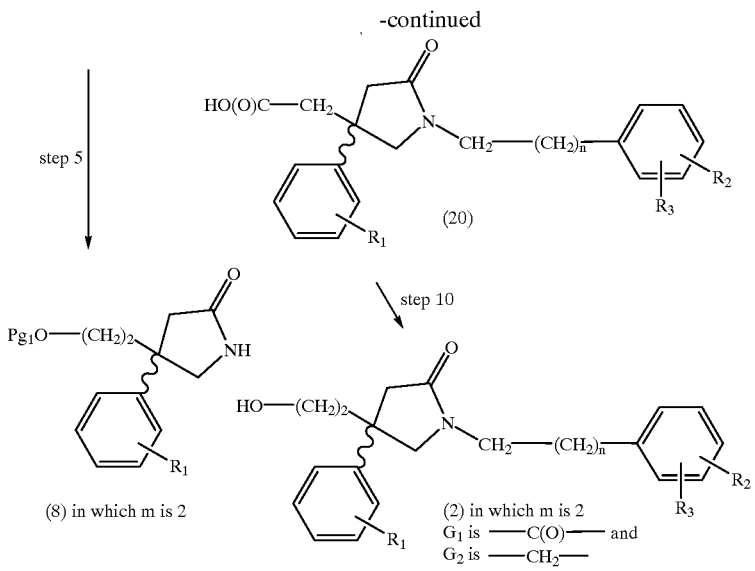

In Reaction Scheme C, step 1, an appropriate nitrile of structure 5 is bis-alkylated with ethyl bromoacetate to give a nitrile bis-ester compound of structure 14. An appropriate nitrile of structure 5 is one in as defined in Reaction Scheme B, step 1.

For example, an appropriate nitrile of structure 5 is contacted with 2.0 to 3.0 molar equivalents of ethyl bromoacetate. The reaction is carried out in the presence of approximately 2.0 to 3.0 molar equivalents of a suitable base, such as sodium bis(trimethylsilyl)amide or lithium diisopropylamide. The reaction is carried out in a suitable solvents such as tetrahydrofuran. The reaction is generally carried out at temperatures of from −78° C. to 0° C. Generally, the reactions require 1 to 72 hours. The product can be isolated and purified by techniques well known in the art, such as extractions evaporations trituration, distillation, chromatography, and recrystallization.

In Reaction Scheme C, step 2, the nitrile bis-ester compound of structure 14 is reduced and cyclized to give a 5-oxo-3-acetic acid ester pyrrolidine of structure 15.

For example, the nitrile bis-ester compound of structure 14 is contacted with a suitable reducing agent, such as sodium borohydride in the presence of cobalt II chloride hexahydrate or hydrogen in the presence of a suitable catalyst, such as Raney nickel or platinum oxide as taught in Reaction Scheme B, step 3.

Alternately, for example, the nitrile bis-ester compound of structure 14 is contacted with borane or a borane complex, such as borane dimethylsulfide complex. The reaction is carried out in a suitable solvent, such as diethyl ether or tetrahydrofuran. The reaction is generally carried out at temperatures of from −20° C. to the refluxing temperature of the solvent. Generally, the reactions require 1 to 72 hours. The product can be isolated and purified by techniques well known in the art, such as quenching, extraction, evaporation, trituration, distillation, chromatography, and recrystallization.

In Reaction Scheme C, optional step 3, the 5-oxo-3-acetic acid ester pyrrolidine of structure 15 is hydrolyzed to give a 5-oxo-3-acetic acid pyrrolidine of structure 16.

For example, the 5-oxo-3-acetic acid ester pyrrolidine of structure 15 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme C, step 4, the 5-oxo-3-acetic acid pyrrolidine of structure 16 is reduced to give a 3-(2-hydroxyethyl)-5-oxopyrrolidine of structure 17.

For example, the 5-oxo-3-acetic acid pyrrolidine of structure 16 is contacted with a suitable borane reagent, such as borane dimethyl sulfide complex. The reaction is carried out in a suitable solvent, such as tetrahydrofuran or diethyl ether. The reaction is generally carried out at a temperature of from 0° C. to the refluxing temperature of the solvent. When complete, the reaction is quenched by the careful addition of a suitable aqueous acid solution, such as 1M hydrochloric acid solution. The product can be isolated and purified by techniques well known in the art, such as extraction, evaporation, trituration, chromatography, and recrystallization.

Alternately, the 5-oxo-3-acetic acid pyrrolidine of structure 16 can be reduced by formation of a mixed anhydride intermediate and contacting the mixed anhydride intermediate with a suitable mild reducing agent, such as sodium borohydride.

For example, the 5-oxo-3-acetic acid pyrrolidine of structure 16 is contacted with 1.2 to 1.7 equivalents of a suitable base, such as N-methylmorpholine, in a suitable solvent, such as tetrahydrofuran or diethyl ether. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride. After the formation of the mixed anhydride is complete, sodium borohydride is added. The product can be isolated and purified by techniques well known in the art, such as extraction, evaporation, chromatography, and recrystallization.

In Reaction Scheme C, step 5, the 3-(2-hydroxyethyl)-5-oxopyrrolidine of structure 17 is protected to give a 3-(ω- protectedhydroxyethyl)-5-oxo-pyrrolidine of structure 8 used in Reaction Scheme B. The selection and use of suitable protecting groups such as those described in *Protecting Groups in Organic Synthesis* by T. Greene is well known and appreciated in the art.

In Reaction Scheme C, optional step 6, the 5-oxo-3-acetic acid ester pyrrolidine of structure 15 is reduced to give a 3-(ω-hydroxyethyl)pyrrolidine of structure 18 as taught in Reaction Scheme B, optional step 6, using sufficient reducing agent to reduce both the amide and ester groups.

In Reaction Scheme C, step 7, the 3-(ω-hydroxyethyl) pyrrolidine of structure 18 is aroylated with an appropriate aroyl halide, aryl anhydride, or aryl mixed anhydride to give an alcohol of structure 2. An appropriate aroyl halide, aroyl anhydride, or aroyl mixed anhydride is one is one as described in Reaction Scheme B, optional step 7.

For example, the 3-(ω-hydroxyethyl)-pyrrolidine of structure 18 is contacted with 1 to 1.1 molar equivalents of an appropriate aroyl halide, aroyl anhydride, or aroyl mixed anhydride. The reaction is carried out in a suitable solvent, such as tetrahydrofuran, dichloromethane, acetone, ethyl acetate, toluene, or diethyl ether. The reaction is carried out in the presence of a base, such as N-methylmorpholine, sodium carbonate, triethylamine, N,N-diisopropylethylamine, potassium carbonate or sodium bicarbonate. The reaction is generally carried out at temperatures of from $-78°$ C. to ambient temperature. Generally, the reactions require 1 to 24 hours. The product can be isolated and purified by techniques well known in the art, such as extraction, evaporation, trituration, chromatography, and recrystallization.

Alternately, for example, the 3-(ω-hydroxyethyl)-pyrrolidine of structure 18 is contacted with 1 to 1.1 molar equivalents of an appropriate aroyl halide, aroyl anhydride, or aroyl mixed anhydride under Schotten-Baumann conditions. The reaction is carried out in a suitable solvent mixture, such as toluene/water, acetone/water, tetrahydrofuran/water, or ethyl acetate/water. The reaction is carried out in the presence of a base, such as potassium carbonate, potassium bicarbonate, sodium bicarbonate, sodium carbonate, sodium hydroxide, or potassium hydroxide. The reaction is generally carried out at temperatures of from $-20°$ C. to $50°$ C. Generally, the reactions require 15 minutes to 24 hours. The product can be isolated and purified by techniques well known in the art, such as extraction, evaporation, trituration, chromatography, and recrystallization.

In Reaction Scheme C, optional step 8, the 5-oxo-3-acetic acid ester pyrrolidine of structure 15 is alkylated with an appropriate alkyl halide to give an 1-arylalkyl-5-oxo-3-acetic acid ester pyrrolidine of structure 19. An appropriate alkyl halide is one as described in Reaction Scheme B, optional step 4.

For example, the 5-oxo-3-acetic acid ester pyrrolidine of structure 15 is contacted with from 10 to 1.2 molar equivalents of an appropriate alkyl halide. The reaction is carried out in a suitable solvent, such as tetrahydrofuran, dimethyl sulfoxide, acetonitrile, or dimethylformamide. The reaction is carried out in the presence of a base, such as sodium hydride, sodium bis(trimethylsilyl)amide, potassium t-butoxide. The reaction is generally carried out at temperatures of from $0°$ C. to $50°$ C. Generally, the reactions require 1 to 72 hours. The product can be isolated and purified by techniques well known in the art, such as extraction, evaporation, trituration, chromatography, and recrystallization.

In Reaction Scheme C, step 9, the 1-arylalkyl-5-oxo-3-acetic acid ester pyrrolidine of structure 19 is hydrolyzed to give an 1-arylalkyl-5-oxo-3-acetic acid pyrrolidine of structure 20.

For example, the 1-arylalkyl-5-oxo-3-acetic acid ester pyrrolidine of structure 19 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from $0°$ C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme C, step 10, the 1-arylalkyl-5-oxo-3-acetic acid pyrrolidine of structure 20 is reduced as taught in Reaction Scheme C, step 4, to give an alcohol of structure 2 in which m is 2, $G_1$ is —C(O)—, and $G_2$ is —$CH_2$—.

Reaction Scheme D sets forth a synthetic procedure for preparing piperidine compounds of structure 3 and 3a used as starting materials in Reaction Schemes Ab.1 and Ab.2.

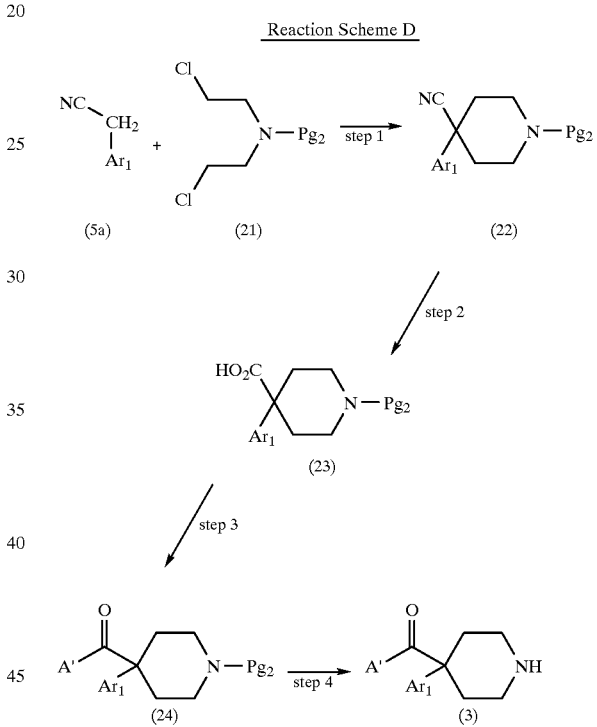

Reaction Scheme D

In Reaction Scheme D, step 1, an appropriate protected bis-(2-chloroethyl)-amine of formula 21 is alkylated with an appropriate aryl-acetonitrile of formula 5a to give a protected 4-aryl-4-cyanopiperidine of of formula 22. An appropriate protected bis-(2-chloroethyl)-amine of formula 21 is one in which the protecting group, $Pg_2$, may be $C_1$–$C_4$ alkyl, benzyl, substituted benzyl, p-toluenesulfonyl, benzenesulfonyl, or a carbamate, such as t-butoxycarbonyl or ethoxycarbonyl. An appropriate aryl-acetonitrile of formula 5a is one $Ar_1$ is as desired in the final product of formula (1). Alkylation of this type are well known and appreciated in the art, some examples of which are found in T. Cammack and P. C. Reeves, *J. Heterocyclic Chem.* 23, 73–75 (1986) and C. V. Bercz and R. D. Ice, *J. Pharmaceutical Sci.*, 21, 1316–1317 (1972) among others.

For example, an appropriate protected bis-(2-chloroethyl)-amine of formula 21 is contacted with an appropriate aryl-acetonitrile of formula 5a. The reaction is carried out in the presence of a base, such as sodium amide, sodium hydride, sodium hexamethyldisilazide, potassium t-butoxide, and lithium diisopropylamide. The reaction is carried out in a solvent, such as dimethyl sulfoxide and tetrahydrofuran. The reaction can be carried out in the presence of 0.01 to 0,5 molar equivalents of a suitable catalyst, such as sodium iodide or potassium iodide. The reaction is generally carried out at temperatures of from 0° C. to 80° C. Generally, the reactions require 1 to 72 hours. The product can be isolated and purified by techniques well known in the art, such as extraction, evaporation, trituration, chromatography, and recrystallization.

Alternately, for example, an appropriate protected bis-(2-chloroethyl)-amine of formula 21 is contacted with an appropriate aryl-acetonitrile of formula 5a under phase transfer conditions. The reaction may be carried out in water or in a solvent system consisting of an organic phase and an aqueous phaseb. The reaction is carried out in the presence of a hydroxide base, such as sodium hydroxide or potassium hydroxide. The reaction is carried out in the presence of a suitable catalyst including quaternary ammonium and phosphonium salts, such as tetrabutylammonium bromide, tetrabutylammonium hydrogen sulfate, hexadecyltributyl phosphonium bromide, benzyltrimethylammonium chloride, and the like. The reaction is vigorously stirred and is generally carried out at temperatures of between 0° C. and 100° C. Generally, the reactions require 1 to 24 hours. The product can be isolated and purified by techniques well known in the art, such as extractions evaporations trituration, chromatography, and recrystallization.

In Reaction Scheme D, step 2, a 4-aryl-4-cyanopiperidine of formula 22 is hydrolyzed to a 4-aryl-piperidine-4-carboxylic acid of formula 23. The hydrolysis of nitriles to acids may be carried out under acidic or basic conditions as is well known and appreciated in the art. The selection and use of hydrolysis conditions which are compatible with the protecting group, $Pg_2$, is well known and appreciated in the art.

As appreciated by those skilled in the art, the removal of the amine protecting group $Pg_2$ in either before or after step 2 may be required. For example, when $Pg_2$ is benzyl the protecting group may be removed to facilitate the hydrolysis of the nitrile and then reintroduced after hydrolysis. If removed, reintroduction of the protecting group $Pg_2$, either as benzyl or another protecting group, after hydrolysis gives a 4-aryl-piperidine-4-carboxylic acid of formula 23. Alternately, the protecting group used in Reaction Scheme D, steps 1 and 2, may be removed and replaced by another protecting group to facilitate deprotection of compound 24, in Reaction Scheme D, step 4. The introduction of amine protecting groups is well known and appreciated in the art and taught in *Protecting Groups in Organic Synthesis* by T. Greene, Wiley-Interscience (1981).

In Reaction Scheme D, step 3, the 4-aryl-piperidine-4-carboxylic ester of formula 23 undergoes an amidation reaction with an appropriate carboxy substituted cyclic amine to give a protected 4-aryl-4-carboxamido-piperidine of formula 24. An appropriate carboxy substituted cyclic amine is one that gives the group A' which is the group A as desired in the final product of formula (1) or gives rise after deprotection or functionalization to a group A as desired in the final product of formula (1). Illustrative examples of such appropriate carboxy substituted cyclic amines include, 4-carboethoxypiperidine, 3-carboethoxypiperidine, 2-carboethoxypiperidine, 4-carbomethoxypiperidine, 3-carbomethoxypiperidine, 2-carbomethoxypiperidine, 4-carbo-n-propyloxypiperidine, 4-carbo-t-butyloxypiperidine, 3-carboethoxypyrrolidine, 2-carboethoxypyrrolidine, 3-carbomethoxypyrrolidine, 2-carbomethoxypyrrolidine, 4-carbomethoxymethylpiperazine, 2-carboethoxymorpholine, 3-carboethoxymorpholine, 4-carboethoxymethyl piperazine, 4-carbo-n-propyloxymethylpiperazine, 4-carboisopropyloxymethylpiperazine, 4-carbo-n-butyloxymethyl piperazine, 4-carbo-t-butyloxymethylpiperazine, 4-phenyl-4-((4-carboethoxyethylpiperazin-1-yl)carboxamido)piperidine, 4-phenyl-4-((4-carboethoxypropylpiperazin-1-yl)) carboxamido)piperidine, 4-phenyl-4-((4-carbo (ethoxycarbonyloxymethoxy) methylpiperazin-1-yl) carboxamido)piperidine, 4-phenyl-4-((4-carbo(t-butylcarbonyloxymethoxy) methylpiperazin-1-yl) carboxamido)piperidine, 4-phenyl-4-((4-carbo (methylcarbonyloxymethoxy)methylpiperazin-1-yl) carboxamido)piperidine, 4-phenyl-4-((4-carbo (propylcarbonyloxymethoxy)methylpiperazin-1-yl) carboxamido)piperidine, 4-carbo-(5-methyl-2-oxo-1,3-dioxol-4-ylmethoxy)methylpiperazine, 4-carbo-(carbo-(2-(trimethylsiilyl)ethoxy)methyloxy)methylpiperazine, and the like. As is appreciated by those skilled in the art, the carboxy function of an appropriate carboxy substituted cyclic amine can be further deprotected or functionalized after deprotection as desired to give A as desired in the final compound of formula (1). Such deprotection or functionalization includes amidation, hydrolysis of esters, formation of esters, and transesterification.

An amidation reaction may proceed through the acid of formula 23 or the acid function of a compound of formula 23 may be first converted to an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; an activated ester, such as phenol ester, p-nitrophenol ester, 2,4-dinitrophenol ester, pentafluorophenol esters N-hydroxysuccinimide ester, N-hydroxyphthalimide ester, 1-hydroxybenztriazole ester, and the like; activated amide, such as imidazole, dimethylpyrazole, triazole, or tetrazole; or the intermediate formed in the presence of coupling agents, such as dicyclohexylcarbodiimide or 1-(3-dimethylaminopropyl)-3-ethylcarbodiimideb. Activated intermediates may be prepared and used directly, or are prepared and isolated before the addition of an appropriate carboxy substituted cyclic amine. Alternately, activated intermediates may be prepared isolated and purified before the addition of an appropriate carboxy substituted cyclic amine. The use and formation of activated intermediates is well known and appreciated in the art.

For example, an acid compound of formula 23 is contacted with a slight molar excess of an appropriate carboxy substituted cyclic amine or a salt of an appropriate carboxy substituted cyclic amine and 1-hydroxybenzotriazole hydrate in the presence of a slight molar excess of a coupling agent, such as dicyclohexylcarbodiimide or 1-(3-dimethyaminopropyl)-3-ethylcarbodiimideb. The reaction is carried out in the presence of a suitable base, such as N,N-diisopropylethylamine, N-methylmorpholine, or triethylamine, and if the salt of an appropriate carboxy substituted cyclic amine is used an about an additional molar amount of a suitable base is added. The reaction is carried out in a suitable solvent, such as dichloromethane, chloroform, or dimethylformamide. The product can be isolated and purified by techniques well known in the art, such as extraction, evaporation, chromatography, and recrystallization.

Alternatively, for example, an acid of formula 23 is contacted with 1.2 to 1.7 equivalents of a suitable base, such as N-methylmorpholine, in a suitable solvent, such as tetrahydrofuran. As above, if the salt of an appropriate carboxy substituted cyclic amine is used an about an additional molar amount of a suitable base is added. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between −50° C. and 0° C. an appropriate carboxy substituted cyclic amine is added. The reaction may, after the addition of amine is complete, be warmed to room temperature. Generally, the reaction requires from 2 to 48 hours. The product can be isolated and purified by techniques well known in the art, such as extraction, evaporation, chromatography, and recrystallization.

In Reaction Scheme D, step 4, a protected 4-aryl-4-carboxamido-piperidine of formula 24 is deprotected to give a piperidine of formula 3. The removal of amine protecting groups is well known and appreciated in the art and is described in *Protecting Groups in Organic Synthesis* by T. Greene, Wiley-Interscience (1981).

In addition, as is readily understood by those skilled in the art, 4-aryl-piperidine-4-carboxylic acid of formula 23 can be prepared from 4-aryl-4-cyanopiperidine of formula 22 further hydrolysis of a 4-aryl-piperidine-4-carboxylic acid amide prepared by hydrolysis of a 4-aryl-4-cyanopiperidine of formula 22.

For example, an appropriate a 4-aryl-4-cyanopiperidine of formula 22 is contacted with basic hydrogen peroxide to give a 4-aryl-4-carboxylic acid amide-piperidine or 4-aryl-4-carboxylic acid amide-piperidine N-oxide. The use of basic hydrogen peroxide for the hydrolysis of nitrites to carboxamides is well know and appreciated in the art. *Reagents for Organic Synthesis*, Fieser and Fieser, John Wiley and Sons, Inc. (1967). Alkali metal hydroxides, such as sodium hydroxide or potassium hydroxide are suitable bases for this reaction. The reaction is carried out in a suitable solvent, such as water, ethanol, methanol, water/ethanol mixtures, or water/methanol mixtures. The reaction is carried out at temperatures of from 0° C. to the refluxing temperature of the suitable solvent. Generally, the reaction requires from about 4 hours to 4 days. The product can be isolated and purified by techniques well known in the art, such as extraction, evaporation, trituration, chromatography, and recrystallization.

When a 4-aryl-4-carboxylic acid amide-piperidine is obtained it is deprotected to give a 4-aryl-piperidine-4-carboxylic acid amideb. When a 4-aryl-4-carboxylic acid amide-piperidine N-oxide is obtained it is reduced and deprotected to give a 4-aryl-piperidine-4-carboxylic acid amideb. It is understood that the amine deprotection and amine oxide reduction may be carried out at the same time or may be carried out sequentially. The reduction of amine oxides is also well known in the art. After reduction of the N-oxide the amine protecting group, $Pg_2$, is removed. The removal of amine protecting groups, such as benzyl and substituted benzyl is well known and appreciated in the art and is described in *Protecting Groups in Organic Synthesis* by T. Greene, Wiley-Interscience (1981). The product can be isolated and purified by techniques well known in the art, such as filtration, extraction, evaporation, trituration, chromatography, and recrystallization.

As is well appreciated in the art a 4-aryl-piperidine-4-carboxylic acid amide can be further hydrolyzed under acidic or basic conditions to give a 4-aryl-piperidine-4-carboxylic acid of formula 23.

The following examples and preparations present typical syntheses of the compounds of formula (1). These examples are understood to be illustrative only and are not intended to limit the scope of the invention in any way.

PREPARATION 1

4-Phenyl-4-((4-carboethoxypiperidin-1-yl) carboxamido) piperidine hydrochloric acid salt Combine 4-phenylpiperidine-4-carboxylic acid p-toluenesulfonic acid (97.5 g, 0.258 mol), N,N-diisopropylethylamine (55 mL, 0.316 mol), and dimethylformamide (900 mL). Add dropwise, a solution of di-t-butyl dicarbonate (65.0 g, 0.30 mol) in dimethylformamide (300 mL). After 20 hours, dilute the reaction mixture with diethyl ether and extract with three times with water and then with brine. Dry the organic layer over $MgSO_4$, filter, rinse the $MgSO_4$ with dichloromethane. Evaporate in vacuo to give 1-t-butoxycarbonyl-4-phenyl-piperidine-4-carboxylic acid.

Combine 1-t-butoxycarbonyl-4-phenyl-piperidine-4-carboxylic acid (18.7 g, 97.5 mmol), N,N-diisopropylethylamine (34.0 mL, 0.195 mol) in dichloromethane (400 mL). Add 1-hydroxybenzotriazole hydrate (13.2 g, 97.7 mmol) and ethyl isonipecotate (4-carboethoxypiperidine) (14.0 g, 88.8 mmol). Add 1-ethyl-3-(3-dimethylaminopropyl)carbodiimide hydrochloride. After 18 hours, dilute the reaction mixture with dichloromethane and extract twice with water. Dry the organic layer over $MgSO_4$, filter, and evaporate in vacuo to give 1-t-butoxycarbonyl-4-phenyl-4-((4-carboethoxypiperidin-1-yl)carboxamido) piperidine.

Combine 1-t-butoxycarbonyl-4-phenyl-4-((4-carboethoxypiperidin-1-yl)carboxamido)piperidine (25.0 g, 56.6 mmol) and dichloromethane (200 mL). Add a solution of hydrochloric acid in dioxane (50 mL, 4M, 200 mmol). After 3 hours, add diethyl ether (400 mL) and filter to give, after drying the title compound.

Also prepared by the method of Preparation 1 are:
a) 4-phenyl-4-((3-carboethoxypiperidin-1-yl)carboxamido) piperidine hydrochloric acid salt using ethyl nipecotate (3-carboethoxypiperidine);
b) 4-phenyl-4-((2-carbomethoxypyrrolidin-1-yl) carboxamido)piperidine hydrochloric acid salt using DL-proline methyl ester hydrochloride (2-carbomethoxypyrrolidine hydrochloride);
c) 4-phenyl-4-((2-carboethoxypiperidin-1-yl)carboxamido) piperidine hydrochloric acid salt using ethyl pipecolinate (2-carboethoxypiperidine).
d) 4-phenyl-4-((2-carboethoxymorpholin-4-yl) carboxamido) piperidine hydrochloric acid salt using 2-carboethoxymorpholine.

EXAMPLE 1

1-(3,4,5-Trimethoxybenzoyl)-3-(2-(4-phenyl-4-((4-carboxypiperidin-1-yl)carboxamido)piperidin-1-yl)ethyl)-3-(3,4-dimethoxyphenyl)pyrrolidine

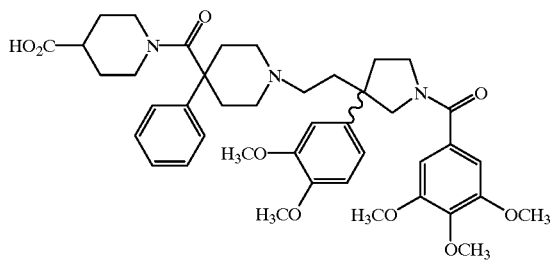

1.1 Synthesis of 3-cyano-3-(3,4-dimethoxyphenyl)pentanedioic diethyl ester

Combine 3,4-dimethoxyphenylacetonitrile (20 g, 113 mmol) and anhydrous tetrahydrofuran (100 mL). Cool in a dry-ice/acetone bath. Add dropwise a solution of sodium bis(trimethylsilyl)amide (226 mL, 1M in tetrahydrofuran, 226 mmol). When the addition is complete warm the reaction mixture to 10° C. and allow to stir for 15 minutes. Cool in a dry-ice/acetone bath, add dropwise ethyl bromoacetate (37.7 g, 226 mmol). When the addition of ethyl bromoacetate is complete, warm the reaction mixture to ambient temperature. After 18 hours, partition the reaction mixture between diethyl ether and water. Extract the organic layer with water and saturated aqueous solution of ammonium chlorides Separate the organic layer, dry over $MgSO_4$, filter, and concentrate in vacuo to obtain a residue. Chromatograph the residue on silica gel eluting with 33% ethyl acetate/hexane. Remove residual solvent in vacuo at 82° C. to give the title compound: $R_f$=0.37 (silica gel, 33% ethyl acetate/hexane). Elemental Analysis calculated for $C_{18}H_{23}NO_6$: C 61.88; H 6.64; N 4.01; Found: C 61.79; H 6.62; N 3.91.

1.2 Synthesis of (3-(3,4-dimethoxyphenyl)-5-oxopyrrolidin-3-yl)acetic acid ethyl ester Combine 3-cyano-3-(3,4-dimethoxyphenyl)pentanedioic diethyl ester (1.3 g, 3.24 mmol) and cobalt(II)chloride hexahydrate (1.54 g, 6.48 mmol) in methanol (50 mL). While maintaining the temperature at or below 20° C. with an ice-bathe add portionwise sodium borohydride (2.17 g, 57 mmol). After the addition is complete, allow the reaction mixture to stand at ambient temperature for 18 hours. Evaporate the reaction mixture in vacuo to obtain a residue. Partition the residue between dichloromethane and 1M hydrochloric acid solution. Extract the aqueous layer several times with dichloromethane, combine the organic layers, dry over $Na_2SO_4$, filter, and concentrate in vacuo to obtain a residue. Chromatograph the residue on silica gel eluting with 20/1 ethyl acetate/methanolo Remove residual solvent in vacuo at 82° C. to give the title compound: $R_f$=0.74 (silica gel, 5/1 ethyl acetate/methanol); mp; 116–118° C. Elemental Analysis calculated for $C_{16}H_{21}NO_5$: C 62.53; H 6.89; N 4.56; Found: C 62.52; H 6.85; N 4.50.

1.3 Synthesis of 3-(3,4-dimethoxyphenyl)-3-(2-hydroxyethyl pyrrolidine

Combine lithium aluminum hydride (0.99 g, 26.0 mmol) and anhydrous tetrahydrofuran (20 mL). Slowly, add (3-(3,4-dimethoxyphenyl)-5-oxopyrrolidin-3-yl)acetic acid ethyl ester (2.0 g, 6.5 mmol) as a solution in anhydrous tetrahydrofuran (40 mL). After the addition is complete. heat to reflux. After 18 hours, cool in an ice-bath. Add water (1 mL) dropwise at such a rate that the temperature of the reaction mixture does not rise above 20° C. Cool to 10° C., add 15% sodium hydroxide solution (1.0 mL). Add water (3 mL). After 15 minutes, filter the reaction mixture and concentrate the filtrate in vacuo to give the title compound: $R_f$=0.68 (silica gel, 5/1 ethyl acetate/methanol).

Prepare an analytical sample as follows: Combine 3-(3,4-dimethoxyphenyl)-3-(2-hydroxyethyl)pyrrolidine (0.51 g, 2.02 mmol) and oxalic acid (0.18 g, 2.00 mmol) in tetrahydrofuran (70 mL). After 18 hours, filter and dry. Triturate with diethyl ether (100 mL), filter and dry in vacuo at 81° C. to give the title compound as its oxalate salt: mp; 140–142° C. Elemental Analysis calculated for $C_{14}H_{21}NO_3 \cdot C_2H_2O_4$: C 56.30; H 6.79; N 4.10; Found: C 56.15; H 6.76; N 4.13.

1.4.1 Synthesis of 1-(3,4,5-trimethoxybenzoyl)-3-(3,4-dimethoxyphenyl)-3-(2-hydroxyethyl)pyrrolidine Combine 3-(3,4-dimethoxyphenyl)-3-(2-hydroxyethyl)pyrrolidine (2.27 g, 9.03 mmol) and N-methylmorpholine (2.48 mL, 22.6 mmol) in anhydrous dichloromethane (100 mL). Cool the reaction mixture to −5° C. with an salt-ice bath. Slowly, add 3,4,5-trimethoxybenzoyl chloride (2.2 g, 9.5 mmol) as a solution in dichloromethane (30 mL). Warm to ambient temperature. After 18 hours, extract the reaction mixture with a saturated solution of potassium carbonate. Dry the organic layer over $Na_2SO_4$, filter, and concentrate in vacuo to obtain a residue. Chromatograph the residue on silica gel eluting with 95% dichloromethane/methanol to obtain a residue. Combine the residue and dichloromethane (100 mL), and extract 3 times with 1M hydrochloric acid solution and saturated solution of potassium carbonate. Dry the organic layer over $Na_2SO_4$, filter, and concentrate in vacuo to obtain a residue. Chromatograph the residue on silica gel eluting with 20/1 ethyl acetate/methanol to obtain an oil $R_f$=0.14 (silica gel, 20/1 ethyl acetate/methanol). Dry in vacuo at 110° C. to obtain the title compound as a glass: mp; 60–62° C. Elemental Analysis calculated for $C_{24}H_{31}NO_7$: C 64.70; H 7.01; N 3.14; Found C 64.40; H 7.21; N 2.85.

1.4.2 Synthesis of 1-(3,4,5-trimethoxybenzoyl)-3-(3,4-dimethoxyphenyl)-3-(2-hydroxyethyl)pyrrolidine Combine 3-(3,4-dimethoxyphenyl)-3-(2-hydroxyethyl)pyrrolidine (5.34 g, 212 mmol) and sodium carbonate (124 g, 11.7 mmol) in ethyl acetate/water (4/1) (120 mL). Cool the reaction mixture to −5° C. with an salt-ice bathe Slowly, add 3,4,5-trimethoxybenzoyl chloride (5.14 g, 22.3 mmol) as a solution in ethyl acetate (60 mL) at a rate such that the temperature of the reaction mixture does not rise above 0° C. Maintain the reaction temperature at about 0° C. After 18 hours, separate the organic layer. Extract the organic layer twice with 1M aqueous hydrochloric acid solution, saturated solution of sodium bicarbonate, water and a saturated solution of sodium chloride. Dry the organic layer over $Na_2SO_4$, filter, and concentrate in vacuo to obtain a residue. Combine the aqueous layers and neutralize with a saturated solution of sodium bicarbonate. Extract the neutralized aqueous layers with dichloromethane. Dry the organic layer over $Na_2SO_4$, filtered and concentrate in vacuo to obtain another residue. Combine the residues and chromatograph on silica gel eluting with 10/1 dichloromethane/methanol to obtain a residue. Combine the residue and dichloromethane (100 mL), and extract 3 times with 1M hydrochloric acid solution and saturated solution of potassium carbonate. Dry the organic layer over $Na_2SO_4$, filter, and concentrate in vacuo to obtain the title compound: $R_f$=0.23 (silica gel, 10/1 ethyl acetate/methanol).

1.5 Synthesis of 1-(3,4,5-trimethoxybenzoyl)-3-(3,4-dimethoxyphenyl)-3-(2-methanesulfonyloxyethyl)pyrrolidine Combine 1-(3,4,5-trimethoxybenzoyl)-3-(3,4-dimethoxyphenyl)-3-(2-hydroxyethyl)pyrrolidine (0.43 g, 0.97 mmol), triethylamine (3.3 mL, 2.4 mmol), and anhydrous dichloromethane (30 mL). Cool the reaction mixture to −5° C. with an salt-ice bath. Slowly, add methanesulfonyl chloride (0.082 mL, 1.06 mmol) at such a rate that the temperature of the reaction mixture does not rise above 2° C. Warm to ambient temperature. After 18 hours, quench the reaction by the addition of iceb. Separate the organic layer and extract 3 times with 1M hydrochloric acid solution and 2 times with a saturated solution of sodium bicarbonate. Dry the organic layer over $Na_2SO_4$, filter, and concentrate in vacuo to obtain the title compound: $R_f$=0.48 (silica gels 20/1 ethyl acetate/methanol).

1.6 Synthesis of 1-(3,4,5-trimethoxybenzoyl)-3-(2-(4-phenyl-4-((4-carboethoxypiperidin-1-yl)carboxamido)piperidin-1-yl)ethyl)-3-(3,4-dimethoxyphenyl)pyrrolidine Combine 1-(3,4,5-trimethoxybenzoyl)-3-(3,4-dimethoxyphenyl)-3-(2-methanesulfonyloxyethyl)pyrrolidine (0.86 g, 164 mmol), 4-phenyl-4-((4-carboethoxypiperidin-1-yl)carboxamido)piperidine hydrochloric acid salt (0.57 g, 1.97 mmol), sodium iodide (0.25 g, 1.64 mmol), and N,N-diisopropylethylamine (0.84 g, 6.6 mmol) in acetonitrile (12 mL). Heat to reflux. After 10 hours, cool and dilute the reaction mixture ethyl acetate. Extract three times with a saturated aqueous ammonium chloride solution, twice with a saturated aqueous sodium bicarbonate solution, and then brine. Dry the organic layer over $Na_2SO_4$, filter, and evaporate in vacuo to give the title compound.

1.7 Synthesis of 1-(3,4,5-trimethoxybenzoyl)-3-(2-(4-phenyl-4-((4-carboxypiperidin-1-yl)carboxamido)piperidin-1-yl)ethyl)-3-(3,4-dimethoxyphenyl)pyrrolidine Combine 1-(3,4,5-trimethoxybenzoyl)-3-(2-(4-phenyl-4-((4-carboethoxypiperidin-1-yl)carboxamido)piperidin-1-yl)ethyl)-3-(3,4-dimethoxyphenyl)pyrrolidine (0.3 g, 0.4 mmol) and lithium hydroxide (60 mgb, 2.4 mmol) in tetrahydrofuran/water (6 mL/6 mL). After 3 hours, concentrate in vacuo to remove most of the tetrahydrofuran and dilute with water. Adjust the pH to about 7 using a 1M aqueous hydrochloric acid solution. Extract three times with dichloromethane, adjusting the pH as needed to maintain pH 7 in the aqueous layer. Dry the organic layer over $MgSO_4$, filter, and evaporate in vacuo to give the title compound.

EXAMPLE 2

1-(3,4,5-Trimethoxybenzoyl)-3-(2-(4-phenyl-4-((3-carboxypiperidin-1-yl)carboxamido)piperidin-1-yl)ethyl)-3-(3,4-dichlorophenyl)pyrrolidine

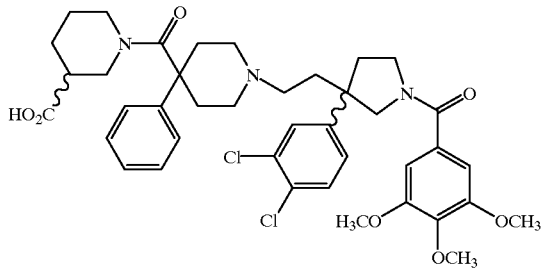

2.1.1 Synthesis of 3-cyano-3-(3,4-dichlorophenyl)pentanedioic acid diethyl ester Prepare by the method of Example 1.1 using 3,4-dichlorophenylacetonitrile (30.0 gg 0.161 mol). Purify by recrystallization from diethyl ether to give the title compound: $R_f$=0.28 (silica gel, 20% ethyl acetate/hexane), mp; 68–69° C. Elemental Analysis calculated for $C_{16}H_{17}Cl_2NO_4$: C 53.65; H 4.76; N 3.91; Found C 53.69; H 4.79; N 3.93.

2.1.2 Synthesis of 3-cyano-3-(3,4-dichlorophenyl)pentanedioic acid diethyl ester Cool a solution of sodium bis(trimethylsilyl)amide (480 lb, 1M in THF) to about −10° C. and stir. Add a solution of 3,4-dichlorophenylacetonitrile in methyl t-butyl ether (34.5% by weight, 125 lb of solution) at such a rate that the temperature of the reaction mixture does not rise above about 10° C. Combine ethyl bromoacetate (94 lb) and methyl t-butyl ether (about 125 lb) and cool to about −18° C. and then add the solution prepared above over 60–90 minutes After the reaction is complete, as determined by chromatography, add water (18 gal). Add a 12M aqueous hydrochloric acid solution until the pH is about 4. If the pH falls below 3, use 20% aqueous sodium hydroxide solution to raise the pH to about 4. Separate the layers and extract the organic layer with brine. Evaporate in vacuo at about 40° C. to give a residue. Combine the residue and isopropanol (about 45 lb) and evaporate in vacuo at about 40° C. to give a residue. Add isopropanol (190 lb), warm to about 35° C., and then cool to about −10° C. to give a solid Collect the solid by filtration, rinse with cold isopropanol, and centrifuge to give the title compound as a wet cake containing isopropanol.

2.2.1 Synthesis of (3-(3,4-dichlorophenyl)-5-oxopyrrolidin-3-yl)acetic acid ethyl ester Prepare by the method of Example 1.2 using 3-cyano-3-(3,4-dichlorophenyl)pentanedioic acid diethyl ester (10 g, 28 mmol). Purify by chromatography on silica gel eluting sequentially with 3% methanol/dichloromethane and then 6% methanol/dichloromethane to give the title compound.

2.2.2 Synthesis of (3-(3,4-dichlorophenyl)-5-oxopyrrolidin-3-yl)acetic acid ethyl ester Combine 3-cyano-3-(3,4-dichlorophenyl)pentanedioic acid diethyl ester (32 g, 89 mmol) and ethanol (150 mL) in a Parr bottleb. Add Raney nickel (100 g) and an aqueous concentrated ammonia solution (40 mL). Hydrogenate at 50 psi for 24 h. Filter through a celite pad and rinse the solids with ethanol. Evaporate the filtrate in vacuo to obtain a residue. Chromatograph the residue on silica gel eluting with 6% methanol/dichloromethane to give the title compound: $R_f$=0.34 (silica gel, 6% methanol/dichloromethane); mp; 87–90° C. Elemental Analysis calculated for $C_{14}H_{15}Cl_2NO_3$: C 53.18; H 4.78; N 4.43; Found: C 53.34; H 4.71; N 4.51.

2.2.3 Synthesis of (3-(3,4-dichlorophenyl)-5-oxopyrrolidin-3-yl)acetic acid ethyl ester Combine Raney nickel (24 lb) and an aqueous concentrated ammonia solution (19 lb). Add a solution of 3-cyano-3-(3,4-dichlorophenyl)pentanedioic acid diethyl ester (15 lb) and ethanol (117 lb) in a pressure reactor. Hydrogenate at 200 psi and 35° C. After 20 hours, cool, vent the vessel, purge with nitrogen, and filter. Rinse the solids with ethanol. Evaporate the filtrate in vacuo to give a residues. Crystallize the residue by dissolving in ethyl acetate and triturate the solution with heptane to give a solid. Collect the solid to give the title compound. Elemental Analysis calculated for $C_{14}H_{15}Cl_2NO_3$: C 53.18; H 4.78; N 4.43; Founds C 53.18; H 4.72; N 4.46.

2.2.4 Synthesis of (3-(3,4-dichlorophenyl)-5-oxopyrrolidin-3-yl)acetic acid ethyl ester Combine 3-cyano-3-(3,4-dichlorophenyl)pentanedioic acid diethyl ester (6.7 kg, wet cake containing isopropanol about 3% L.O.D.) and 3C ethanol (52 kg) in a pressure reactor. Add Raney nickel in water (17.5 kg, about 11 kg of active catalyst) and an aqueous concentrated ammonia solution (8.7 kg). Hydrogenate at 200 psi and 35° C. When the reaction is complete, cool, vent the reactor, and purge with nitrogen. Filter through a filter bag, rinse with ethanol, and then filter through a 0.2 micron cartridge filter, and rinse the solids with ethanol. Evaporate the filtrate in vacuo to give the title compound.

2.2.5 Synthesis of (3-(3,4-dichlorophenyl)-5-oxopyrrolidin-3-yl)acetic acid ethyl ester Combine Raney nickel (twice washed with water and twice washed with ethanol, 3.6 kg), 3-cyano-3-(3,4-dichlorophenyl)pentanedioic acid diethyl ester (1260 g, 3.51 mol), ethanol (9 L), and an aqueous concentrated ammonia solution (1.6 L) in a 5 gallon autoclave Hydrogenate at 55 psi. After 20 hours, vent the vessel, purge with nitrogen, and filters Rinse the solids with ethanol (about 1 L) Evaporate the filtrate in vacuo to give a residue. Combine the residue and ethyl acetate (10 L) and extract twice with water (1 L) and then with brine. Dry the organic layer over $MgSO_4$, filters and concentrate in vacuo to give a residue. Crystallize the residue from ethyl acetate (about 1.8 L) and heptane (about 7.2 L) to give a solid. Collect the solid to give the title compound: mp; 98–99° C.

2.3 Synthesis of (3-(3,4-dichlorophenyl)-3-(2-hydroxyethyl) pyrrolidine

Cool a solution of lithium aluminum hydride (450 mL, 1M in tetrahydrofuran, 450 mmol) to −10° C. in a ice/acetone bath. Add dropwise, a solution of sulfuric acid (12 mL, 99.999%, 225.3 mmol) in tetrahydrofuran (35 mL). (Use caution when adding the sulfuric acid to the tetrahydrofuran and also when adding the sulfuric acid/tetrahydrofuran solution to the lithium aluminum hydride solution). After the addition is complete, stir for 1 hour. Warm to ambient temperature and stir for 2 hours. Add dropwise, a solution of (3-(3,4-dichlorophenyl)-5-oxopyrrolidin-3-yl)acetic acid ethyl ester (23.2 g, 73.4 mmol) in Tetrahydrofuran (70 mL). Heat to 45–50° C. for 36 hours. Cool in an ice bath. Add dropwise, a solution of tetrahydrofuran/water (1/1, 70 mL). Filter and rinse the filter cake with Tetrahydrofuran and dichloromethane, retain the filtrate. Combine the filter cake with tetrahydrofuran/water/15% sodium hydroxide solution (1 L/70 mL/20 mL) and vigorously stir for 2 hours. Filter and combine the filtrate with the filtrate obtained above. Concentrate the combined filtrates in vacuo to obtain a residue. Dissolve the residue in dichloromethane and dry over $MgSO_4$, filter, and concentrate in vacuo to obtain a residue. Recrystallize the residue from diethyl ether to give the title compound: $R_f$=0.27 (silica gel, 9:1:0.2; dichloromethane/methanol/ammonium hydroxide); mp; 91–94° C. Elemental Analysis calculated for $C_{12}H_{15}Cl_2NO$: C 55.40; H 5.81; N 5.38; Found: C 55.64; H 5.88; N 5.20.

2.4 Synthesis of 1-(3,4,5-trimethoxybenzoyl)-(3-(3,4-dichlorophenyl)-3-(2-hydroxyethyl)pyrrolidine Combine 3-(3,4-dichlorophenyl)-3-(2-hydroxyethyl) pyrrolidine (288 mg, 1.1 mmol) and N-methylmorpholine (0.25 mL 2.27 mmol) in dichloromethane (10 mL). Cool to −78° C. in a dry-ice/acetone bath. Add a solution of 3,4,5-trimethoxybenzoyl chloride (250 mg, 1.1 mmol) in dichloromethane (3 mL). Warm the reaction mixture to 0° C. After 1 hour, extract the reaction mixture with 1M hydrochloric acid solution and 5% sodium bicarbonate solution. Dry the organic layer over $MgSO_4$, filter, and concentrate in vacuo to give a residue. Chromatograph the residue on silica gel eluting sequentially with 50% ethyl acetate/hexane and 6% methanol/dichloromethane to give the title compound: $R_f$=0.38 (silica gel, 6% methanol/dichloromethane).

2.5.1 Synthesis of 1-(3,4,5-trimethoxybenzoyl)-(3-(3,4-(dichlorophenyl)-3-(2-methanesulfonyloxyethyl)pyrrolidine Prepare by the method of Example 1.5 using 1-(3,4,5-trimethoxybenzoyl)-3-(3,4-dichlorophenyl)-3-(2-hydroxyethyl)pyrrolidine to give the title compound.

2.5.2 Synthesis of 1-(3,4,5-trimethoxybenzoyl)-3-(3,4-dichlorophenyl)-3-(2-methanesulfonyloxyethyl)pyrrolidine Combine 1-(3,4,5-trimethoxybenzoyl)-3-(3,4-dichlorophenyl)-3-(2-hydroxyethyl)pyrrolidine (200 mg, 0.44 mmol) and N,N-diisopropylethylamine (0.17 mL, 0.97 mmol) in dichloromethane (25 mL). Cool in a ice-bath. Add dropwise, methanesulfonyl chloride (0.066 g, 0.57 mmol). After 2 hours, extract with 1M hydrochloric acid solution and 5% sodium bicarbonate solution. Dry the organic layer over $MgSO_4$, filter, and concentrate in vacuo to give the title compound: $R_f$=0.42 (silica gel, 6% methanol/dichloromethane); mp; 64.0–66.0° C.

2.5.3 Synthesis of 1-(3,4,5-trimethoxybenzoyl)-3-(3,4-dichlorophenyl)-3-(2-methanesulfonyloxyethyl)pyrrolidine Combine 1-(3,4,5-trimethoxybenzoyl)-3-(3,4-dichlorophenyl)-3-(2-hydroxyethyl)pyrrolidine (200 mg, 0.44 mmol) and N-methylmorpholine (0.97 mmol) in toluene (10 mL). Add dropwise, methanesulfonyl chloride (0.066 g, 0.57 mmol). After 12 hours, dilute with toluene (20 mL) and extract with 1M hydrochloric acid solution and 5% sodium bicarbonate solution. Dry the organic layer over $MgSO_4$, filter, and concentrate in vacuo to give the title compound.

2.6 Synthesis of 1-(3,4,5-trimethoxybenzoyl)-3-(2-(4-phenyl-4-((3-carboethoxypiperidin-1-yl)carboxamido) piperidin-1-yl)ethyl)-3-(3,4-dichlorophenyl)pyrrolidine Prepare by the method of Example 1.6 using 1-(3,4,5-trimethoxybenzoyl)-3-(3,4-dichlorophenyl)-3-(2-methanesulfonyloxyethyl)pyrrolidine and 4-phenyl-4-((3-carboethoxypiperidin-1-yl)carboxamido) piperidine hydrochloric acid salt to give the title compound.

2.7 Synthesis of 1-(3,4,5-trimethoxybenzoyl)-3-(2-(4-phenyl-4-((3-carboxypiperidin-1-yl)carboxamido)piperidin-1-yl)ethyl)-3-(3,4-dichlorophenyl)pyrrolidine Prepare by the method of Example 1.7 1-(3,4,5-trimethoxybenzoyl)-3-(2-(4-phenyl-4-((3-carboethoxypiperidin-1-yl)carboxamido)piperidin-1-yl) ethyl)-3-(3,4-dichlorophenyl)pyrrolidine to give the title compound.

EXAMPLE 3

1-(3,4,5-Trimethoxybenzoyl)-3-(2-(4-phenyl-4-((2-carboxypiperidin-1-yl)carboxamido)piperidin-1-yl) ethyl)-3-phenylpyrrolidine

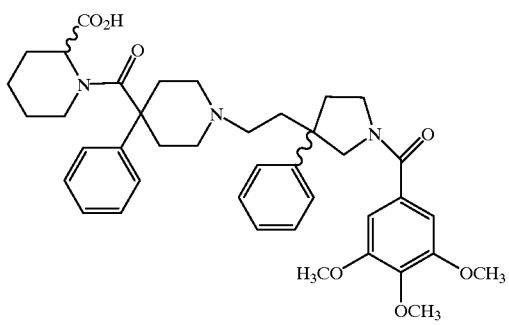

3.1.1 Synthesis of 3-cyano-3-phenylpentanedioic acid diethyl ester

Prepare by the method of Example 1.1 using phenylacetonitrile (5.85 g, 50.0 mmol). Purify by chromatography on silica gel eluting with 20% ethyl acetate in hexane to obtain the title compound: $R_f$=0.23 (silica gel, 20% ethyl acetate in hexane).

3.1.2 Synthesis of 3-cyano-3-phenylpentanedioic acid diethyl ester

Combine phenylacetonitrile (5.85 g, 50.0 mmol) and tetrahydrofuran (140 mL). Cool to about 5° C. Add dropwise, a solution of sodium bis(trimethylsilyl)amide (800 mL, 1M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above about 20° C. Allow to stir at ambient temperature. After 18 hours, dilute with diethyl ether (15 L) and extract with saturated aqueous solution of ammonium chloride, then waters and then saturated aqueous solution of sodium chloride. Dry the organic layer over $MgSO_4$, filter, and concentrate in vacuo to obtain a residue. Distill the residue by bulb-to-bulb distillation to give the title compound: bp; 140–150° C. at 0.2 mm Hg.

3.1.3 Synthesis of 3-cyano-3-phenylpentanedioic acid diethyl ester

Combine phenylacetonitrile (175.5 g, 1.5 mol) and tetrahydrofuran (1.95 L). Cool to about 0° C. Add dropwise over about 15 minutes, a solution of sodium bis (trimethylsilyl)amide (3.2 L, 1M in tetrahydrofuran, 3.2 mol). When the addition is complete, warm the reaction mixture to ambient temperature and allow to stir for 1 hour. Transfer the above solution over about 45 minutes into a cooled (about −20° C.) solution of ethyl bromoacetate (510 g, 3.05 mol) in tetrahydrofuran (1.95 L). Warm to ambient temperature and allow to stir. After 18 hours, dilute with diethyl ether (3 L) and water (1.5 L). Extract twice with saturated aqueous solution of ammonium chloride (2.25 L) and then brine. Dry the organic layer over $MgSO_4$, filter, and concentrate in vacuo to obtain a residue. Distill the residue by bulb-to-bulb distillation to give the title compound: bp; 180–190° C. at 30 mm of Hg. Elemental Analysis calculated for $C_{16}H_{19}NO_4$: C, 66.43; H, 6.62; N, 4.84. Found C, 66.34; H, 6.57; N 4.82.

3.2.1 Synthesis of (3-phenyl-5-oxopyrrolidin-3-yl)acetic acid ethyl ester

Prepared by the method of Example 2.2.2 using 3-cyano-3-phenylpentanedioic acid diethyl ester to give the title compound: $R_f$=0.60 (silica gel, 6% methanol/dichloromethane).

3.2.2 Synthesis of (3-phenyl-5-oxopyrrolidin-3-yl)acetic acid ethyl ester

Combine 3-cyano-3-phenylpentanedioic acid diethyl ester (93 g, 321 mmol) and ethanol (400 mL) in a 2 gallon pressure reactor. Add Raney nickel (280 g). Heat to 50° C. and charge with 200 psi of hydrogenb. After 15 minutes, vent the reactor and add aqueous concentrated ammonia solution (120 mL). Charge the reactor with 200 psi of hydrogenb. After 7 hours, vent the reactor and allow to stand for 18 hours. Filter through a celite pad and rinse the solids with ethanol. Evaporate the filtrate in vacuo to obtain a residue. Combine the residue and 1/5 diethyl ether/hexane (500 mL) and cool to −20° C. After 18 hours, decant and add 1/5 diethyl ether/hexane (500 mL) and cool to −20° C. to give a solid. Collect the solid by filtration and triturate with 1/5 diethyl ether/hexane (500 mL). Filter and dissolve in diethyl ether (300 mL) and add hexane (700 mL) to give a solid. Collect the solid by filtration and dry to give the title compound. Elemental Analysis calculated for $C_{14}H_{17}NO_3$: C 68.00; H 6.93; N 5.66; Found: C 67.63; H 6.99; N 5.81.

3.2.3 Synthesis of (3-phenyl-5-oxopyrrolidin-3-yl)acetic acid ethyl ester

Combine 3-cyano-3-phenylpentanedioic acid diethyl ester (396.6 g, 137 mol) and ethanol (4 L), and concentrated aqueous ammonia (530 mL), in a two gallon autoclave. Add Raney nickel (410 g). Heat to 24° C. and charge with 205 psi of hydrogenb. After 26 hours, vent the reactor and purge with nitrogen. Filter the reaction mixture through a celite pad and rinse the solids with ethanol (1.5 L). Evaporate the filtrate in vacuo to give the title compound.

3.2.4 Synthesis of (3-phenyl-5-oxopyrrolidin-3-yl)acetic acid ethyl ester

Combine 3-cyano-3-phenylpentanedioic acid diethyl ester (243 g, 0.84 mol) and ethanol (2.5 L), concentrated aqueous ammonia (325 mL), and Raney nickel (250 g, prewashed three times with water) in a two gallon autoclave. Charge with 200 psi of hydrogenb. Heat to 50° C. After 24 hours, vent the reactor and purge with nitrogen. Filter the reaction mixture through a celite pad and rinse the solids with ethanol (1 L). Evaporate the filtrate in vacuo to give the title compounds.

3.3.1 Synthesis of 3-phenyl-3-(2-hydroxyethyl)pyrrolidine

Prepare by the method of Example 13 using (3-phenyl-5-oxopyrrolidin-3-yl)acetic acid ethyl ester (8.7 g, 35 mmol) to give, after recrystallization from dichloromethane/diethyl ether, the title compound: mp; 115.0–117.0° C.; $R_f$=0.03 (silica gel, 6% methanol/dichloromethane). Elemental Analysis calculated for $C_{12}H_{17}NO$: C 75.36; H 8.96; N 7.32; Found: C 75.78; H 8.96; N 7.45.

3.3.2 Synthesis of 3-phenyl-3-(2-hydroxyethyl)pyrrolidine

Combine (3-phenyl-5-oxopyrrolidin-3-yl)acetic acid ethyl ester (301 g, 1.25 mol) and tetrahydrofuran (3.5 L). Cool to about 5° C. Slowly, add portionwise over about 45 minutes a solution of lithium aluminum hydride in tetrahydrofuran (3.9 L, 1M, 3.9 mol). After the addition is complete heat to 60° C. After 18 hours, cool in an ice-bath. Add water/tetrahydrofuran 1/1 (1.95 L) dropwise at such a rate that the temperature of the reaction mixture does not rise above 20° C. Dilute the reaction mixture with tetrahydrofuran (2.25 L) and stir. After 1.5 hours, filter the reaction mixture. Suspend the solids in diethyl ether (3 L) and filter. Combine the filtrates and concentrate the in vacuo to give a residue. Combine the residue and dichloromethane (4 L) and extract three times with water (1 L). Dry the organic layer over $NgSO_4$, filter, and concentrate in vacuo to obtain a solid. Triturate the solid with diethyl ether (0.3 L), collect by filtration, rinse with diethyl ether, and dry to give the title compound: $R_f$=0.12 (silica gel dichloromethane/methanol/concentrated aqueous ammonia, 9/1/0.1).

3.3.3 Synthesis of 3-phenyl-3-(2-hydroxyethyl)pyrrolidine

Combine (3-phenyl-5-oxopyrrolidin-3-yl)acetic acid ethyl ester (171 g, 0.69 mol) and tetrahydrofuran (2 L). Cool to about 5° C. Slowly, add over about 15 minutes a solution of lithium aluminum hydride in tetrahydrofuran (2.24 L, 1M, 2.24 mol). After the addition is complete heat to about 60° C. After 18 hours, cool in an ice-bath. Slowly quench by adding a saturated aqueous solution of sodium potassium tartrate (208 mL). After the quench is complete, add $Na_2SO_4$ (100 g) and celite (150 g) and stir. After 3 hours, dilute the reaction mixture with tetrahydrofuran (2 L) and filter. Suspend the solids in diethyl ether (2 L) and and filter. Combine the filtrates and concentrate the in vacuo to give the title compound: mp; 106–110° C. $R_f$=0.12 (silica gel dichloromethane/methanol/concentrated aqueous ammonia, 9/1/0.1).

3.4.1 Synthesis of 1-(3,4,5-trimethoxybenzoyl)-3-phenyl-3-(2-hydroxyethyl)pyrrolidine Prepared by the method of Example 14.1 using 3-phenyl-3-(2-hydroxyethyl)pyrrolidine to give the title compound: $R_f$=0.38 (silica gel, 6% methanol/dichloromethane).

3.4.2 Synthesis of 1-(3,4,5-trimethoxybenzoyl)-3-phenyl-3-(2-hydroxyethyl)pyrrolidine Prepared by the method of Example 14.2 using 3-phenyl-3-(2-hydroxyethyl)pyrrolidine to give the title compound: $R_f$=0.05 (silica gel, ethyl acetate).

3.5 Synthesis of 1-(3,4,5-trimethoxybenzoyl)-3-phenyl-3-(2-methanesulfonyloxyethyl)pyrrolidine Combine 1-(3,4,5-trimethoxybenzoyl)-3-phenyl-3-(2-hydroxyethyl)pyrrolidine (0.5 g, 1.3 mmol), N,N-diisopropylethylamine (0.5 mL, 2.9 mmol), and anhydrous dichloromethane (17 mL). Cool to 0° C. using an ice bath. Add methanesulfonyl chloride (201 mg, 1.36 mmol). After 2 hours, dilute the reaction mixture with dichloromethane and extract with a saturated solution of sodium bicarbonate. Dry the organic layer over $Na_2SO_4$, filter, and concentrate in vacuo to give the title compound: $R_f$=0.26 (silica gel, ethyl acetate).

3.6 Synthesis of 1-(3,4,5-trimethoxybenzoyl)-3-(2-(4-phenyl-4-((2-carboethoxypiperidin-1-yl)carboxamido)piperidin-1-yl)ethyl)-3-phenylpyrrolidine Prepare by the method of Example 1.6 using 1-(3,4,5-trimethoxybenzoyl)-3-phenyl-3-(2-methanesulfonyloxyethyl)pyrrolidine and 4-phenyl-4-((2-carboethoxypiperidin-1-yl)carboxamido)piperidine hydrochloric acid salt to give the title compound.

3.7 Synthesis of 1-(3,4,5-trimethoxybenzoyl)-3-(2-(4-phenyl-4-((2-carboxypiperidin-1-yl)carboxamido)piperidin-1-yl)ethyl)-3-phenylpyrrolidine Prepare by the method of Example 1.7 1-(3,4,5-trimethoxybenzoyl)-3-(2-(4-phenyl-4-((2-carboethoxypiperidin-1-yl)carboxamido)piperidin-1-yl)ethyl)-3-phenylpyrrolidine to give the title compound.

EXAMPLE 4

1-(3,4,5-Trimethoxybenzoyl)-3-(2-(4-phenyl-4-((2-carboxypyrrolidin-1-yl)carboxamido)piperidin-1-yl)ethyl)-3-(3,4-dichlorophenyl)pyrrolidine

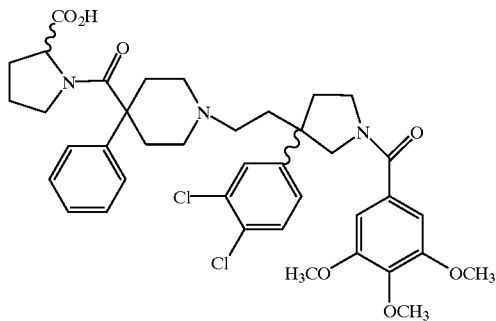

4.1 Synthesis of 1-(3,4,5-trimethoxybenzoyl)-3-(2-(4-phenyl-4-((2-carbomethoxypyrrolidin-1-yl)carboxamido)piperidin-1-yl)ethyl)-3-(3,4-dichlorophenyl)pyrrolidine Prepare by the method of Example 1.6 using 1-(3,4,5-trimethoxybenzoyl)-3-(3,4-dichlorophenyl)-3-(2-methanesulfonyloxyethyl)pyrrolidine and 4-phenyl-4-((2-carbomethoxypyrrolidin-1-yl)carboxamido) piperidine hydrochloric acid salt to give the title compound.

4.2 Synthesis of 1-(3,4,5-trimethoxybenzoyl)-3-(2-(4-phenyl-4-((2-carboxypyrrolidin-1-yl)carboxamido)piperidin-1-yl)ethyl)-3-(3,4-dichlorophenyl)pyrrolidine Prepare by the method of Example 1.7 using 1-(3,4,5-trimethoxybenzoyl)-3-(2-(4-phenyl-4-((2-carbomethoxypyrrolidin-1-yl)carboxamido)piperidin-1-yl)ethyl)-3-(3,4-dichlorophenyl)pyrrolidine to give the title compound.

PREPARATION 2

4-(Pyrid-3-yl)-4-((4-carboethoxymethylpiperazin-1-yl)carboxamido)piperidine

Combine N-benzyl-N-bis-(2-chloroethyl)amine hydrochloride (72.0 g, 269 mmol) and pyrid-3-ylacetonitrile (31.8 g, 269 mmol) and hexadecyltributylphosphonium bromide (6 g) in aqueous solution of sodium hydroxide (50% by weights 400 mL). Heat on a steam bath and stir vigorously. After 1.5 hours, cool the reaction mixture to ambient temperature. Extract the reaction mixture three times with dichloromethane. Combine the organic layers and extract twice with an aqueous 10% hydrochloric acid solution. Combine the aqueous layers and make basic with an aqueous solution of sodium hydroxide (50% by weight). Extract the basified aqueous layer three times with diethyl ether. Dry the combined ether layers over $MgSO_4$ and filter to give a filtrate. Purge the filtrate with hydrogen chloride (gas) to give a solid. Collect the solid by filtration and dry in vacuo at 65° C. to give 1-benzyl-4-(pyrid-3-yl)-4-cyanopiperidine hydrochloric acid salt.

Combine 1-benzyl-4-(pyrid-3-yl)-4-cyanopiperidine hydrochloric acid salt (10.0 g, 28 mmol), sodium hydroxide (7.6 g, 190 mmol), and water (2 mL) in ethylene glycol (120 mL). Heat to reflux. After 15 hours, evaporate in vacuo to give a residue. Combine the residue with methanol (20 mL) and ethanol (20 mL) and stir to give a solid. Filter to remove the solid. Add ethanol (50 mL) to the filtrate and stir for 1 hour to give a second solid. Remove the second solid by filtration and acidify the filtrate with aqueous 12M hydrochloric acid solution. Evaporate the acidified filtrate in vacuo to give a residue. Combine the residue and dichloromethane. Extract with water. Adjust the pH of the aqueous layer to 7 using sodium bicarbonate. Evaporate the aqueous layer in vacuo to give a residues combine the residue and ethanol and again evaporate in vacuo to give a residue. Combine the residue with methanol and heat to about 50° C. to give a slurryb. Filter the slurry add acetone (30 mL) to the filtrate to give a solid. Collect the solid by filtration, rinse with acetone, and dry to give 1-benzyl-4-(pyrid-3-yl)-piperidine-4-carboxylic acid.

Combine 1-benzyl-4-(pyrid-3-yl)-piperidine-4-carboxylic acid (5.1 g), 4-carboethoxymethylpiperazine (5.8 g), 1-(3-dimethylaminopropyl)-3-ethylcarbodiimide hydrochloride (5.0 g), and 1-hydroxybenzotriazole hydrate (3.6 g) in dimethylformamide (130 mL). After 60 hours, dilute the reaction mixture with ethyl acetate (1 L). Extract the diluted reaction mixture with a saturated aqueous solution of sodium bicarbonate. Dry the organic layer over $MgSO_4$, filter, and evaporate in vacuo to give a residue. Triturate the residue with diethyl ether, filter, and dry to give 1-benzyl-4-(pyrid-3-yl)-4-((4-carboethoxymethylpiperazin-1-yl)carboxamido)piperidine. $R_f$=0.52 (silica gel, dichloromethane/methanol/concentrated aqueous ammonia, 90/10/1).

Combine 1-benzyl-4-(pyrid-3-yl)-4-((4-carboethoxymethylpiperazin-1-yl)carboxamido)piperidine (1.9 g) and ethanol 9200 mL). Add 5% palladium-on-carbon (1.2 g). Hydrogenate on a pressure apparatus at 65 psi. After 17 hours, filter through celite to remove the catalyst and evaporate the filtrate in vacuo to give a residue. Chromatograph the residue on silica gel eluting sequentially with 98/2 dichloromethane/methanol, 96/4 dichloromethane/methanol, 94/6/0.6 dichloromethane/methanol/concentrated aqueous ammonia, and then 94/8/0.6 dichloromethane/methanol/concentrated aqueous ammonia to give the title compound.

EXAMPLE 5

(R)-1-(3,4,5-Trimethoxybenzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine

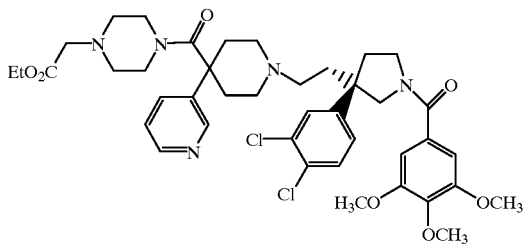

5.1.1 Resolution of (S)-3-(3,4-dichlorophenyl)-3-(2-hydroxyethyl)pyrrolidine (R,R)-di-p-anisoyltartaric acid salt and (R)-3-(3,4-dichlorophenyl)-3-(2-hydroxyethyl)pyrrolidine (R,R)-di-p-anisoyltartaric acid salt Combine 3-(3,4-dichlorophenyl)-3-(2-hydroxyethyl)pyrrolidine (1.0 g, 38.5 mmol) and butanone. Add a solution of (R,R)-di-p-anisoyltartaric acid (106 g, 38.0 mmol) in butanone (80 mL). Heat to reflux. After 15 minutes, cool to ambient temperature and then cool further in an salt-ice bath. Filter the solid that forms and rinse with butanone. Recrystallize the solid from water/methanol to give (S)-(−)-3-(3,4-dichlorophenyl)-3-(2-hydroxyethyl)pyrrolidine (R,R)-di-p-anisoyltartaric acid salt: mp; 201–204° C. (dec). $[\alpha]_D^0 = -18.9°$ (c=0.60, dimethylsulfoxide). X-ray diffraction analysis of a single crystal confirms the (S)-configuration. Analysis on HPLC, on an analytical sample of the free amine obtained by extraction, using a CHIRALPAK AD 25 cm×0.46 cm column eluting with pentane/methanol/triethylamine (80/10/0.1) with a flow rate of 1.0 mL/minute indicates an enantiomeric excess of 96%, (96% ee), retention time of the (S)-isomer 11.2 minutes, retention time of the (R)-isomer 14.5 minutes.

5.1.2 Resolution of (S)-3-(3,4-dichlorophenyl)-3-(2-hydroxyethyl)pyrrolidine (R,R)-di-p-anisoyltartaric acid salt and (R)-3-(3,4-dichlorophenyl)-3-(2-hydroxyethyl)pyrrolidine hydrochloric acid salt Combine (R,R)-di-p-anisoyltartaric acid (0.8 g, 19 mmol) and aqueous 12M hydrochloric acid solution (0.16 mL, 19 mmol) in water/methanol (10 mL)/(10 mL). Heat to reflux. Add dropwise, a solution of 3-(3,4-dichlorophenyl)-3-(2-hydroxyethyl)pyrrolidine (1.0 g, 38.5 mmol) in methanol (10 mL). After 15 minutes, slowly cool to ambient temperature. Filter the solid that forms and rinse with water to give (S)-3-(3,4-dichlorophenyl)-3-(2-hydroxyethyl)pyrrolidine (R,R)-di-p-anisoyltartaric acid mp; 201–204° C. (dec). Analysis by HPLC, as described in Example 5.1.1 indicates an enantiomeric excess of 97%, (97% ee).

5.1.3 Synthesis and resolution of (S)-3-(3,4-dichlorophenyl)-3-(2-hydroxyethyl)pyrrolidine (R,R)-di-p-anisoyltartaric acid salt Combine (3-(3,4-dichlorophenyl)-5-oxopyrrolidin-3-yl)-acetic acid ethyl ester (40 lb) and tetrahydrofuran (260 lb). Purge the vessel with nitrogen. Add a solution of borane dimethylsulfide complex (38 lb, 2M solution in tetrahydrofuran). Heat to reflux. After 60 hours, distill until the internal temperature rises to about 70° C. and then slowly quench the reaction with methanol (650 lb). Add water (650 lb). Add methanesulfonic acid (16 lb). Heat to reflux and remove the distillate to remove most of the residual tetrahydrofuran. Combine methanol (about 18 gal) and (R,R)-di-p-anisoyltartaric acid (32 lb). Heat to reflux and transfer to the vessel containing the above residue. Add seed crystals and slowly cool to 10° C. to give a solid. Collect the solid and combine methanol (145 gal) and water (145 gal). Heat to reflux. After 1 hour, slowly cool to 10° C. to give a solid. Collect the solid to give, after drying, the title compound.

5.1.4 Resolution to give (S)-1-(3,4,5-trimethoxybenzoyl)-3-(3,4-dichlorophenyl)-3-(2-hydroxyethyl)pyrrolidine Combine 1-(3,4,5-trimethoxybenzoyl)-3-(3,4-dichlorophenyl)-3-(2-hydroxyethyl)pyrrolidine (4.5 g 9.9 mmol) and dichloromethane/pyridine (70 mL, 6/1). Add acetic anhydride (1.04 mL, 11.0 mmol) and 4-dimethylaminopyridine (50 mg, 0.41 mmol). After 2 hours, concentrate the reaction mixture in vacuo to obtain a residue. Dissolve the residue in ethyl acetate and extract with 1M hydrochloric acid solution (2×200 mL), saturated sodium bicarbonate solutions and saturated sodium chloride solution. Dry the organic layer over $MgSO_4$, filters and concentrate in vacuo to obtain a residue. Chromatograph the residue on silica gel eluting with ethyl acetate to give 1-(3,4,5-trimethoxybenzoyl)-3-(3,4-dichlorophenyl)-3-(2-acetoxyethyl)pyrrolidine: $R_f$=0.38 (silica gel, ethyl acetate). Elemental Analysis calculated for $C_{24}H_{27}Cl_2NO_6$: C 58.07; H 5.48; N 2.82; Found: C 57.67; H 5.46; N 2.84.

Combine 1-(3,4,5-trimethoxybenzoyl)-3-(3,4-dichlorophenyl)-3-(2-acetoxyethyl)pyrrolidine (6.6 g, 13.3 mmol) and dichloromethane (100 mL). Add silica gel (32 g). Concentrate the slurry in vacuo to give a residue. Suspend the residue in phosphate buffer (800 mL, 0.1M, pH=7.5, the buffer was prepared with 11.5 g $H_3PO_4$ (85%) diluted to 1 L with deionized water and then adjusting the pH with solid potassium hydroxide pellets to 7.5) to obtain a slurry. Treat the slurry with Lipase (13 g, EC 3.1.1.3, Type VII, from Candida cylindracea). Monitor the reaction by HPLC on a CHIRALPAK AD 25 cm×0.46 cm column eluting with pentane/ethanol/methanol (80/15/5) with a flow rate of 1.0 mL/minute. Prepare an aliquot for analysis as follows: centrifuge the solution for 10 minutes at 14000 $cm^{-1}$, remove the supernatant and concentrate under a nitrogen stream to obtain a residue, dissolve the residue in dichloromethane (ca. 1 mL) and inject on the column for analysis. When the enantiomeric excess (ee) is satisfactory (>95% ee) for the (+)-acetate, filter the reaction. Rinse the solids with dichloromethane (8×500 mL). Extract the filtrate with dichloromethane (8×500 mL). Chromatograph the solids on silica gel eluting with 6% methanol/dichloromethane. Concentrate the combined eluant and extracts in vacuo to obtain a residue. Dissolve the residue in dichloromethane, dry over $MgSO_4$, filter, and concentrate in vacuo to give a residue. Chromatograph the residue on silica gel eluting with ethyl acetate to give (+)-1-(3,4,5-trimethoxybenzoyl)-3-(3,4-dichlorophenyl)-3-(2-acetoxyethyl)pyrrolidine: $R_f$=0.38 (silica gel, ethyl acetate). Elemental Analysis calculated for $C_{24}H_{27}Cl_2NO_6 \cdot 0.5 H_2O$: C 57.14; H 5.59; N 2.78; Found: C 57.37; H 5.45; N 2.87. $[\alpha]_D^0$=+36.4°(c=0.894, chloroform).

Combine (+)-1-(3,4,5-trimethoxybenzoyl)-3-(3,4-dichlorophenyl)-3-(2-acetoxyethyl)pyrrolidine (670 mg, 1.35 mmol) and aqueous lithium hydroxide solution (4.2 mL, 1M) in methanol (15 mL). After 3.5 hours, concentrate in vacuo to give a residue. Dissolve the residue in dichloromethane and extract with 1M hydrochloric acid solution and saturated sodium bicarbonate solution. Dry the organic layer over MgSO$_4$, filter, and concentrate in vacuo to obtain a residue. The residue was dried under high vacuum for 18 hours to give (S)-1-(3,4,5-trimethoxybenzoyl)-3-(3,4-dichlorophenyl)-3-(2-hydroxyethyl)pyrrolidine: R$_f$=0.11 (silica gel, ethyl acetate).

5.2.1 Synthesis of (S)-(+)-1-(3,4,5-trimethoxybenzoyl)-3-(3,4-dichlorophenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (0.14 g, 0.21 mmol) ethyl acetate (15 mL), acetonitrile (6 mL), water (6 mL), and sodium bicarbonate (0.09 g, 1.03 mmol). Cool to 0° C. in an salt-ice bath. Add 3,4,5-trimethoxybenzoyl chloride (0.048 g, 0.21 mmol). After 30 minutes, warm to ambient temperature. After 30 minutes at ambient temperature, partition the reaction mixture between ethyl acetate and brine. Extract the organic layer with 1M hydrochloric acid solution, then saturated aqueous sodium bicarbonate solution. Dry the organic layer over MgSO$_4$, filter, and evaporate in vacuo to give the title compound: R$_f$=0.11 (silica gel, ethyl acetate). [α]$_D^{20}$=+61.7°(c=1.01, methanol).

5.2.2 Synthesis of (S)-(+)-1-(3,4,5-trimethoxybenzoyl)-3-(3,4-dichlorophenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (6.0 g, 8.84 mmol) acetone (40 mL), water (40 mL), sodium hydroxide (0.335 g, 8.87 mmol), and sodium bicarbonate (3–73 g, 8.87 mmol). Cool to about 0° C. Add a solution of 3,4,5-trimethoxybenzoyl chloride (2,2 g, 9.7 mmol) in acetone (12 mL) over about 15 minutes. After 3 hours, partition the reaction mixture between ethyl acetate and brine. Extract the organic layer with 1M sodium hydroxide solution, saturated sodium bicarbonate solution, 1M hydrochloric acid solution, then brine. Dry the organic layer over MgSO$_4$, filter, and evaporate in vacuo to give the title compound: R$_f$=0.11 (silica gel, ethyl acetate).

5.3 Synthesis of (S)-1-(3,4,5-trimethoxybenzoyl)-3-(3,4-dichlorophenyl)-3-(2-methanesulfonyloxyethyl)pyrrolidine Prepare by the method of Example 2.5.2 using (S)-(+)-1-(3,4,5-trimethoxybenzoyl)-3-(3,4-dichlorophenyl)-3-(2-hydroxyethyl)pyrrolidine (1.351 mmol) and methanesulfonyl chloride (0.14 mL, 181 mmol) to give the title compound: R$_f$=0.27 (silica gel, ethyl acetate).

5.4.1 Synthesis of (R)-1-(3,4,5-trimethoxybenzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine Combine (S)-1-(3,4,5-trimethoxybenzoyl)-3-(3,4-dichlorophenyl)-3-(2-methanesulfonyloxyethyl)pyrrolidine (2 g), 4-(pyrid-3-yl)-4-((4-carboethoxymethylpiperazin-1-yl)carboxamido)piperidine (5.9 g), and N,N-diisopropylethylamine (1.53 g) in acetonitrile (40 mL). Heat to reflux. After 12 hours, evaporate in vacuo to give a residue. Chromatograph the residue on silica gel eluting sequentially with ethyl acetate, 98/2 dichloromethane/methanol, 96.5/3.5 dichloromethane/methanol, 95/5 dichloromethane/methanol, and then 94/6 dichloromethane/methanol to give the title compound. R$_f$=0.43 (silica gel, dichloromethane/methanol, 9/1).

5.4.2 Synthesis of (R)-1-(3,4,5-trimethoxybenzoyl)-3-(2-(4-(pyrid-3-yl)-4-(4-carboethoxymethylpiperazin-1-yl )carboxamido)piperidin-1-yl)ethyl)-3-(3,4-dichlorophenyl)pyrrolidine Combine 3,4,5-trimethoxybenzoic acid (3.5 kg, 16.5 mol) and 1,2-dimethoxyethane (14.2 kg) and dimethyl formamide (4 g). Cool in an ice bath. Add oxalyl chloride (2.99 kg, 23.5 mmol) over about 50 minutes not allowing the temperature of the reaction to raise above about 19° C. After 20 hours, concentrate in vacuo at 25° C. to remove about 3.7 kg of distillate to give a solution of 3,4,5-trimethoxybenzoyl chloride.

Combine (S)-3-(3,4-dichlorophenyl)-3-(2-hydroxyethyl)pyrrolidine (R,R)-di-p-anisoyltartaric acid salt (9.05 kg, 13.3 mol), potassium carbonate (6.42 kg) in acetone (27.2 kg). Cool to about 5° C. and add water (8.3 gal). Cool to about 3° C. and slowly add a solution of 3,4,5-trimethoxybenzoyl chloride (14.0 kg, 26.9% in 1,2-dimethoxethane, 16.3 mol) over about 25 minutes. When the reaction is complete, warm to 25° C. Dilute the reaction mixture with toluene (36.35 kg). Separate the layers and extract the organic layer with a solution of water (2 gal) and 3M aqueous hydrochloric acid solution (2 kg) and then brine. Concentrate the organic layer in vacuo until about 5 gallons remainsb. Add toluene (182 kg) and again concentrate in vacuo until about 5 gallons remain. Add toluene (36.15 kg) and cool to about −3° C. Add N-methylmorpholine (6.85 kg, 67.7 mol) and then methanesulfonyl chloride (3.40 kg, 29.7 mol). When the reaction is complete add water (4.8 gal) and warm to about 25° C. Separate the layers and extract the organic layer with a 3M aqueous hydrochloric acid solution (18.1 kg). Separate the layers to give a solution of (S)-1-(3,4,5-trimethoxybenzoyl)-3-(3,4-dichlorophenyl)-3-(2-methanesulfonyloxyethyl)pyrrolidine.

Combine the above solution of (S)-1-(3,4,5-trimethoxybenzoyl)-3-(3,4-dichlorophenyl)-3-(2-methanesulfonyloxyethyl)pyrrolidine, potassium carbonate (4.07 kg, 29.5 mol), 4-(pyrid-3-yl)-4-((4-carboethoxymethylpiperazin-1-yl)carboxamido)piperidine (12.0 mol), and water (3.3 gal). Heat to about 70° C. When the reaction is complete, dilute the reaction mixture with methyl ethyl ketone (18.1 kg) and after 15 minutes of stirring, separate the layers. Extract the organic layer with water (3.4 gal) and then concentrate in vacuo to give the title compound.

5.5 Synthesis of (R)-1-(3,4,5-trimethoxybenzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine hydrochloric acid salt Combine (R)-1-(3,4,5-trimethoxybenzoyl)-3-(2-(4-(pyrid-3-yl)-4-((4-carboethoxymethylpiperazin-1-yl)carboxamido)piperidin-1-yl)ethyl)-3-(3,4-dichlorophenyl)pyrrolidine (1.1 g) dichloromethane (50 mL). Cool in an ice bath. Purge with hydrochloric acid (gas, about 1.6 g) over about 10 minutes. Evaporate in vacuo to give a residue, twice add ethanol (50 mL) and evaporate in vacuo to give, after drying, the title compound.

EXAMPLE 6

(R)-1-(3,4,5-Trimethoxybenzoyl)-3-(2-(4-(pyrid-3-yl)-4-((4-carboxymethylpiperazin-1-yl)carboxamido)piperidin-1-yl)ethyl)-3-(3,4-dichlorophenyl)pyrrolidine

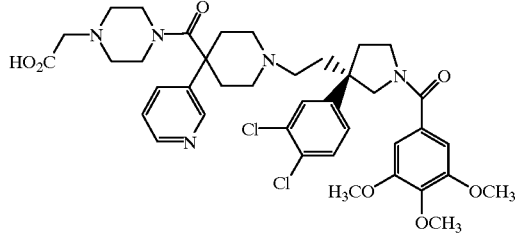

6.1 Synthesis of (R)-1-(3,4,5-trimethoxybenzoyl)-3-(2-(4-(pyrid-3-yl)-4-((4-carboxymethylpiperazin-1-yl)carboxamido)piperidin-1-yl)ethyl)-3-(3,4-dichlorophenyl)pyrrolidine hydrochloric acid salt Combine (R)-1-(3,4,5-trimethoxybenzoyl)-3-(2-(4-(pyrid-3-yl)-4-((4-carboethoxymethylpiperazin-1-yl)carboxamido) piperidine)ethyl)-3-(3,4-dichlorophenyl)pyrrolidine (0.3 g, 0.4 mmol) and lithium hydroxide (59 mg, 2.34 mmol) in tetrahydrofuran/water (6 mL/ 6 mL). Cool in an ice bath. After 2 hours, evaporate in vacuo to remove the tetrahydrofuran, cool in an ice bathe and acidify (pH of about 5) the aqueous reaction mixture using aqueous 1M hydrochloric acid solution. Adjust the pH of the aqueous reaction mixture to about 7 using sodium bicarbonate and extract with dichloromethane. Dry the organic layer over $MgSO_4$ and filter. Purge the filtrate with hydrochloric acid (gas) and then evaporate in vacuo to give, after drying, the title compound. $R_f$=0.71 (silica gels dichloromethane/methanol/concentrated aqueous ammonia, 80/20/1).

PREPARATION 3

4-Phenyl-4-((4-carboethoxymethylpiperazin-1-yl)carboxamido)piperidine hydrochloric acid salt Combine 1-t-butoxycarbonyl-4-phenyl-piperidine-4-carboxylic acid (27.0 g, 88.5 mmol), N,N-diisopropylethylamine (34 mL, 0.195 mol), 4-carboethoxymethylpiperazine (5.8 g), and 1-hydroxybenzotriazole hydrate (13.2 g, 98 mmol) in dichloromethane (400 mL). Add 1-(3-dimethylaminopropyl)-3-ethylcarbodiimide hydrochloride (18.7 g, 87.5 mmol). After 20 hours, dilute the reaction mixture with dichloromethane and extract twice with water. Dry the organic layer over $MgSO_4$, filters and evaporate in vacuo to give a residue. Chromatograph the residue on silica gel eluting sequentially with 20% ethyl acetate/hexane, ethyl acetate, 94/6 dichloromethane/methanol, and then 90/10 dichloromethane/methanol to give 1-t-butoxycarbonyl-4-phenyl-4-((4-carboethoxymethylpiperazin-1-yl))carboxamido) piperidine.

Combine 1-t-butoxycarbonyl-4-phenyl-4-((4-carboethoxymethylpiperazin-1-yl))carboxamido) piperidine (37.5 g, 78 mmol) and dichloromethane (300 mL). Add a solution of hydrochloric acid in dioxane (70 mL, 4M, 280 mmol). After 5 hours, add diethyl ether and continue stirring to give a solid. Collect the solid, rinse with diethyl ether, and dry to give the title compound.

EXAMPLE 7

1-(3,4,5-Trimethoxybenzoyl)-3-(2-(4-phenyl-4-((4-carboxymethylpiperazin-1-yl)carboxamido)peridin-1-yl)ethyl)-3-(3,4-dimethylphenyl)pyrrolidine

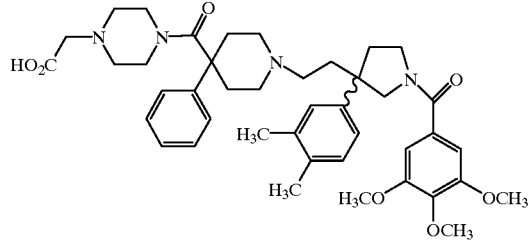

7.1.1 Synthesis of 3-cyano-3-(3,4-dimethylphenyl)pentanedioic acid diethyl ester Combine 3,4-dimethylphenylacetonitrile (50.0 mmol) and tetrahydrofuran (140 mL). Cool to about 5° C. Add dropwise a solution of sodium bis(trimethylsilyl)amide (800 mL, 1M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above 20° C. Allow to stir at ambient temperature After 18 hours, dilute with diethyl ether (15 L) and extract with saturated aqueous solution of ammonium chloride, then water, and then saturated aqueous solution of sodium chloride. Dry the organic layer over $MgSO_4$, filter, and concentrate in vacuo to give the title compound.

7.1.2 Synthesis of 3-cyano-3-(3,4-dimethylphenyl)pentanedioic acid diethyl ester Cool a solution of sodium bis(trimethylsilyl)amide (723 mL, 1M in tetrahydrofuran, 723 mmol) to 0° C. in an ice bath. Add a solution of 3,4-dimethylphenylacetonitrile (50.0 mmol) in tetrahydrofuran (130 mL) over about 1.5 hours. When the addition is complete, warm the reaction mixture to ambient temperature and allow to stir. After 2 hours, transfer the above solution via cannula into a cooled (−50° C.) solution of ethyl bromoacetate (126 g, 757 mmol) in tetrahydrofuran (250 mL). After the transfer is complete, allow the reaction mixture to warm to ambient temperature. After 18 hours, dilute with diethyl ether (500 mL) and extract with waters 1M hydrochloric acid solution, saturated aqueous solution of sodium bicarbonate, and then brine. Dry the organic layer over $MgSO_4$, filters and concentrate in vacuo to give a residue. Recrystallize the residue from diethyl ether to give the title compound as a solid.

7.2.1 Synthesis of (3-(3,4-dimethylphenyl)-5-oxopyrrolidin-3-yl)acetic acid ethyl ester Prepare by the method of Example 2.2.2 using 3-cyano-3-(3,4-dimethylphenyl)pentanedioic acid diethyl ester to give the title compound.

7.2.2 Synthesis of (3-(3,4-dimethylphenyl)-5-oxopyrrolidin-3-yl)acetic acid ethyl ester Combine 3-cyano-3-(3,4-dimethylphenyl)pentanedioic acid diethyl ester (56 g, 177 mmol) and ethanol (500 mL) in a Parr bottle. Add Raney nickel (50 g) and an aqueous concentrated ammonia solution (85 mL). Hydrogenate at 50° C. and 100 psi for 48 h. Filter through a celite pad and rinse the solids with ethanol. Evaporate the filtrate in vacuo to obtain a residue. Chromatograph the residue on silica gel eluting with 6% methanol/dichloromethane to give the title compound.

7.3 Synthesis of 3-(3,4-dimethylphenyl)-3-(2-hydroxyethyl) pyrrolidine

Prepare by the method of Example 2.3 using (3-(3,4-dimethylphenyl)-5-oxopyrrolidin-3-yl)acetic acid ethyl ester to gives after recrystallization from dichloromethane/diethyl ether, the title compound: $R_f$=0.35 (silica gels 85/10/5 dichloromethane/methanol/acetic acid).

7.4 Synthesis of 1-(3,4,5-trimethoxybenzoyl)-(3-(3,4-dimethylphenyl)-3-(2-hydroxyethyl)pyrrolidine Combine 3-(3,4-dimethylphenyl)-3-(2-hydroxyethyl) pyrrolidine (20 mmol) and sodium bicarbonate (8.4 g) in acetone (50 mL)/water (50 mL). Add a solution of 3,4,5-trimethoxybenzoyl chloride (4.6 g, 19.9 mmol) in acetone (50 mL). After 3 hours, extract the reaction mixture three times with ethyl acetate. Dry the organic layer over $MgSO_4$, filters and concentrate in vacuo to give the title compound: $R_f$=0.25 (silica gels 6% methanol/dichloromethane).

7.5 Synthesis of 1-(3,4,5-trimethoxybenzoyl)-3-(3,4-dimethylphenyl)-3-(2-methanesulfonyloxyethyl)pyrrolidine Prepare by the method of Example 2.5.2 using 1-(3,4,5-trimethoxybenzoyl)-3-(3,4-dimethylphenyl)-3-(2-hydroxyethyl)pyrrolidine to give the title compound: $R_f$=0.44 (silica gel, ethyl acetate).

7.6 Synthesis of 1-(3,4,5-trimethoxybenzoyl)-3-(2-(4-phenyl-4-((4-carboethoxymethylpiperazin-1-yl) carboxamido)piperidin-1-yl)ethyl)-3-(3,4-dimethylphenyl) pyrrolidine Prepare by the method of Example 1.6 using 1-(3,4,5-trimethoxybenzoyl)-3-(3,4-dimethylphenyl)-3-(2-methanesulfonyloxyethyl)pyrrolidine and 4-phenyl-4-((4-carboethoxymethylpiperazin-1-yl)carboxamido)piperidine to give the title compound.

7.7 Synthesis of 1-(3,4,5-trimethoxybenzoyl)-3-(2-(4-phenyl-4-((4-carboxymethylpiperazin-1-yl)carboxamido) piperidin-1-yl)ethyl)-3-(3,4-dimethylphenyl)pyrrolidine Prepare by the method of Example 1.7 using 1-(3,4,5-trimethoxybenzoyl)-3-(2-(4-phenyl-4-((4-carboethoxymethylpiperazin-1-yl)carboxamido)piperidin-1-yl)ethyl)-3-(3,4-dimethylphenyl)pyrrolidine to give the title compound.

PREPARATION 4

4-Phenyl-4-((4-carboethoxymethylpiperazin-1-yl) carboxamido)piperidine hydriodic acid salt Combine 1-t-butoxycarbonyl-4-phenyl-4-((4-carboethoxymethylpiperazin-1-yl))carboxamido) piperidine (26.0 g, 56.7 mmol) and dichloromethane (40 mL). Add hydriodic acid (gas 2.8 g). After 3 hours, evaporate in vacuo to give, after drying, the title compound.

Alternately, combine 1-t-butoxycarbonyl-4-phenyl-4-((4-carboethoxymethylpiperazin-1-yl))carboxamido) piperidine (10.0 g, 21.8 mmol) and ethanol (700 mL). Add an aqueous solution of hydriodic acid (57%, 6.1 mL, 45.75 mmol). After 2 hours, heat to reflux. After 19 hours, cool to ambient temperature and dilute the reaction mixture with diethyl ether (300 mL) to give a solid. Cool in an ice bath. After 1 hour, collect the solid by filtration, rinse with diethyl ether, and dry to give the title compound. Elemental Analysis calculated for $C_{20}H_{29}N_3O_3 \cdot 2$ HI: C 39.04; H 5.08; N 6.83; Found: C 39.14; H 5.38; N 6.88.

EXAMPLE 8

(R)-1-(3,4,5-Trimethoxybenzoyl)-3-(2-(4-phenyl-4-((4-carboethoxymethylpiperazin-1-yl)carboxamido) piperidin-1-yl)ethyl)-3-(3,4-dichlorophenyl) pyrrolidine

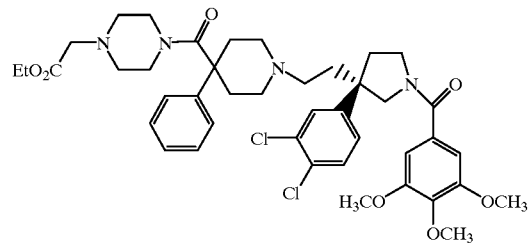

8.1.1 Synthesis of (R)-1-(3,4,5-trimethoxybenzoyl)-3-(2-(4-phenyl-4-((4-carboethoxymethylpiperazin-1-yl) carboxamido)piperidine)ethyl)-3-(3,4-dichlorophenyl) pyrrolidine Combine (S)-1-(3,4,5-trimethoxybenzoyl)-3-(3,4-dichlorophenyl)-3-(2-methanesulfonyloxyethyl)pyrrolidine (2 g), 4-phenyl-4-((4-carboethoxymethylpiperazin-1-yl) carboxamido)piperidine hydriodic acid salt (3.1 g, 5 mmol), and N,N-diisopropylethylamine (3 mL) in acetonitrile (25 mL). Heat to reflux. After 28 hours, cool the reaction mixture and dilute with ethyl acetate (200 mL). Filter the diluted reaction mixture and extract the filtrate twice with saturated aqueous sodium bicarbonate and then brine. Dry the organic layer over $MgSO_4$, filter, and evaporate in vacuo to give residue. Combine the residue and diethyl ether/ethyl acetate (300 mL/70 mL). Heat to reflux and filter to give a filtrate. Combine the filtrate and oxalic acid (1 g) to give a solid. Collect the solid by filtration. Combine the solid and dichloromethane/saturated aqueous sodium bicarbonate solution (500 mL/500 mL) and stir. Separate the organic layer and extract with water. Dry the organic layer over $MgSO_4$, filter, and evaporate in vacuo to give the title compound. $R_f$=0.39 (silica gel, 6% methanol/dichloromethane).

8.1.2 Synthesis of (R)-1-(3,4,5-trimethoxybenzoyl)-3-(2-(4-phenyl-4-((4-carboethoxymethylpiperazin-1-yl) carboxamido)piperidine)ethyl)-3-(3,4-dichlorophenyl) pyrrolidine Combine (S)-1-(3,4,5-trimethoxybenzoyl)-3-(3,4-dichlorophenyl)-3-(2-methanesulfonyloxyethyl)pyrrolidine (43.4 g, 81.5 mmol), 4-phenyl-4-((4-carboethoxymethylpiperazin-1-yl)carboxamido)piperidine hydrochloric acid salt (32 g, 70 mmol), and potassium carbonate (35 g, 253 mmol) in tetrahydrofuran (225 mL) and water (75 mL). Heat to reflux. After 108 hours, cool the reaction mixture and separate the organic layer. Extract the aqueous layer twice with dichloromethane. Combine the organic layers and dry over $MgSO_4$, filter, and evaporate in vacuo to give residue. Chromatograph the residue on silica gel eluting sequentially with ethyl acetate, 1% methanol/dichloromethane 2% methanol/dichloromethane 3% methanol/dichloromethane 4% methanol/dichloromethane 5% methanol/dichloromethane and then 6% methanol/dichloromethane to give the title compound. $R_f$=0.37 (silica gel, 6% methanol/dichloromethane). HRMS calculated for $C_{42}H_{53}Cl_2N_4O_7$ 795.329131. Found 795.329832.

8.2.1 Synthesis of (R)-1-(3,4,5-trimethoxybenzoyl)-3-(2-(4-phenyl-4-((4-carboethoxymethylpiperazin-1-yl) carboxamido)piperidine)ethyl)-3-(3,4-dichlorophenyl) pyrrolidine oxalic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and toluene (10 mL). Add oxalic acid (0.25 g, 2.8 mmol). Add ethyl acetate (5 mL) to give a solid. After 30 minutes, collect the solid by filtration, rinse with toluene, and dry to give the title compound.

8.2.2 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine oxalic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and toluene (10 mL). Add oxalic acid (0.125 g, 1.4 mmol). Add ethyl acetate (3 mL) to give a solid. After 30 minutes, collect the solid by filtration, rinse with toluene, and dry to give the title compound.

8.2.3 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine oxalic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and butanone (20 mL). Add a solution of oxalic acid (0.125 g, 1.4 mmol) in butanone (5 mL) to give a solid. After 5 minutes, collect the solid by filtration and dry to give the title compound.

8.3.1 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine hydrochloric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (45.6 g, 57.3 mmol) and dichloromethane (600 mL) and filter. With stirring, add hydrochloric acid (gas). After 1 hour, evaporate in vacuo to give a residue. Triturate the residue with diethyl ether, filters and dry to give the title compound.

8.3.2 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine hydrochloric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.19 g, 1.46 mmol) and dichloromethane (15 mL). Cool in an ice bath. Purge the solution with hydrochloric acid gas. After 1 hour, evaporate in vacuo to give the title compound.

8.4 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine maleic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (0.88 g, 1.1 mmol) and ethanol (5 mL). Heat to reflux. Add a solution of maleic acid (0.28 g, 2.4 mmol) in ethanol (5 mL). After 5 minutes, allow the reaction mixture to cool and add diethyl ether to give a solid. Collect the solid by filtration and dry to give the title compound.

8.5.1 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine fumaric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and ethyl acetate (5 mL). Heat to reflux. Add a solution of fumaric acid (0.32 g, 2.76 mmol) in ethyl acetate/ethanol (5 mL/5 mL). After 5 minutes, allow the reaction mixture to cool and evaporate in vacuo to give a residue. Triturate the residue with diethyl ether to give the title compound.

8.5.2 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine fumaric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and ethanol (20 mL). Heat to reflux. Add fumaric acid (0.30 g). After 15 minutes, allow the reaction mixture to cool and evaporate in vacuo to give a residue. Triturate the residue with diethyl ether to give a solid. Collect the solid by filtration and dry to give the title compound. Elemental Analysis calculated for $C_{48}H_{58}Cl_2N_4O_{13} \cdot 1.27\ H_2O$: C, 58.07; H, 6.15; N, 5.64. Found: C; 57.95, H, 6.13; N, 5.46.

8.6.1 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine citric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (2.0 g, 2.6 mmol) and ethyl acetate (10 mL). Heat to about 50° C. Add a solution of citric acid (0.5 g, 2.6 mmol) in ethanol (5 mL). After 30 minutes, allow the reaction mixture to cool and add diethyl ether to give a solid. Evaporate in vacuo to give the title compound.

8.6.2 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine citric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (0.5 g, 0.65 mmol) and ethyl acetate (4 mL). Heat to about 50° C. Add a solution of citric acid (0.25 g, 1.3 mmol) in ethanol (2 mL). After 30 minutes, allow the reaction mixture to cool and add diethyl ether to give a solid. Evaporate in vacuo to give the title compound.

8.6.3 Synthesis of (R)-1-(3.4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine citric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g) and ethanol (30 mL). Add a solution of citric acid (0.5 g) in ethanol (5 mL). After 1 hour, evaporate in vacuo to give the title compound.

8.7 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine methanesulfonic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (2.0 g, 2.6 mmol) and ethanol (10 mL). Heat to about 45° C. Add a solution of methanesulfonic acid (10 g, 10.4 mmol) in diethyl ether (2 mL). After 30 minutes, add diethyl ether to give a solid. Evaporate in vacuo and add diethyl ether. Four times decant the solvent and add diethyl ether. Collect the solid by filtration and dry to give the title compound.

8.8 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine 2-hydroxyethanesulfonic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and ethanol (10 mL). Add an aqueous solution of 2-hydroxyethanesulfonic acid (14 mL, 0.18M, 2.52 mmol). Heat to reflux. After 15 minutes, cool and evaporate in vacuo to give a residue. Triturate the residue with diethyl ether to give a solid. Collect the solid by filtration and dry to give the title compound.

8.9 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine hydrobromic acid salt Combine ethanol (1 mL) and diethyl ether (10 mL). Cool in an ice bath. Add acetyl bromide ((0.2 mL). After 5 minutes, add the above solution to a solution of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (2 g) in ethyl acetate (20 mL). Add diethyl ether (40 mL) to give a solid. After 1.5 hours, filter, rinse with diethyl ether and dry to give the title compound.

8.10 Synthesis of (R)-1-(3,4,5-trimethoxybenzoyl)-3-(2-(4-phenyl-4-((4-carboethoxymethylpiperazin- 1-yl)carboxamido)piperidine)ethyl)-3-(3,4-dichlorophenyl)pyrrolidine tartaric acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g 1.26 mmol) and (1)-tartaric acid (0.6 g) in acetone (25 mL). Heat to about 50° C. After 1 hour. cool to ambient temperature. After 72 hours, concentrate in vacuo, and add diethyl ether (40 mL) to give a solid. Collect the solid by filtration, rinse with diethyl ether and dry to give the title compound.

8.11 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine ethanesulfonic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (0.88 g) and ethanol (20 mL). Add ethanesulfonic acid (0.24 g). After 30 minutes, concentrate the reaction mixture in vacuo to obtain a residue. Combine the residue with diethyl ether and evaporate to give the title compound.

8.12 Synthesis of (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1R)-(−)-10-camphorsulfonic acid salt Combine (R)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine (1.0 g, 1.26 mmol) and (1R)-(−)-10-camphorsulfonic acid (0.6 g) in acetone (25 mL). Heat to about 50° C. After 1 hour, cool to ambient temperature. After 72 hours, filters concentrate in vacuo, and add diethyl ether (40 mL) to give a solid. Collect the solid by filtration, rinse with diethyl ether and dry to give the title compound.

EXAMPLE 9

(R)-1-(3,4,5-Trimethoxybenzoyl)-3-(2-(4-phenyl-4-((4-carboxymethylpiperazin-1-yl)carboxamido)piperidin-1-yl)ethyl)-3-(3,4-dichlorophenyl)pyrrolidine

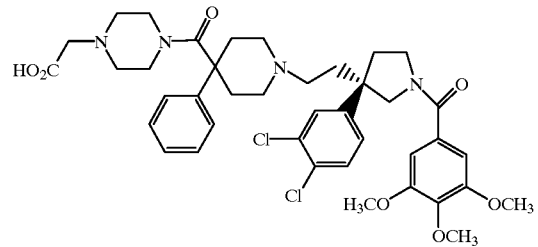

9.1 Synthesis of (R)-1-(3,4,5-trimethoxybenzoyl)-3-(2-(4-phenyl-4-((4-carboxymethylpiperazin-1-carboxamido)piperidine)ethyl)-3-(3,4-dichlorophenyl)pyrrolidine While cooling in an ice bath, combine (R)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine hydrochloride salt (1.0 g, 1.2 mmol) and lithium hydroxide (0.3 g, 12.6 mmol) in tetrahydrofuran/water (20 mL/20 mL). After 5 hour, evaporate in vacuo to remove most of the tetrahydrofuran. Adjust the pH to 6 using a 1M aqueous solution of hydrochloric acid. Extract the neutralized aqueous reaction mixture with dichloromethane. Dry the organic layer over $MgSO_4$, filter, and evaporate in vacuo to give the title compound.

9.2 Synthesis of (R)-1-(3,4,5-trimethoxybenzoyl)-3-(2-(4-phenyl-4-((4-carboxymethylpiperazin-1-yl)carboxamido)piperidine)ethyl)-3-(3,4-dichlorophenyl)pyrrolidine hydrochloric acid salt Combine (R)-1-(3,4,5-trimethoxybenzoyl)-3-(2-(4-phenyl-4-((4-carboxymethylpiperazin-1-yl)carboxamido)piperidine)ethyl)-3-(3,4-dichlorophenyl)pyrrolidine (2.25 g, 2.94 mmol) and a saturated solution of hydrochloric acid in dichloromethane (200 mL). After 2 hours, evaporate in vacuo to give the title compound. HRMS calculated for $C_{40}H_{49}Cl_2N_4O_7$ 767.297831. Found 767.298515.

PREPARATION 5

2-Methoxy-5-(1H-tetrazol-1-yl)benzoyl chloride

Combine 2-hydroxy-5-nitrobenzoic acid (21.5 g, 117 mmol), potassium carbonate (162.3 g, 1.174 mol, and methyl iodide (136.8 g, 96.4 mmol) in acetone (500 mL). Heat to reflux. After 18 hours, cool the reaction mixture to ambient temperature and add methyl iodide (136.8 g, 96.4 mmol). Again, heat to reflux. After 56 hours, cool the reaction mixture to ambient temperature and filters rinse with acetone, and evaporate the filtrate in vacuo to give a residue. Recrystallize the residue from ethanol to give a second residue. Combine the second residue and chloroform (about 100 mL), filter and evaporate the filtrate in vacuo to give methyl 2-methoxy-5-nitrobenzoate. $R_f$=0.38 (silica gels ethyl acetate/hexane 1/1).

Combine methyl 2-methoxy-5-nitrobenzoate (13.3 g, 63 mmol) and methanol. Add 5% palladium-on-carbon (0.66 g). Hydrogenate on a pressure apparatus at 50 psi. After 17 hours, filter through celite to remove the catalyst and evaporate the filtrate in vacuo to give a residue. Combine the residue and dichloromethane and extract with water. Dry the organic layer over Na$_2$SO$_4$, filters and evaporate in vacuo to give methyl 2-methdxy-5-aminobenzoate. R$_f$=0.18 (silica gel, ethyl acetate/methanol 1/1). Elemental Analysis calculated for C$_9$H$_{11}$NO$_3$: C, 59.66; H, 6.12; N, 7.73. Found: C, 59.44; H, 6.04; N, 7.62.

Combine methyl 2-methoxy-5-aminobenzoate (3.94 g, 21.7 mmol) and triethyl orthoformate (12.8 g, 86.7 mmol) in glacial acetic acid (20 mL). After 20 hours, concentrate the reaction mixture in vacuo to remove ethanol. Add glacial acetic acid (20 mL) and sodium azide (5.64 g, 86.7 mmol). Heat to 70° C. After 1 hour, add glacial acetic acid (10 mL) and continue to heat to 70° C. After an additional hour, cool the reaction mixture to ambient temperature, dilute with water (500 mL). Collect the solid by filtration, rinse with water, and dry to give methyl 2-methoxy-5-(1H-tetrazol-1-yl)benzoate.

Combine methyl 2-methoxy-5-(1H-tetrazol-1-yl)benzoate (2.86 g, 12.2 mmol) and a 1M aqueous solution of sodium hydroxide (13.43 mL, 13.43 mmol) in methanol/water (100 mL, 5:1 vol./vol.). Heat to reflux. After 4 hours, concentrate in vacuo to remove most of the methanol, add water (50 mL), and adjust the pH to about 4 using a 1M aqueous hydrochloric acid solution. Evaporate in vacuo to give a solid, slurry the solid with water, filter, and dry to give 2-methoxy-5-(1H-tetrazol-1-yl)benzoic acid.

Alternately, combine methyl 2-methoxy-5-(1H-tetrazol-1-yl)benzoate (13.3 g, 56.8 mmol) and methanol (150 mL). Add 1M aqueous solution of sodium hydroxide (62.5 mL, 62.5 mmol). Heat to reflux. After 30 minutes, add methanol (50 mL) and water (50 mL) and continue the heat at reflux. After 1 hour, concentrate in vacuo to remove most of the solvent. Adjust the pH to about 1 to 2 using a 1M aqueous hydrochloric acid solution to give a solid. Collect the solid by filtration, rinse with water, and dry to give 2-methoxy-5-(1H-tetrazol-1-yl)benzoic acid.

Combine 2-methoxy-5-(1H-tetrazol-1-yl)benzoic acid (1.2 g, 5.5 mmol) and dichloromethane (40 mL). Add dropwise oxalyl chloride (0.72 mL, 8.25 mmol) followed by dimethylformamide (3 drops) After 4 hours, evaporate in vacuo and dry to give the title compound.

EXAMPLE 10

(R)-1-(2-methoxy-5-(1H-tetrazol-1-yl benzoyl)-3-(2-(4-phenyl-4-((4-carboethoxymethylpiperazin-1-yl)carboxamido) piperidin-1-yl)ethyl)-3-(3,4-dichlorophenyl)pyrrolidine

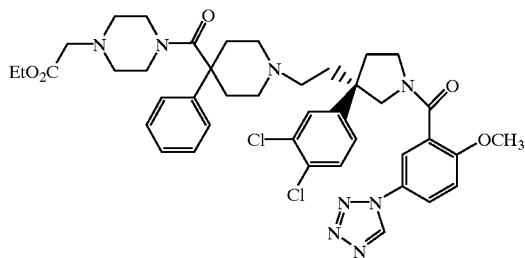

10.1 Synthesis of (S)-1-(2-methoxy-5-(1H-tetrazol-1-yl)benzoyl)-(3-(3,4-dichlorophenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (1.21 g, 5.5 mmol) and sodium bicarbonate (2.6 g, 31 mmol) in acetone/water (20 mL/20 mL). Cool in an ice bath. Add 2-methoxy-5-(1H-tetrazol-1-yl)benzoyl chloride (1.48 g, 6.2 mmol). After 30 minutes, warm to ambient temperatures After 6 hours, filter the reaction mixture and extract the filtrate with ethyl acetate. Extract the organic layer with a saturated aqueous sodium bicarbonate solution and then brine. Dry the organic layer over MgSO$_4$, filter, and evaporate in vacuo to give residue. Chromatograph the residue on silica gel eluting sequentially with ethyl acetate, 3% methanol/ethyl acetate, and then 6% methanol/ethyl acetate to give the title compound: R$_f$=0.38 (silica gel, 6% methanol/dichloromethane).

10.2 Synthesis of (S)-1-(2-methoxy-5-(1H-tetrazol-1-yl)benzoyl)-3-(3,4-dichlorophenyl)-3-(2-methanesulfonyloxyethyl)pyrrolidine Prepare by the method of Example 2.5.2 using (S)-1-(2-methoxy-5-(1H-tetrazol-1-yl)benzoyl)-3-(3,4-dichlorophenyl)-3-(2-hydroxyethyl)pyrrolidine (0.6 g, 1.3 mmol) and methanesulfonyl chloride (0.12 mL, 1.55 mmol) to give the title compounds R$_f$=0.20 (silica gel, ethyl acetate).

10.3 Synthesis of (R)-1-(2-methoxy-5-(1H-tetrazol-1-yl)benzoyl)-3-(2-(4-phenyl-4-((4-carboethoxymethylpiperazin-1-yl)carboxamido)piperidine)ethyl)-3-(3,4-dichlorophenyl)pyrrolidine Combine (S)-1-(2-methoxy-5-(1H-tetrazol-1-yl)benzoyl)-3-(3,4-dichlorophenyl)-3-(2-methanesulfonyloxyethyl)pyrrolidine (1.0 g, 1.62 mmol), 4-phenyl-4-((4-carboethoxymethylpiperazin-1-yl)carboxamido)piperidine hydriodic acid salt (0.81 g, 1.3 mmol), and N,N-diisopropylethylamine (1 mL, 5.8) in acetonitrile (25 mL). Heat to reflux. After 15 hours, cool and evaporate in vacuo to give a residue. Partition the residue between water and ethyl acetate. Separate the organic layer and extract with a saturated aqueous sodium bicarbonate solution and then brine. Dry the organic layer over MgSO$_4$, filters and evaporate in vacuo to give residue. Chromatograph the residue on silica gel eluting sequentially with ethyl acetate, 3% methanol/ethyl acetate, and then 6% methanol/ethyl acetate to give the title compound. R$_f$=0.31 (silica gels 6% methanol/dichloromethane).

10.4 Synthesis of (R)-1-(2-methoxy-5-(1H-tetrazol-1-yl)benzoyl)-3-(2-(4-phenyl-4-((4-carboethoxymethylpiperazin-1-yl)carboxamido)piperidine)ethyl)-3-(3,4-dichlorophenyl)pyrrolidine hydrochloric acid salt Combine (R)-1-(2-methoxy-5-(1H-tetrazol-1-yl)benzoyl)-3-(2-(4-phenyl-4-((4-carboethoxymethylpiperazin-1-yl)carboxamido)piperidine)ethyl)-3-(3,4-dichlorophenyl)pyrrolidine (0.74 g, 0.91 mmol) and dichloromethane (25 mL). Cool in an ice bath. With stirring, add hydrochloric acid (gas). After 1 hours evaporate in vacuo to give a residues Add dichloromethane, evaporate in vacuo, and dry to give the title compound.

EXAMPLE 11

(R)-1-(2-methoxy-5-(1H-tetrazol-1-yl)benzoyl)-3-(2-(4-phenyl-4-((4-carboxymethylpiperazin-1-yl)carboxamido) piperidin-1-yl)ethyl)-3-(3,4-dichlorophenyl)pyrrolidine hydrochloric acid salt

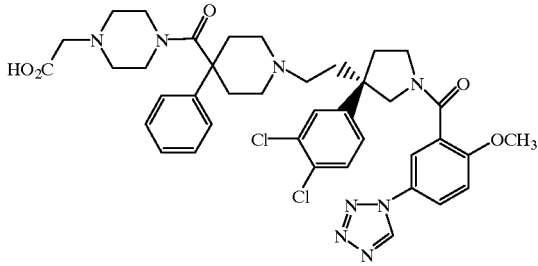

11.1 Synthesis of (R)-1-(2-methoxy-5-(1H-tetrazol-1-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine hydrochloric acid salt Combine (R)-1-(2-methoxy-5-(1H-tetrazol-1-yl)benzoyl)-3-(2-(4-phenyl-4-((4-carboethoxymethylpiperazin-1-yl)carboxamido)piperidine)ethyl)-3-(3,4-dichlorophenyl)pyrrolidine hydrochloric acid salt (0.3 g, 0.34 mmol) and lithium hydroxide (50 mg, 2.1 mmol) in tetrahydrofuran/water (10 mL/10 mL). After 2 hours evaporate in vacuo to remove most of the tetrahydrofuran. Adjust the pH to 6 using a 1M aqueous solution of hydrochloric acid. Evaporate the aqueous reaction mixture in vacuo to give a residue. Combine the residue and ethanol and again evaporate in vacuo to give a residue, add waters stirs and decant to give a residues Combine the residue and a 1M solution of hydrochloric acid and evaporate in vacuo and then add ethanol and evaporate in vacuo to give, after drying, the title compound. Elemental Analysis calculated for $C_{39}H_{44}Cl_2N_8O_5 \cdot 2HCl \cdot 3.71\ H_2O$: C 51.17; H, 5.88; N 12.24. Found: C 51.35; H 5.80; N 12.02.

EXAMPLE 12

(S)-1-(3,4,5-Trimethoxybenzoyl)-3-(2-(4-phenyl-4-((4-carboethoxymethylpiperazin-1-yl)carboxamido) piperidin-1-yl)ethyl)-3-(3,4-dichlorophenyl) pyrrolidine

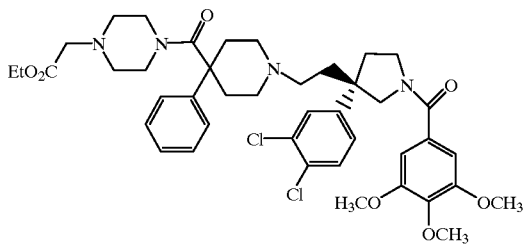

12.1 Resolution of (R)-(+)-3-(3,4-dichlorophenyl)-3-(2-hydroxyethyl)pyrrolidine (S,S)-di-p-anisoyltartaric acid salt Combine (S,S)-di-p-anisoyltartaric acid (14.77 g, 35 mmol), water (200 mL) and methanol (200 mL). Heat to reflux. Add dropwise, a solution of 3-(3,4-dichlorophenyl)-3-(2-hydroxyethylpyrrolidine (18.36 g, 70 mmol) in methanol (135 mL). After 1.5 hours, add water (135 mL) and slowly cool to ambient temperature to give a solid. Filter the solid that forms and rinse with water to give the title compound: mp; 201–202° C. (dec). Analysis by HPLC, as described in Example 5.1.1 indicates an enantiomeric excess of 99.9%, (99.9% ee). $[\alpha]_D^{20}=+17.9°(C=1.00,$ dimethylsulfoxide).

12.2 Synthesis of (R)-1-(3,4,5-trimethoxybenzoyl)-3-(3,4-dichlorophenyl)-3(2-hydroxyethyl)-pyrrolidine Prepare by the method of Example 5.2.2 using (R)-3-(3,4-dichlorophenyl)-3-(2-hydroxyethyl)pyrrolidine (R,R)-di-p-anisoyltartaric acid salt to give the title compound: $R_f$=0.29 (silica gel, 6% methanol/dichloromethane).

12.3 Synthesis of (R)-1-(3,4,5-trimethoxybenzoyl)-3-(3,4-dichlorophenyl)-3-(2-methanesulfonyloxyethyl)pyrrolidine Prepare by the method of Example 2.5.2 (S)-1-(3,4,5-trimethoxybenzoyl)-3-(3,4-dichlorophenyl)-3-(2-hydroxyethyl)pyrrolidine to give the title compound: $R_f$=0.33 (silica gel, ethyl acetate) and $R_f$=0.44 (silica gel, 6% methanol/dichloromethane).

12.4 Synthesis of (S)-1-(3,4,5-trimethoxybenzoyl)-3-(2-(4-phenyl-4-((4-carboethoxymethylpiperazin-1-yl) carboxamido)piperidine)ethyl)-3-(3,4-dichlorophenyl) pyrrolidine Combine (R)-1-(3,4,5-trimethoxybenzoyl)-3-(3,4-dichlorophenyl)-3-(2-methanesulfonyloxyethyl)pyrrolidine (5 g, 9.4 mmol) 4-phenyl-4-((4-carboethoxymethylpiperazin-1-yl)carboxamido)piperidine hydriodic acid salt (5.0 g, 8.1 mmol), and N,N-diisopropylethylamine (4.6 g, 35.5 mmol) in acetonitrile (100 mL). Heat to reflux. After 19 hours, cool the reaction mixture and evaporate in vacuo to give a first residue. Combine the first residue and dichloromethane and extract with saturated aqueous sodium bicarbonate and then brine. Dry the organic layer over $MgSO_4$, filter, and evaporate in vacuo to give a second residue. Chromatograph the second residue eluting sequentially with 1% methanol/dichloromethane, 15% methanol/dichloromethane, 2% methanol/dichloromethane, and then 3% methanol/dichloromethane give the title compound.

12.5 Synthesis of (S)-1-(3,4,5-trimethoxybenzoyl)-3-(2-(4-phenyl-4-((4-carboethoxymethylpiperazin-1-yl) carboxamido)piperidine)ethyl)-3-(3,4-dichlorophenyl) pyrrolidine hydrochloric acid salt Prepare by the method of Example 8.4 using (S)-1-(3,4,5-trimethoxybenzoyl)-3-(2-(4-phenyl-4-((4-carboethoxymethylpiperazin-1-yl)carboxamido)piperidine) ethyl)-3-(3,4-dichlorophenyl)pyrrolidine to give the title compound.

EXAMPLE 13

(S)-1-(3,4,5-Trimethoxybenzoyl)-3-(2-(4-phenyl-4-((4-carboxymethylpiperazin-1-yl)carboxamido) piperidin-1-yl)ethyl)-3-(3,4-dichlorophenyl) pyrrolidine

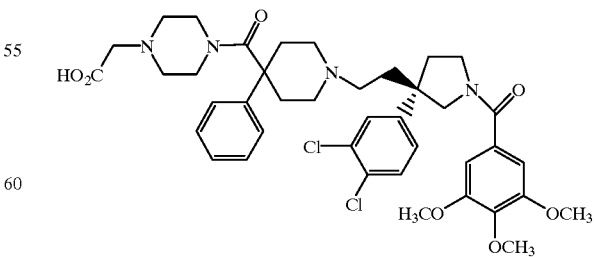

13.1 Synthesis of (R)-1-(3,4,5-trimethoxybenzoyl)-3-(2-(4-phenyl-4-((4-carboxymethylpiperazin-1-yl)carboxamido) piperidine)ethyl)-3-(3,4-dichlorophenyl)pyrrolidine Prepare by the method of Example 9.1 using (S)-1-(3,4,5-trimethoxybenzoyl)-3-(2-(4-phenyl-4-((4-carboethoxymethylpiperazin-1-yl)carboxamido)piperidine)ethyl)-3-(3,4-dichlorophenyl)pyrrolidine hydrochloride salt to give the title compounds.

13.2 Synthesis of (S)-1-3,4,5-trimethoxybenzoyl)-3-(2-(4-phenyl-4-((4-carboxymethyipiperazin-1-yl)carboxamido)piperidine)ethyl)-3-(3,4-dichlorophenyipyrrolidine hydrochloric acid salt Prepare by the method of Example 9.2 using (S)-1-(3,4,5-trimethoxybenzoyl)-3-(2-(4-phenyl-4-((4-carboxymethylpiperazin-1-yl)carboxamido)piperidine)ethyl)-3-(3,4-dichlorophenyl)pyrrolidine to give the title compound.

PREPARATION 6

4-Phenyl-4-(((S)-2-carbomethoxypyrrolidin-1-yl)carboxamido)piperidine hydriodic acid salt Combine 1-t-butoxycarbonyl-4-phenyl-piperidine-4-carboxylic acid (0.64 g, 3.34 mmol) and N,N-diisopropylethylamine (0.58 mL, 6.8 mmol) in dichloromethane (20 mL). Add (S)-2-carbomethoxypyrrolidine hydrochloride (L-proline methyl ester hydrochloride, 0.61 g, 3.67 mmol), 1-(3-dimethylaminopropyl)-3-ethylcarbodiimide hydrochloride (0.70 g, 3.67 mmol), and 1-hydroxybenzotriazole hydrate (0.25 g, 3.67 mmol). After 18 hours, dilute the reaction mixture with dichloromethane and extract twice with water. Dry the organic layer over $MgSO_4$, filter, and evaporate in vacuo to give 1-t-butoxycarbonyl-4-phenyl-4-(((S)-2-carbomethoxypyrrolidin-1-yl)carboxamido)piperidine.

Combine 1-t-butoxycarbonyl-4-phenyl-4-(((S)-2-carbomethoxypyrrolidin-1-yl)carboxamido)piperidine (0.45 g) and dichloromethane (40 mL). Add hydriodic acid (gas, about 1 g). After 3 hours, evaporate in vacuo to give, after drying, the title compound.

EXAMPLE 14

(R)-1-(3,4,5-Trimethoxybenzoyl)-3-(2-(4-phenyl-4-(((S)-2-carbomethoxypyrrolidin-1-yl)carboxamido)piperidin-1-yl)ethyl)-3-(3,4-dichlorophenyl)pyrrolidine

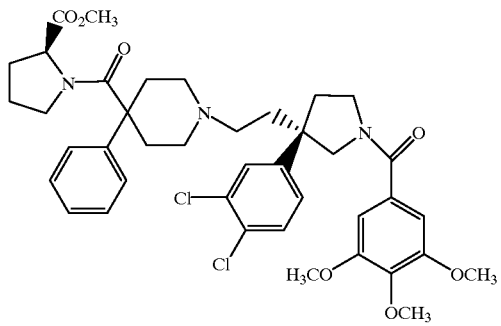

14.1 Synthesis of (R)-1-(3,4,5-trimethoxybenzoyl)-3-(2-(4-phenyl-4-(((S)-2-carbomethoxypyrrolidin-1-yl)carboxamido)piperidin-1-yl)ethyl)-3-(3,4-dichlorophenyl)pyrrolidine Prepare by the method of Example 8.1.1 using (S)-1-(3,4,5-trimethoxybenzoyl)-3-(3,4-dichlorophenyl)-3-(2-methanesulfonyloxyethyl)pyrrolidine and 4-phenyl-4-(((S)-2-carbomethoxypyrrolidin-1-yl)carboxamido)piperidine hydriodic acid salt to give, after chromatograph the residue on silica gel eluting with 10% methanol/ethyl acetate, the title compound. HRMS (FAB+) calculated for $C_{40}H_{48}Cl_2N_3O_7$ 752.286932. Found 752.286459.

EXAMPLE 15

(R)-1-(3,4,5-Trimethoxybenzoyl)-3-(2-(4-phenyl-4-(((S)-2-carboxypyrrolidin-1-yl)carboxamido)piperidin-1-yl)ethyl)-3-(3,4-dichlorophenyl)pyrrolidine

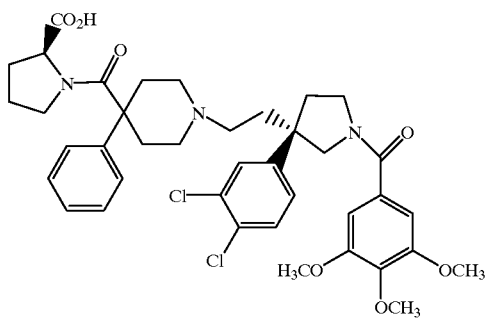

15.1 Synthesis of (R)-1-(3,4,5-trimethoxybenzoyl)-3-(2-(4-phenyl-4-(((S)-2-carboxypyrrolidin-1-yl)carboxamido)piperidin-1-yl)ethyl)-3-(3,4-dichlorophenyl)pyrrolidine Combine (R)-1-(3,4,5-trimethoxybenzoyl)-3-(2-(4-phenyl-4-(((S)-2-carbomethoxypyrrolidin-1-yl)carboxamido)piperidin-1-yl)ethyl)-3-(3,4-dichlorophenyl)pyrrolidine (2.0 g), 1M aqueous sodium hydroxide solution (100 mL, 100 mmol), and methanol 60 mL. After 2 hours, acidify to about pH 4 using 1M aqueous hydrochloric acid solution and extract repeatedly with dichloromethane. Combine the organic layers, dry over $MgSO_4$, filter, and evaporate in vacuo to give the title compound. HRMS (FAB+) calculated for $C_{39}H_{46}Cl_2N_3O_7$ 738.271282. Found 738.270696.

15.2 Synthesis of (R)-1-(3,4,5-trimethoxybenzoyl)-3-(2-(4-phenyl-4-(((S)-2-carboxypyrrolidin-1-yl)carboxamido)piperidin-1-yl)ethyl)-3-(3,4-dichlorophenyl)pyrrolidine hydrochloric acid salt Prepare by the method of Example 5.5 using (R)-1-(3,4,5-trimethoxybenzoyl)-3-(2-(4-phenyl-4-(((S)-2-carboxypyrrolidin-1-yl)carboxamido)piperidin-1-yl)ethyl)-3-(3,4-dichlorophenyl)pyrrolidine to give the title compound.

EXAMPLE 16

1-(3,4,5-Trimethoxybenzoyl)-3-(2-(4-phenyl-4-((4-carboethoxymethylpiperazin-1-yl)carboxamido)piperidin-1-yl)ethyl)-3-phenylpyrrolidine

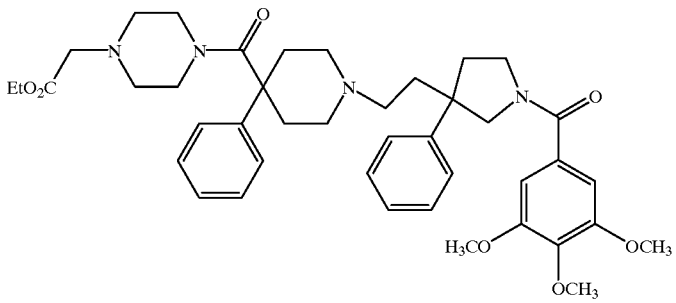

16.1.1 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine hydrochloride salt Combine (R,R)-di-p-anisoyltartaric acid (110 g, 2.62 mmol) in water/methanol (13.6 mL/13.6 mL). Add 12M hydrochloric acid solution (0.217 mL, 2.63 mmol). Add a hot solution of 3-phenyl-3-(2-hydroxyethyl)pyrrolidine (1.0 g, 5.23 mmol) in methanol (13.6 mL). Heat to reflux. After 30 minutes, slowly cool to ambient temperature to give a solid. Collect the solid by filtration and recrystallize the solid twice from methanol/water, once from methanol/2-butanone, and once from ethanol to give (−)-3-phenyl-3-(2-hydroxyethyl)pyrrolidine (R,R)-di-p-anisoyltartaric acid. After conversion of a sample to the 3,4,5-trimethoxybenzamide using sodium carbonate and 3,4,5-trimethoxybenzoyl chloride in acetone/water, analysis on HPLC using a CHIRALPAK AD (10 µm×4.6 cm×250 cm) column eluting with pentane/ethanol/methanol/triethylamine (80/15/5/0.1) with a flow rate of 1.5 mL/minute indicates an enantiomeric excess of 98%, (98% ee), retention time 22.30 minutes for the 3,4,5-trimethoxybenzamide of the isomer prepared from the (−)-isomer of (R,R)-di-p-anisoyltartaric acid salt.

16.1.2 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Add a hot solution of 3-phenyl-3-(2-hydroxyethyl) pyrrolidine (5.0 g, 20.2 mmol) in ethanol (100 mL) to a refluxing solution of (R,R)-di-p-anisoyltartaric acid (16.46 g 20.2 mmol), containing a small amount of acetone) in ethanol (200 mL). After the addition is complete, slowly cool to ambient temperature to give a solid. Collect the solid by filtration and recrystallize the solid three times from ethanol to give (−)-3-phenyl-3-(2-hydroxyethyl)pyrrolidine (R,R)-di-p-anisoyltartaric acid salt: mp; 1716.0–179.0° C. Elemental Analysis calculated for $C_{12}H_{17}NO \cdot C_{20}H_{18}O_{10}$: C 63.05; H 5.79; N 2.30; Found: C 62.72; H 5.80; N 2.33. After conversion of a sample to the 3,4,5-trimethoxybenzamide using sodium carbonate and 3,4,5-trimethoxybenzoyl chloride in acetone/water, analysis on HPLC using a CHIRALPAK AD (10 µm×4.6 cm×250 cm) column eluting with pentane/ethanol/methanol/triethylamine (80/15/5/0.1) with a flow rate of 1.5 mL/minute indicates an enantiomeric excess of 99.9%, (99.9% ee), retention time 22.30 minutes for the 3,4,5-trimethoxybenzamide prepared from the (−)-isomer of (R,R)-di-p-anisoyltartaric acid salt.

Upon standing, the mother liquors from above give a solids Collect the solid by filtration and recrystallize twice from ethanol to give (+)-3-phenyl-3-(2-hydroxyethyl) pyrrolidine (R,R)-di-p-anisoyltartaric acid salt: mp; 175.0–176.0° C. Elemental Analysis calculated for $C_{12}H_{17}NO \cdot C_{20}H_{18}O_{10} \cdot 0.8\ C_3H_6O$: C 62.98; H 6.11; N 2.13; Found: C 62.86; H 5.94; N 2.33. After conversion of a sample to the 3,4,5-trimethoxybenzamide using sodium carbonate and 3,4,5-trimethoxybenzoyl chloride in acetone/water, analysis on HPLC using a CHIRALPAK AD (10 µm×4.6 cm×250 cm) column eluting with pentane/ethanol/methanol/triethylamine (80/15/5/0.1) with a flow rate of 5 mL/minute indicates an enantiomeric excess of 99.9%, (99.9% ee)l retention time 10.26 minutes for the 3,4,5-trimethoxybenzamide prepared from the (+)-isomer of (R,R)-di-p-anisoyltartaric acid salt.

16.1.3 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Combine 3-phenyl-3-(2-hydroxyethyl)pyrrolidine (99.2 g, 659 mmol) and ethanol (2.5 L). Heat to reflux. Add a refluxing solution of (R,R)-di-p-anisoyltartaric acid (212 g, 507 mmol) in ethanol (5.07 L). After the addition is complete, slowly cool to ambient temperature with stirring to give an oil. Dissolve the oil in ethanol at reflux (595 mL) and add a refluxing solution of (R,R)-di-p-anisoyltartaric acid (49.2 g) in ethanol (1.1 L). Cool to ambient temperature with stirring to give a solid. Collect the solid by filtration and recrystallize from ethanol (3.2 L) to give a second solid. Collect the second solid by filtration and recrystallize from ethanol (2.6 L), seed with (−)-3-phenyl-3-(2-hydroxyethyl) pyrrolidine (R,R)-di-p-anisoyltartaric acid salt to give (−)-3-phenyl-3-(2-hydroxyethyl)pyrrolidine (R,R)-di-p-anisoyltartaric acid salt (121 g).

16.1.4 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Combine 3-phenyl-3-(2-hydroxyethyl)pyrrolidine (101 g, 530 mmol) and ethanol (1.92 L). Heat to reflux. Add a refluxing solution of (R,R)-di-p-anisoyltartaric acid (107 g, 410 mmol) in ethanol (3.9 L). Continue to reflux. After 10 minutes, slowly cool to ambient temperature and add seed crystals. After 18 hours, collect the solid that forms by filtration, rinse with ethanol (200 mL). recrystallize twice from ethanol to give (−)-3-phenyl-3-(2-hydroxyethyl) pyrrolidine (R,R)-di-p-anisoyltartaric acid salt: mp; 179–180° C. $[\alpha]_D^{20} = -108.8$ (c=1.02, methanol).

16.14 Synthesis of (+)-3-phenyl-3-(2-hydroxyethyl) pyrrolidine hydrochloric acid salt Combine (−)-3-phenyl-3-(2-hydroxyethyl)pyrrolidine (R,R)-di-p-anisoyltartaric acid salt (30.9 g, 50.7 mmol) and sodium bicarbonate (11.6 g, 53.2 mmol) in tetrahydrofuran/water (200 mL, 5/1). Cool in ice bath and add di-t-butyl dicarbonate (8.52 g, 101 mmol). After 18 hours, evaporate in vacuo to remove most of the tetrahydrofuran. Dilute with ethyl acetate and extract with water, a a saturated aqueous solution of ammonium chloride, a saturated aqueous solution of sodium bicarbonate, and then brine. Dry the organic layer over MgSO$_4$, filter, and evaporate in vacuo to give a residue. Chromatograph the residue on silica gel eluting with 50% ethyl acetate/hexane to give 1-t-butoxycarbonyl-3-phenyl-3-(2-hydroxyethyl)pyrrolidine, prepared from (–)-3-phenyl-3-(2-hydroxyethyl)pyrrolidine (R,R)-di-p-anisoyltartaric acid salt: R$_f$=0.25 (silica gel, 50% ethyl acetate/hexane).

Combine 1-t-butoxycarbonyl-3-phenyl-3-(2-hydroxyethyl)pyrrolidine (13.0 g, 44.6 mmol) and a solution of hydrochloric acid in dioxane (22.3 mL, 4M, 89.2 mmol). Heat to 50° C. After 1 hour, cool and add diethyl ether to give a solid. Collect the solid by filtration to give, after drying, the title compound: mp; 161–163° C. $[\alpha]_D^{20}$=+11.8 (c=0.563, methanol). Elemental Analysis calculated for C$_{12}$H$_{17}$NO•HCl: C 63.29; H 7.97; N 6.15; Found: C 63.21; H 7.86; N 6.05.

16.2.1 Synthesis of 1-(3,4,5-trimethoxybenzoyl)-3-phenyl-3-(2-hydroxyethyl)pyrrolidine Combine (–)-3-phenyl-3-(2-hydroxyethyl)pyrrolidine (R,R)-di-p-anisoyltartaric acid salt (3.95 g, 6.48 mmol) and acetone (20 mL), water (6 mL), and potassium carbonate (2.70 g 19.5 mmol). Cool to 0° C. in an ice bath. After 30 minutes, add dropwise a solution of 3,4,5-trimethoxybenzoyl chloride (1.71 g 7.4 mmol) in acetone (20 mL). Warm to ambient temperature. After 18 hours, partition the reaction mixture between ethyl acetate and saturated aqueous sodium bicarbonate solution. Separate the organic layer and extract with brine. Dry the organic layer over Na$_2$SO$_4$, filters and evaporate in vacuo to give the title compound: R$_f$=0.23 (silica gel, ethyl acetate). Analysis on HPLC using a CHIRALPAK AD (10 μm×4.6 cm×250 cm) column eluting with pentane/ethanol/methanol/triethylamine (80/15/5/0.1) with a flow rate of 15 mL/minute indicates an enantiomeric excess of 98%, (98% ee), retention time of 22.30 minutes.

16.2.2 Synthesis of 1-(3,4,5-trimethoxybenzoyl)-3-phenyl-3-(2-hydroxyethyl)pyrrolidine Combine (–)-3-phenyl-3-(2-hydroxyethyl)pyrrolidine (R,R)-di-p-anisoyltartaric acid salt (56.0 g, 92.1 mmol), sodium carbonate (19.5 g, 184 mmol) in ethyl acetate (2 L) and water (2 L). Cool to about 0° C. in an ice bath. After minutes, slowly add dropwise portionwise 3,4,5-trimethoxybenzoyl chloride (21.2 g, 92.1 mmol). After the addition is completes warm to ambient temperature. After 1 hour, dilute the reaction mixture ethyl acetate and extract with waters 1M aqueous hydrochloric acid solutions and then brine. Dry the organic layer over Na$_2$SO$_4$, filters and evaporate in vacuo to give the title compound.

16.3 Synthesis of 1-(3,4,5-trimethoxybenzoyl)-3-phenyl-3-(2-methanesulfonyloxyethyl)pyrrolidine Prepare by the method of Example 2.5.2 using 1-(3,4,5-trimethoxybenzoyl)-3-phenyl-3-(2-hydroxyethyl) pyrrolidine (prepared from (–)-3-phenyl-3-(2-hydroxyethyl) pyrrolidine (R,R)-di-p-anisoyltartaric acid salt) (2.21 g, 5.51 mmol) and methanesulfonyl chloride (0.7 mL, 9.0 mmol) to give the title compound: R$_f$=0.47 (silica gel, ethyl acetate).

16.4 Synthesis of 1-(3,4,5-trimethoxybenzoyl)-3-(2-(4-phenyl-4-((4-carboethoxymethylpiperazin-1-yl)carboxamido)piperidin-1-yl)ethyl)-3-phenylpyrrolidine Prepare by the method of Example 8.1.1 using 1-(3,4,5-trimethoxybenzoyl)-3-phenyl-3-(2-methanesulfonyloxyethyl)pyrrolidine (prepared from (–)-3-phenyl-3-(2-hydroxyethyl)pyrrolidine (R,R)-di-p-anisoyltartaric acid salt) and 4-phenyl-4-((4-carboethoxymethylpiperazin-1-yl)carboxamido)piperidine hydriodic acid salt to give the title compound.

EXAMPLE 17

1-(3,4,5-Trimethoxybenzoyl)-3-(2-(4-phenyl-4-((4-carboxymethylpiperazin-1-yl)carboxamido) piperidin-1-yl)ethyl)-3-phenylpyrrolidine

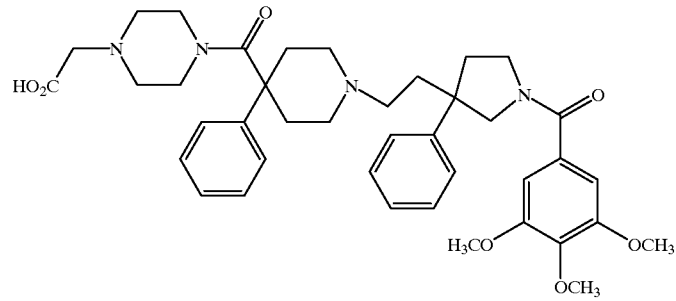

17.1 Synthesis of 1-(3,4,5-trimethoxybenzoyl)-3-(2-(4-phenyl-4-((4-carboxymethylpiperazin-1-yl)carboxamido) piperidin-1-yl)ethyl)-3-phenylpyrrolidine Prepare by the method of Example 9.1 using 1-(3,4,5-trimethoxybenzoyl)-3-(2-(4-phenyl-4-((4-carboethoxymethylpiperazin-1-yl)carboxamido)piperidin-1-yl)ethyl)-3-phenylpyrrolidine (prepared from (–)-3-phenyl-3-(2-hydroxyethyl)pyrrolidine (R,R)-di-p-anisoyltartaric acid salt) to give the title compound.

PREPARATION 7

2-Methoxy-5-(4H-triazol-4-yl)benzoyl chloride

According to the method of J. Chem. Soc. (C), 1664 (1967), combine methyl 2-methoxy-5-aminobenzoate (2.0 g 11 mmol), N,N-dimethylformamide azine (1.56 g, 11 mmol), p-toluenesulfonic acid (190 mg) in toluene (25 mL). Fit the reaction vessel with a gas inlet such that the head space of the vessel is swept with argon and scrub the effluent through dilute aqueous hydrochloric acid solution. Heat to reflux. After 20 hours, concentrate the reaction mixture in vacuo to give a residue. Partition the residue between dichloromethane and a saturated aqueous sodium bicarbonate solution. Extract the aqueous layer twice with dichloromethane. Combine the organic layers, dry over MgSO$_4$, filter, and evaporate invacubo to give a residue. Chromatograph the residue on silica gel eluting sequentially with 70% ethyl acetate/dichloromethane and then 5% methanol/dichloromethane to give a residue. Recrystallize the residue form ethyl acetate/hexane to give methyl 2-methoxy-5-(4H-triazol-4-yl)benzoate. mp; 191–195.5° C.

Alternately, according to the method of *J. Med. Chem.*, 21, 1100 (1978), combine methyl 2-methoxy-5-aminobenzoate (1.8 g, 10 mmol), diformyl hydrazine (0.97 g, 11 mmol), and phosphorous pentoxide (1.84 g, 13 mmol). Heat to 160° C. After 1.5 hours, cool the reaction mixture and add a saturated aqueous solution of sodium bicarbonate. Extract three times with dichloromethane. Dry the combined organic layers over MgSO$_4$, filter, and evaporate in vacuo to give a residues Chromatograph the residue on silica gel eluting sequentially with 40% ethyl acetate/dichloromethane and then 5% methanol/dichloromethane to give methyl 2-methoxy-5-(4H-triazol-4-yl)benzoate: mp; 179–182° C.

Combine methyl 2-methoxy-5-(4H-triazol-4-yl)benzoate (56 mmol) and methanol (200 mL) and water (50 mL). Add 1M aqueous solution of sodium hydroxide (62.5 mL, 62.5 mmol). Heat to reflux. After 8 hour, concentrate in vacuo to remove most of the solvent. Adjust the pH to about 1 to 2 using a 1M aqueous hydrochloric acid solution, extract with a saturated dichloromethane. Dry the organic layer over MgSO$_4$, filter, and evaporate in vacuo to give 2-methoxy-5-(4H-triazol-4-yl)benzoic acid.

Combine 2-methoxy-5-(4H-triazol-4-yl)benzoic acid (5.5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

18.1 Synthesis of (S)-1-(2-methoxy-5-(tetrazol-1-yl)benzoyl)-(3-(3,4-dichlorophenyl)-3-(2-hydroxyethyl)pyrrolidine Prepare be the method of Example 10.1 using (S)-3-(3,4-dichlorophenyl)-3-(2-hydroxyethyl)pyrrolidine (R,R)-di-p-anisoyltartaric acid salt and 2-methoxy-5-(4H-triazol-4-yl)benzoyl chloride to give the title compound.

18.2 Synthesis of (S)-1-(2-methoxy-5-(4H-triazol-4-yl)benzoyl)-3-(3,4-dichlorophenyl)-3-(2-methanesulfonyloxyethyl)pyrrolidine Prepare by the method of Example 2.5.2 using (S)-1-(2-methoxy-5-(4H-triazol-4-yl)benzoyl)-3-(3,4-dichlorophenyl)-3-(2-hydroxyethyl)pyrrolidine and methanesulfonyl chloride to give the title compound.

18.3 Synthesis of (R)-1-(2-methoxy-5-(4H-triazol-4-yl)benzoyl)-3-(2-(4-phenyl-4-(4-carboethoxymethyl piperazin-1-yl)carboxamidopiperidine)ethyl)-3-(3,4-dichlorophenyl)pyrrolidine Prepare by the method of Example 10.3 using (S)-1-(2-methoxy-5-(4H-triazol-4-yl)benzoyl)-3-(3,4-dichlorophenyl)-3-(2-methanesulfonyloxyethyl)pyrrolidine and 4-phenyl-4-((4-carboethoxymethylpiperazin-1-yl)carboxamido)piperidine hydriodic acid salt to give the title compound.

EXAMPLE 18

(R)-1-(2-Methoxy-5-(4H-triazol-4-yl benzoyl)-3-(2-(4-phenyl-4-((4-carboethoxymethylpiperazin-1-yl)carboxamido)piperidin-1-yl)ethyl)-3-(3,4-dichlorophenyl)pyrrolidine

EXAMPLE 19

(R)-1-(2-Methoxy-5-(4H-triazol-4-yl)benzoyl)-3-(2-(4-phenyl-4-((4-carboxymethylpiperazin-1-yl)carboxamido)piperidin-1-yl)ethyl)-3-(3,4-dichlorophenyl)pyrrolidine

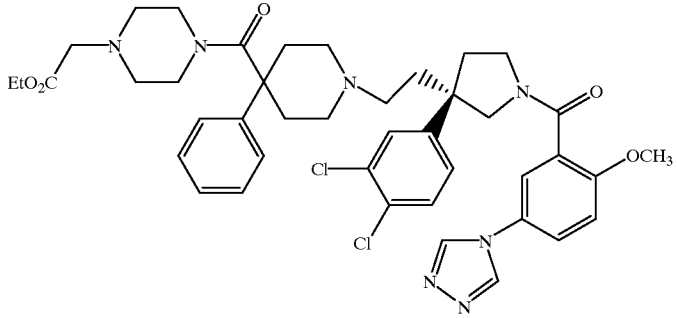

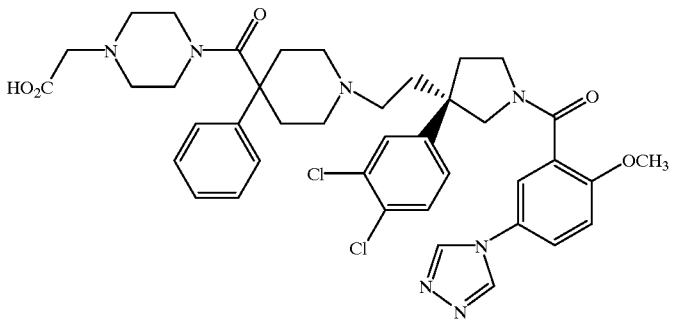

19.1 Synthesis of (R)-1-(2-methoxy-5-(4H-triazol-4-yl)benzoyl)-3-(2-(4-phenyl-4-((4-carboxymethyl piperazin-1-yl)carboxamido)piperidine)ethyl)-3-(3,4-dichlorophenyl)pyrrolidine Prepare by the method of Example 9.1 using (R)-1-(2-methoxy-5-(4H-triazol-4-yl)benzoyl)-3-(2-(4-phenyl-4-((4-carboethoxymethyl piperazin-1-yl)carboxamido)piperidine)ethyl)-3-(3,4-dichlorophenyl)pyrrolidine to give the title compound.

PREPARATION 8

2-Methoxy-5-(1H-tetrazol-5-yl)benzoyl chloride

Combine methyl 2-methoxy-5-formylbenzoate (5.0 g, 25.9 mmol), hydroxylamine hydrochloride (8.55 g, 133 mmol), and sodium acetate (10.25 g, 125 mmol) in ethanol/water (200 mL, 1/1). Heat to 50° C. After 1 hour, pour the reaction mixture onto ice to give a solid. Collect the solid by filtration to give methyl 2-methoxy-5-formylbenzoate oxime: $R_f$=0.76 (silica gel, 9/1 dichloromethane/methanol).

Combine methyl 2-methoxy-5-formylbenzoate oxime (3.5 g, 16.7 mmol) in dichloromethane (75 mL) and cool in an ice-bath. Add dropwise thionyl chloride (2.0 mL, 27.2 mmol). after 20 minutes, dilute the reaction mixture with dichloromethane and extract with a saturated aqueous solution of sodium bicarbonate and then brine. Dry the organic layer over MgSO$_4$, filter, and concentrate in vacuo to give a residue. Chromatograph the residue on silica gel eluting with 1/1 ethyl acetate/hexane to give methyl 2-methoxy-5-cyanobenzoate.

Combine methyl 2-methoxy-5-cyanobenzoate (0.67 mmol), sodium azide (0.13 g, 2.04 mmol), and triethylammonium hydrochloride (0.14 g, 1.03 mmol) in N-methylpyrrolidinone (6 mL). Heat to 150° C. After 4 hours, cool to ambient temperature and partition the reaction mixture between water and ethyl acetate. Separate the layers and extract the aqueous layer three times with ethyl acetate. Adjust the pH of the aqueous layer to about 1 using a 1M aqueous hydrochloric acid solution, The aqueous layer is again extracted three times with ethyl acetate, and twice with dichloromethane. The aqueous layer is saturated with sodium chloride and again extracted four times with dichloromethane. Combine the organic layers, dry over MgSO$_4$, filter, and evaporate in vacuo to give methyl 2-methoxy-5-(1H-tetrazol-5-yl)benzoate.

Combine methyl 2-methoxy-5-(1H-tetrazol-5-yl)benzoate (1 mmol) and lithium hydroxide (1.1 mmol) in 1/1 tetrahydrofuran/water (5 mL). After 24 hours, dilute the reaction mixture with a 0.5M aqueous hydrochloric acid solution and dichloromethane. Separate the layers and extract the aqueous layer three times with dichloromethane. Combine the organic layers, dry over MgSO$_4$, filter, and evaporate in vacuo to give 2-methoxy-5-(1H-tetrazol-5-yl)benzoic acid.

Combine 2-methoxy-5-(1H-tetrazol-5-yl)benzoic acid (5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

EXAMPLE 20

(R)-1-(2-Methoxy-5-(1H-tetrazol-5-yl)benzoyl)benzoyl)-3-(2-(4-phenyl-4-((4-carboxymethylpiperazin-1-yl)carboxamido)piperidin-1-yl)ethyl)-3-(3,4-dichlorophenyl)pyrrolidine

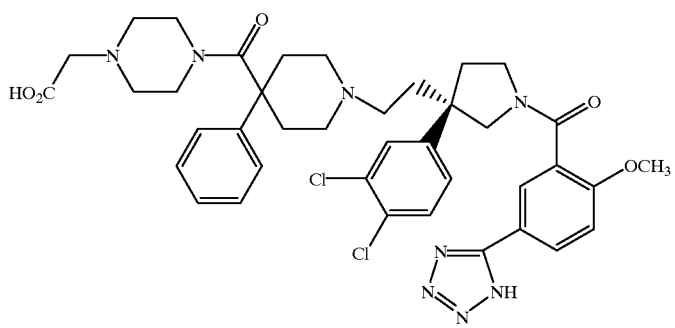

20.1 Synthesis of (S)-1-(2-methoxy-5-(1H-tetrazol-5-yl)benzoyl)-3-(3,4-dichlorophenyl)-3-(2-hydroxyethyl)pyrrolidine Prepare by the method of Example 10.1 using (S)-3-(3,4-dichlorophenyl)-3-(2-hydroxyethyl)pyrrolidine (R,R)-di-p-anisoyltartaric acid salt and 2-methoxy-5-(1H-tetrazol-5-yl)benzoyl chloride to give the title compound.

20.2 Synthesis of (S)-1-(2-methoxy-5-(1H-tetrazol-5-yl)benzoyl)-3-(3,4-dichlorophenyl)-3-(2-methanesulfonyloxyethyl)pyrrolidine Prepare by the method of Example 2.5.2 using (S)-1-(2-methoxy-5-(1H-tetrazol-5-yl)benzoyl)-3-(3,4-dichlorophenyl)-3-(2-hydroxyethyl)pyrrolidine and methanesulfonyl chloride to give the title compound.

20.3 Synthesis of (R)-1-(2-methoxy-5-(1H-tetrazol-5-yl)benzoyl)-3-(2-(4-phenyl-4-((4-carboethoxymethyl piperazin-1-yl)carboxamido)piperidine)ethyl)-3-(3,4-dichlorophenyl)pyrrolidine Prepare by the method of Example 10.3 using (S)-1-(2-methoxy-5-(1H-tetrazol-5-yl)benzoyl)-3-( 3,4-dichlorophenyl)-3-(2-methanesulfonyloxyethyl)pyrrolidine (1.0 g, 1.62 mmol) and 4-phenyl-4-((4-carboethoxymethylpiperazin-1-yl)carboxamido)piperidine hydriodic acid salt to give the title compound.

20.4 Synthesis of (R)-1-(2-methoxy-5-(1H-tetrazol-5-yl)benzoyl)-3-(2-(4-phenyl-4-((4-carboxymethyl piperazin-1-yl)carboxamido)piperidine)ethyl)-3-(3,4-dichlorophenyl)pyrrolidine Prepare by the method of Example 9.1 using (R)-1-(2-methoxy-5-(1H-tetrazol-5-yl)benzoyl)-3-(2-(4-phenyl-4-((4-carboethoxymethyl piperazin-1-yl)carboxamido)piperidine)ethyl)-3-(3,4-dichlorophenyl)pyrrolidine to give the title compound.

EXAMPLE 21

(R)-1-(3,4,5-Trimethoxybenzoyl)-3-(2-(4-phenyl-4-((4-carboethoxypiperidin-1-yl)carboxamido)piperidin-1-yl)ethyl-3-(3,4-dichlorophenyl)pyrrolidine 21.1 Synthesis of (R)-1-(3,4,5-trimethoxybenzoyl)-3-(2-(4-phenyl-4-((4-carboethoxypiperidin-1-yl)carboxamido)piperidin-1-yl)ethyl)-3-(3,4-dichlorophenyl)pyrrolidine Prepare by the method of Example 8.1.1 using (S)-1-(3,4,5-trimethoxybenzoyl)-3-(3,4-dichlorophenyl)-3-(2-methanesulfonyloxyethyl)pyrrolidine and 4-phenyl-4-((4-carboethoxypiperidin-1-yl)carboxamido)piperidine hydrochloric acid salt to give, after chromatography on silica gel eluting with 3% methanol/dichloromethane, the title compound: $R_f$=0.40 (silica gel, 6% methanol/dichloromethane).

21.2 Synthesis of (R)-1-(3,4,5-trimethoxybenzoyl)-3-(2-(4-phenyl-4-((4-carboethyoxypiperidin-1-yl)carboxamido)piperidin-1-yl)ethyl)-3-(3,4-dichlorophenyl)pyrrolidine hydrochloric acid salt Combine (R)-1-(3,4,5-trimethoxybenzoyl)-3-(2-(4-phenyl-4-((4-carboethoxypiperidin-1-yl)carboxamido)piperidin-1-yl)ethyl)-3-(3,4-dichlorophenyl)pyrrolidine (3.1 g) and dichloromethane (100 mL). Add hydrochloric acid (gas) in a steady stream for about 10 minutes. Evaporate in vacuo to solid. Collect the solid and dry to give the title compound. Elemental Analysis calculated for $C_{42}H_{51}Cl_2N_3)_7$•HCl•1.1 H$_2$O: C, 59.94; H, 6.53; N, 5.02. Found C. 59.92; H, 6.40; N, 4.86.

EXAMPLE 22

(R)-1-(3,4,5-Trimethoxybenzoyl)-3-(2-(4-phenyl-4-((4-carboxypiperidin-1-yl)carboxamido)piperidin-1-yl)ethyl)-3-(3,4-dichlorophenyl]pyrrolidine

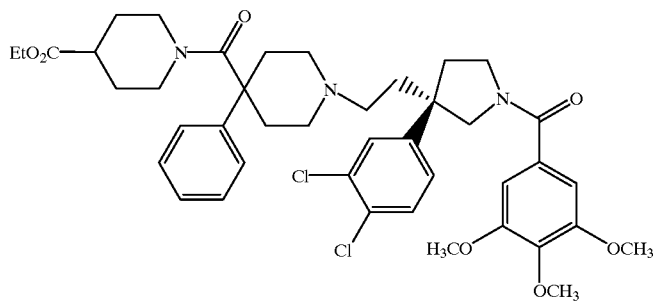

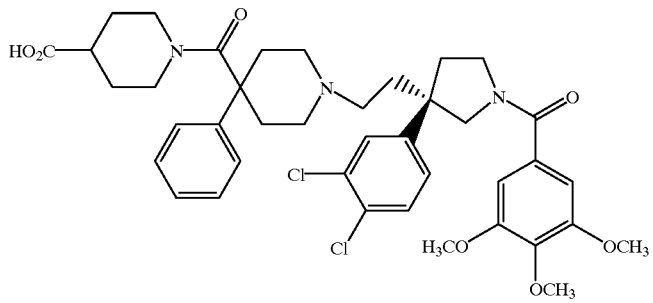

22.1 Synthesis of (R)-1-(3,4,5-trimethoxybenzoyl)-3-(2-(4-phenyl-4-((4-carboxypiperidin-1-yl)carboxamido)piperidin-1-yl)ethyl)-3-(3,4-dichlorophenyl)pyrrolidine hydrochloric acid salt Combine (R)-1-(3,4,5-trimethoxybenzoyl)-3-(2-(4-phenyl-4-((4-carboethoxypiperidin-1-yl)carboxamido)piperidin-1-yl)ethyl)-3-(3,4-dichlorophenyl)pyrrolidine hydrochloric acid salt (0.65 g, 0.8 mmol) tetrahydrofuran (15 mL) and water (15 mL). Add lithium hydroxide (0.11 g, 4.8 mmol). After 2 hours, adjust the pH to about 6 using a 1M aqueous hydrochloric acid solution and evaporate in vacuo to remove most of the tetrahydrofuran. Dilute the evaporated reaction mixture with brine and extract twice with dichloromethane. Dry the combined organic layers over MgSO$_4$, filter, and evaporate in vacuo to give a residues Combine the residue and dichloromethane (100 mL). Add hydrochloric acid (gas, about 13 g) to give a solid. Collect the solid and dry to give the title compound.

EXAMPLE 23

1-(3,4,5-Trimethoxybenzoyl)-3-(2-(4-phenyl-4-((4-carboethoxymethylpiperazin-1-yl)carboxamido)piperidin-1-yl)ethyl)-3-(3,4-difluorophenyl)pyrrolidine

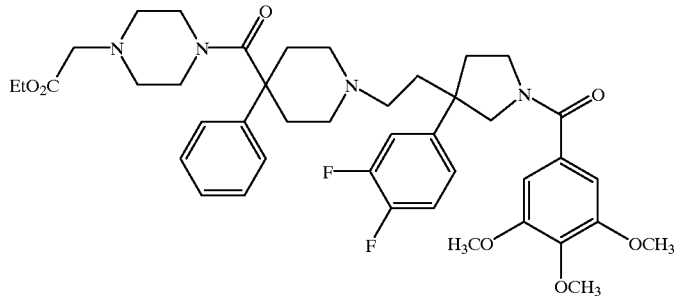

23.1 Synthesis of 3-cyano-3-(3,4-difluorophenyl)pentanedioic acid diethyl ester Prepare by the method of Example 3.1.2 using 3,4-difluorophenylacetonitrile to give the title compound.

23.2.1 Synthesis of (3-(3,4-difluorophenyl)-5-oxopyrrolidin-3-yl)acetic acid ethyl ester Prepare by the method of Example 2.2.2 using 3-cyano-3-(3,4-difluorophenyl)pentanedioic acid diethyl ester to give the title compound.

23.2.2 Synthesis of (3-(3,4-difluorophenyl)-5-oxopyrrolidin-3-yl)acetic acid ethyl ester Combine 3-cyano-3-(3,4-difluorophenyl)pentanedioic acid diethyl ester (106 g 326 mmol), ethanol (3 L), concentrated aqueous ammonia (160 mL), and Raney nickel (100 g). Hydrogenate at about 50° C. and 200 psi in an autoclave. After 22 hours, filter through celite and rinse the solids with ethanol. Evaporate the filtrate in vacuo to give a residue. Triturate the residue with ethyl acetate/hexane to give the title compound.

23.3 Synthesis of 3-(3.4-difluorophenyl)-3-(2-hydroxyethyl)pyrrolidine

Prepare by the method of Example 2.3 using (3-(3,4-difluorophenyl)-5-oxopyrrolidin-3-yl)acetic acid ethyl ester to give the title compound: R$_f$=0.26 (silica gel, 85/10/5 dichloromethane/methanol/acetic acid).

23.4.1 Resolution of (+)-3-(3,4-difluorophenyl)-3-(2-hydroxyethyl)pyrrolidine (R,R)-di-p-anisoyltartaric acid salt and (−)-3-(3,4-difluorophenyl)-3-(2-hydroxyethyl)pyrrolidine hydrochloric acid salt Combine (R,R)-di-p-anisoyltartaric acid (0.93 g, 2.2 mmol) and aqueous 12M hydrochloric acid solution (0.19 mL, 2.28 mmol) in water/methanol (10 mL)/(10 mL). Heat to reflux. Add dropwise, a solution of 3-(3,4-difluorophenyl)-3-(2-hydroxyethyl)pyrrolidine (0 g, 4.4 mmol) in methanol (10 mL). After 15 minutes, slowly cool to ambient temperatures Filter the solid that forms and rinse with water to give (−)-3-(3,4-difluorophenyl)-3-(2-hydroxyethyl)pyrrolidine (R,R)-di-p-anisoyltartaric acid salt. $[\alpha]^2_D{}^0$=−25.1 (c=1.02, dimethylsulfoxide). Analysis on HPLC, on an analytical sample of the free amine obtained by extractions using a CHIRALPAK AD 25 cm×0.46 cm column eluting with pentane/methanol/triethylamine (80/10/0.1) with a flow rate of 1.0 mL/minute indicates an enantiomeric excess of 97.8%, (97.8% ee), retention time 19.0 minutes for the 3,4,5-trimethoxybenzamide prepared from the (−)-isomer of the (R,R)-di-p-anisoyltartaric acid salt, retention time 12.5 minutes for the 3,4,5-trimethoxybenzamide prepared from the (+)-isomer of the (R,R)-di-p-anisoyltartaric acid salt.

23.4.2 Resolution of (+)-3-(3,4-difluorophenyl)-3-(2-hydroxyethyl)pyrrolidine (R,R)-di-p-anisoyltartaric acid salt and (−)-3-(3,4-difluorophenyl)-3-(2-hydroxyethyl) pyrrolidine hydrochloric acid salt Combine (R,R)-di-p-anisoyltartaric acid (6.6 g, 15.8 mmol) and water/methanol (70 mL)/(70 mL). Heat to reflux. Add aqueous 12M hydrochloric acid solution (1.31 mL, 15.7 mmol). Add dropwise, a solution of 3-(3,4-difluorophenyl)-3-(2-hydroxyethyl)pyrrolidine (7.15 g, 31.5 mmol) in methanol (70 mL). After 15 minutes, allow to cool slightly and add seed crystals of (−)-3-(3,4-difluorophenyl)-3-(2-hydroxyethyl)pyrrolidine (R,R)-di-p-anisoyltartaric acid salt and then slowly cool to ambient temperature. Filter the solid that forms. Retain the filtrate which is enriched in the slower eluting isomer. Combine the solid with hot ethanol (800 mL), filters reduce the volume of the solution to about 600 mL and slowly cool to ambient temperature to give a solid. Collect the solid by filtration and dry in vacuo at 82° C. to give (−)-3-(3,4-difluorophenyl)-3-(2-hydroxyethyl) pyrrolidine (R,R)-di-p-anisoyltartaric acid salt. Analysis on HPLC, on an analytical sample of the 3,4,5-trimethoxybenzamide derivative using a CHIRALPAK AD 25 cm×0.46 cm column eluting with pentane/ethanol/methanol/triethylamine (80/15/5/0.1) with a flow rate of 1.0 mL/minute indicates an enantiomeric excess of greater than 99%, (>99% ee).

23.5 Synthesis of 1-(3,4,5-trimethoxybenzoyl)-3-(3,4-difluorophenyl)-3-(2-hydroxyethyl)pyrrolidine Prepare by the method of Example 5.2.2 using (−)-3-(3,4-difluorophenyl)-3-(2-hydroxyethyl)pyrrolidine (R,R)-di-p-anisoyltartaric acid salt.

23.6 Synthesis of 1-(3,4,5-trimethoxybenzoyl)-3-(3,4-difluorophenyl)-3-(2-methanesulfonyloxyethyl)pyrrolidine Prepare by the method of Example 2.5.2 using 1-(3,4,5-trimethoxybenzoyl)-3-(3,4-difluorophenyl)-3-(2-hydroxyethyl)pyrrolidine (prepared from (−)-3-(3,4-difluorophenyl)-3-(2-hydroxyethyl)pyrrolidine (R,R)-di-p-anisoyltartaric acid salt) to give the title compound.

23.7 Synthesis of 1-(3,4,5-trimethoxybenzoyl)-3-(2-(4-phenyl-4-((4-carboethoxymethylpiperazin-1-yl) carboxamido)piperidin-1-yl)ethyl)-3-(3,4-difluorophenylpyrrolidine Combine 1-(3,4,5-trimethoxybenzoyl)-3-(3,4-difluorophenyl)-3-(2-methanesulfonyloxyethyl)pyrrolidine (prepared from (−)-3-(3,4-difluorophenyl)-3-(2-hydroxyethyl)pyrrolidine (R,R)-di-p-anisoyltartaric acid salt) (0.4 g, 1.0 mmol), potassium carbonate (0.33 g, 2.4 mmol) and 4-phenyl-4-((4-carboethoxymethylpiperazin-1-yl)carboxamido)piperidine hydrochloric acid salt (0.4 g, 0.8 mmol) in tetrahydrofuran/water (6 mL/2 mL). Heat to reflux. After 64 hours, evaporate in vacuo to give a residue. Combine the residue and dichloromethane and extract with a saturated aqueous solution of sodium bicarbonate. Dry the organic layer over MgSO$_4$, filter, and evaporate in vacuo to give a residue. Chromatograph the residue on silica gel eluting sequentially with ethyl acetate, 1% methanol/dichloromethane, 2% methanol/dichloromethane 3% methanol/dichloromethane, 4% methanol/dichloromethane, and then 5% methanol/dichloromethane to give the title compound.

23.8 Synthesis of 1-(3,4,5-trimethoxybenzoyl)-3-(2-(4-phenyl-4-((4-carboethoxymethylpiperazin-1-yl) carboxamido)piperidin-1-yl)ethyl)-3-(3,4-difluorophenyl) pyrrolidine hydrochloric acid salt Combine 1-(3,4,5-trimethoxybenzoyl)-3-(2-(4-phenyl-4-((4-carboethoxymethylpiperazin-1-yl)carboxamido) piperidin-1-yl)ethyl)-3-(3,4-difluorophenyl)pyrrolidine (0.38 g, 0.45 mmol) and dichloromethane. Purge with hydrochloric acid (gas) for about 5 minutes. Evaporate in vacuo to give, after drying, the title compound.

EXAMPLE 24

1-(3,4,5-Trimethoxybenzoyl)-3-(2-(4-phenyl-4-((4-carboxymethylpiperazin-1-yl)carboxamido) piperidin-1-yl)ethyl)-3-(3,4-difluorophenyl) pyrrolidine

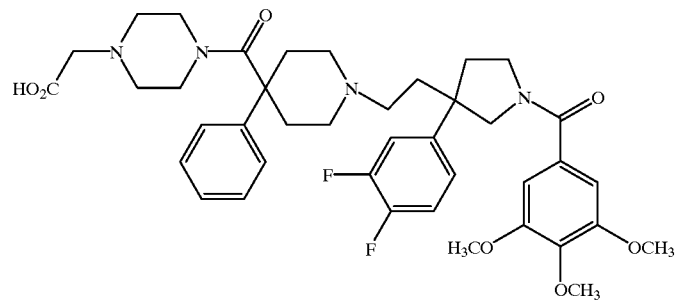

24.1 Synthesis of 1-(3,4,5-trimethoxybenzoyl)-3-(2-(4-phenyl-4-((4-carboxymethylpiperazin-1-yl carboxamido) piperidin-1-yl)ethyl)-3-(3,4-difluorophenyl)pyrrolidine Prepare by the method of Example 9.1 using 1-(3,4,5-trimethoxybenzoyl)-3-(2-(4-phenyl-4-((4-carboethoxymethylpiperazin-1-yl)carboxamido)piperidin-1-yl)ethyl)-3-(3,4-difluorophenyl)pyrrolidine to give the title compound.

EXAMPLE 25

(R)-1-(3,4,5-Trimethoxybenzoyl)-3-(2-(4-phenyl-4-((2-carboethoxymorpholin-4-yl)carboxamido) piperidin-1-yl)ethyl)-3-(3,4-dichlorophenyl) pyrrolidine

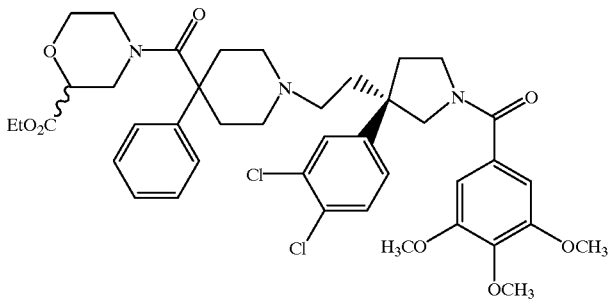

25.1 Synthesis of (R)-1-(3,4,5-trimethoxybenzoyl)-3-(2-(4-phenyl-4-(2-carboethoxymorpholin-4-yl)carboxamido) piperidin-1-yl)ethyl)-3-(3,4-dichlorophenyl)pyrrolidine Combine (S)-1-(3,4,5-trimethoxybenzoyl)-3-(3,4-dichlorophenyl)-3-(2-methanesulfonyloxyethyl)pyrrolidine (2 g), 4-phenyl-4-((2-carboethoxymorpholin-4-yl) carboxamido) piperidine hydrochloric acid salt (5 mmol), and N,N-diisopropylethylamine (3 mL) in acetonitrile (25 mL). Heat to reflux After 10 hours, evaporate in vacuo to give a residue. Chromatograph the residue on silica gel eluting sequentially with ethyl acetate and then 95/5 dichloromethane/ methanol to give the title compound. $R_f$=0.50 (silica gel, dichloromethane/methanol, 9/1) and $R_f$=0.20 (silica gel, ethyl acetate/methanol 9/1).

25.2 Synthesis of (R)-1-(3,4,5-trimethoxybenzoyl)-3-(2-(4-phenyl-4-((2-carboethoxymorpholin-4-yl)carboxamido) piperidin-1-yl)ethyl)-3-(3,4-dichlorophenyl)pyrrolidine fumaric acid salt Combine (R)-1-(3,4,5-trimethoxybenzoyl)-3-(2-(4-phenyl-4-((2-carboethoxymorpholin-4-yl)carboxamido) piperidin-1-yl)ethyl)-3-(3,4-dichlorophenyl)pyrrolidine (0.8 g, 1.06 mmol) and fumaric acid (184 mg, 1.6 mmol) in ethanol (10 mL) After 10 minutes evaporate in vacuo to give a residue. Triturate the residue with diethyl ether to give a solid. Collect the solid, rinse with diethyl etherg and dry to give the title compound: mp; 125–128° C.

EXAMPLE 26

(R)-1-(3,4,5-Trimethoxybenzoyl)-3-(2-(4-phenyl-4-((2-carboxymorpholin-4-yl)carboxamido)piperidin-1-yl)ethyl)-3-(3,4-dichlorophenyl)pyrrolidine

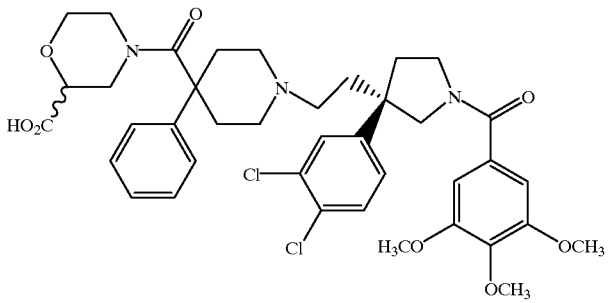

26.1 Synthesis of (R)-1-(3,4,5-trimethoxybenzoyl)-3-(2-(4-phenyl-4-((2-carboxymorpholin-4-yl)carboxamido) piperidin-1-yl)ethyl)-3-(3,4-dichlorophenyl)pyrrolidine Combine (R)-1-(3,4,5-trimethoxybenzoyl)-3-(2-(4-phenyl-4-((2-carboethoxymorpholin-4-yl)carboxamido) piperidin-1-yl)ethyl)-3-(3,4-dichlorophenyl)pyrrolidine (0.77 g, 1.02 mmol) and lithium hydroxide hydrate (128 mg, 3.06 mmol) in tetrahydrofuran/methanol/water (2/2/1, 15 mL). After 1 hour evaporate in vacuo to give a residue, combine the residue and water, acidify with aqueous 1M hydrochloric acid solution, and extract five times with dichloromethane. Combine the organic layers, dry over $Na_2SO_4$, filter, and evaporate in vacuo to give a residue. Chromatograph the residue, eluting sequentially with 1% methanol/dichloromethane and then 5% methanol/dichloromethane to give the title compound. $R_f$=0.30 (silica gel, 25% methanol/dichloromethane).

PREPARATION 9

4-Phenyl-4-((4-carboethoxyethylpiperazin-1-yl) carboxamido)piperidine hydriodic acid salt Combine t-butyl 1-piperazinecarboxylate (10.47 g, 56.2 mmol), ethyl acrylate (8 mL) in ethanol (30 mL). Heat at reflux. After 5.5 hours, cool the reaction mixture and evaporate in vacuo to give a residue. Combine the residue and diethyl ether (200 mL) and extract with a 1M aqueous solution of hydrochloric acid. Adjust the pH of the aqueous layer to basic using sodium bicarbonate and then extract with ethyl acetate. Dry the organic layer over $MgSO_4$, filter, and evaporate in vacuo to give t-butyl 4-carboethoxyethyl-1-piperazinecarboxylate.

Combine t-butyl 4-carboethoxyethyl-1-piperazinecarboxylate (14.3 g, 50 mmol) and dichloromethane (250 mL). Stir, cool to about 0° C. and purge with hydrochloric acid gas. After 4 hours, concentrate the reaction mixture in vacuo, twice add diethyl ether (200 mL) and evaporate in vacuo to give a solid. Triturate the solid with diethyl ether and collect by filtration to give 4-carboethoxyethyl-1-piperazine hydrochloric acid salt.

Combine 4-carboethoxyethyl-1-piperazine hydrochloric acid salt (6.8 g, 26.2 mmol), 1-t-butoxycarbonyl-4-phenylpiperidine-4-carboxylic acid (8.0 g, 26.2 mmol), N,N-diisopropylethylamine (14 mL), and 1-hydroxybenzotriazole hydrate (3.9 g) in dichloromethane (250 mL). Add 1-(3-dimethylaminopropyl)-3-ethylcarbodiimide hydrochloride (5.53 g). After 17 hours, dilute the reaction mixture with dichloromethane (300 mL) and extract with a saturated aqueous solution of sodium bicarbonate, water, and then a 1M aqueous solution of hydrochloric acid. Dry the organic layer over MgSO$_4$, filter, and evaporate in vacuo to give a residue. Chromatograph the residue on silica gel eluting sequentially with hexane, 20% ethyl acetate/hexane, 30% ethyl acetate/hexane, 50% ethyl acetate/heaxne, 60% ethyl acetate/hexane, 50% ethyl acetate/hexane containing 2.0 mL of triethylamine, and then ethyl acetate to give 1-t-butoxycarbonyl-4-phenyl-4-((4-carboethoxyethylpiperazin-1-yl)carboxamido)piperidine.

Combine 1-t-butoxycarbonyl-4-phenyl-4-((4-carboethoxyethylpiperazin-1-yl)carboxamido)piperidine (7.3 gb, 15.3 mmol) and dichloromethane (250 mL). Stir, cool to about 0° C. and purge with hydrochloric acid gas. After 2 hours, warm to ambient temperature and purge again with hydrochloric acid gas. After 3 hours, concentrate the reaction mixture in vacuo, three times add diethyl ether (50 mL) and evaporate in vacuo to give a solid. Combine the solids dichloromethane (100 mL), and an aqueous solution of sodium bicarbonate. Separate the layers, saturate the aqueous layer with sodium chlorides and extract twice with dichloromethane. Combine the organic layers, dry over MgSO$_4$, filters and evaporate in vacuo to give 4-phenyl-4-((4-carboethoxyethylpiperazin-1-yl)carboxamido) piperidine.

Combine 4-phenyl-4-((4-carboethoxyethylpiperazin-1-yl)carboxamido)piperidine (6.0 g) and ethanol (60 mL). Add an aqueous solution of hydriodic acid (7.9 g 57%). After 30 minutes, add diethyl ether (200 mL) to give a solid. Filter, rinse the solid with diethyl ether, and dry to give the title compound.

Combine (S)-1-(3,4,5-trimethoxybenzoyl)-3-(3,4-dichlorophenyl)-3-(2-methanesulfonyloxyethyl)pyrrolidine (3.72 g) 4-phenyl-4-((4-carboethoxyethylpiperazin-1-yl) carboxamido)piperidine hydriodic acid salt (4.0 g, 6.36 mmol), and triethylamine (2.7 mL) in acetonitrile (40 mL). Heat to reflux. After 6 hours, cool the reaction mixture, concentrate in vacuo, and dilute with dichloromethane (200 mL). Extract with saturated aqueous sodium bicarbonate and then water. Dry the organic layer over MgSO$_4$, filter, and evaporate in vacuo to give residue. Chromatograph the residue on silica gel eluting sequentially with ethyl acetate, 2% methanol/ethyl acetate, 3% methanol/ethyl acetate, 4% methanol/ethyl acetate, 5% methanol/ethyl acetate to give the title compound.

27.2 Synthesis of (R)-1-(3,4,5-trimethoxybenzoyl)-3-(2-(4-phenyl-4-((4-carboethoxyethylpiperazin-1-yl) carboxamido)piperidine)ethyl)-3-(3,4-dichlorophenyl) pyrrolidine fumaric acid salt Combine (R)-1-(3,4,5-trimethoxybenzoyl)-3-(2-(4-phenyl-4-((4-carboethoxyethylpiperazin-1-yl)carboxamido) piperidine)ethyl)-3-(3,4-dichlorophenyl)pyrrolidine (0.7 g, 0.86 mmol) and ethanol (15 mL). Heat to reflux. Add fumaric acid (206 mg) and continue to heat at reflux. After 30 minutes, cool, concentrate in vacuo, and triturate with diethyl ether (50 mL). Filter and dry to give the title compound.

27.3 Synthesis of (R)-1-(3,4,5-trimethoxybenzoyl)-3-(2-(4-phenyl-4-((4-carboethoxyethylpiperazin-1-yl)carboxamido) piperidine)ethyl)-3-(3,4-dichlorophenyl)pyrrolidine hydrochloric acid salt Combine (R)-1-(3,4,5-trimethoxybenzoyl)-3-(2-(4-phenyl-4-((4-carboethoxyethylpiperazin-1-yl)carboxamido) piperidine)ethyl)-3-(3,4-dichlorophenyl)pyrrolidine (0.5 g) and ethyl acetate (6 mL). Add a solution of hydrochloric acid in diethyl ether (1.3 mL, 1M) to give a solid. After 30 minutes, filter and dry to give the title compound.

EXAMPLE 27

(R)-1-(3,4,5-Trimethoxybenzoyl)-3-(2-(4-phenyl-4-((4-carboethoxyethylpiperazin-1-yl)carboxamido) piperidin-1-yl)ethyl)-3-(3,4-dichlorophenyl) pyrrolidine

EXAMPLE 28

(R)-1-(3,4,5-Trimethoxybenzoyl)-3-(2-(4-phenyl-4-((4-carboxyethylpiperazin-1-yl)carboxamido) piperidin-1-yl)ethyl)-3-(3,4-dichlorophenyl) pyrrolidine

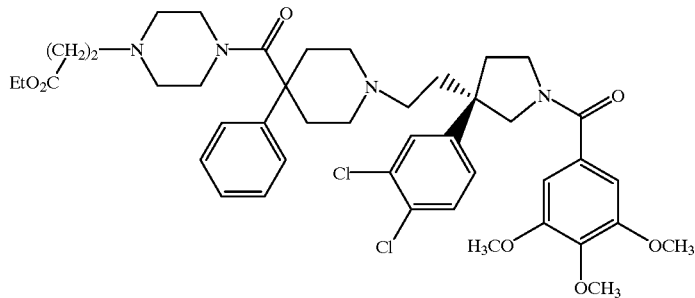

27.1 Synthesis of (R)-1-(3,4,5-trimethoxybenzoyl)-3-(2-(4-phenyl-4-((4-carboethoxyethylpiperazin-1-yl)carboxamido) piperidine)ethyl)-3-(3,4-dichlorophenyl)pyrrolidine

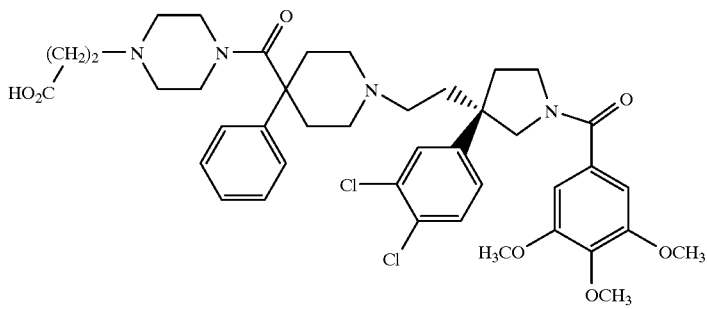

28.1 Synthesis of (R)-1-(3,4,5-trimethoxybenzoyl)-3-(2-(4-phenyl-4-((4-carboxyethylpiperazin-1-yl)carboxamido) piperidine)ethyl)-3-(3,4-dichlorophenyl)pyrrolidine Combine (R)-1-(3,4,5-trimethoxybenzoyl)-3-(2-(4-phenyl-4-((4-carboethoxyethylpiperazin-1-yl)carboxamido) piperidine)ethyl)-3-(3,4-dichlorophenyl)pyrrolidine (0.81g, 1.0 mmol) in tetrahydrofuran (20 mL) and water (20 mL). Cool in an ice bathe add lithium hydroxide (0.15 g). After 3 hours add water (100 mL) and a 1M aqueous hydrochloric acid solution (15 mL). Extract with ethyl acetate (100 mL). Separate the layers, adjust the pH of the aqueous layer to about 5 using 1M aqueous hydrochloric acid solution, and extract three times with dichloromethane. Combine the organic layers, dry over $MgSO_4$ and evaporate in vacuo to give the title compound.

28.2 Synthesis of (R)-1-(3,4,5-trimethoxybenzoyl)-3-(2-(4-phenyl-4-((4-carboxyethylpiperazin-1-yl)carboxamidodpiperidine)ethyl)-3-(3,4-dichlorophenyl) pyrrolidine hydrochloric acid salt Combine (R)-1-(3,4,5-trimethoxybenzoyl)-3-(2-(4-phenyl-4-((4-carboxyethylpiperazin-1-yl)carboxamido) piperidine)ethyl)-3-3,4-dichlorophenyl)pyrrolidine (0.57 g) and dichloromethane (20 mL). Add a solution of hydrochloric acid in diethyl ether (1.7 mL, 1M). After 2 hours, evaporate the reaction mixture in vacuo, twice add diethyl ether and evaporate in vacuo to give a residue. Triturate the residue with diethyl ether to give a solid. Collect the solid by filtration and dry to give the title compound.

PREPARATION 10

4-Phenyl-4-((4-carboethoxypropylpiperazin-1-yl) carboxamido)piperidine hydriodic acid salt Combine t-butyl 1-piperazinecarboxylate (10.7 g, 57.5 mmol), ethyl 4-chlorobutyrate (10.4 mL), and potassium carbonate (8 g) in dimethylformamide (60 mL). Heat at reflux. After 4.5, hours, cool the reaction, dilute with an aqueous solution of sodium bicarbonate, and extract twice with diethyl ether (200 mL). Combine the organic layers and extract with a 1M aqueous solution of hydrochloric acid. Adjust the pH of the aqueous layer to basic using sodium bicarbonate and then extract twice with diethyl ether. Dry the combined organic layers over $MgSO_4$, filter, and evaporate in vacuo to give a residue. Chromatograph the residue on silica gel eluting sequentially with 10% ethyl acetate/hexane, 20% ethyl acetate/hexane, 25% ethyl acetate/hexane to give t-butyl 4-carboethoxypropyl-1-piperazinecarboxylate. $R_f$=0.5 (silica gel, ethyl acetate).

Combine t-butyl 4-carboethoxypropyl-1-piperazinecarboxylate (7.0 g, 23.3 mmol) and dichloromethane (100 mL). Stir, cool to about 0° C. and purge with hydrochloric acid gas. After 2 hours, concentrate the reaction mixture in vacuo, twice add diethyl ether (50 mL) and evaporate in vacuo to give a solid. Triturate the solid with diethyl ether and collect by filtration to give 4-carboethoxypropyl-1-piperazine hydrochloric acid salt.

Combine 4-carboethoxypropyl-1-piperazine hydrochloric acid salt (5.6 g, 20.5 mmol), 1-t-butoxycarbonyl-4-phenyl-piperidine-4-carboxylic acid (8.13 g, 26.6 mmol), N,N-diisopropylethylamine (7.9 g), and 1-hydroxybenzotriazole hydrate (3.3 g, 24.6 mmol) in dichloromethane (250 mL). Add 1-(3-dimethylaminopropyl)-3-ethylcarbodiimide hydrochloride (4.72 g, 24.6 mmol). After 24 hours, dilute the reaction mixture with dichloromethane (100 mL) and extract with a saturated aqueous solution of sodium bicarbonate and then a 1M aqueous solution of hydrochloric acid. Dry the organic layer over $MgSO_4$, filter, and evaporate in vacuo to give residue. Chromatograph the residue on silica gel eluting sequentially with hexane, 20% ethyl acetate/hexane, 40% ethyl acetate/hexane, 60% ethyl acetate/heaxne, 80% ethyl acetate/hexane, ethyl acetate, and then 6%methanol/ethyl acetate to give 1-t-butoxycarbonyl-4-phenyl-4-((4-carboethoxypropyl piperazin-1-yl)carboxamido)piperidine.

Combine 1-t-butoxycarbonyl-4-phenyl-4-((4-carboethoxypropyl piperazin-1-yl)carboxamido)piperidine (6.7 g, 12.5 mmol) and ethanol (90 mL). Add an aqueous solution of hydriodic acid (6.2 g, 57%). Heat at reflux. After 15 hours, cool to ambient temperature and add diethyl ether (300 mL) to give a solid. Filter, rinse the solid with diethyl ether, and dry to give 4-phenyl-4-((4-carboethoxypropylpiperazin-1-yl)carboxamido)piperidine hydriodic acid salt.

EXAMPLE 29

(R)-1-(3,4,5-Trimethoxybenzoyl)-3-(2-(4-phenyl-4-((4-carboethoxypropylpiperazin-1-yl)carboxamido) piperidin-1-yl)ethyl)-3-(3,4-dichlorophenyl) pyrrolidine

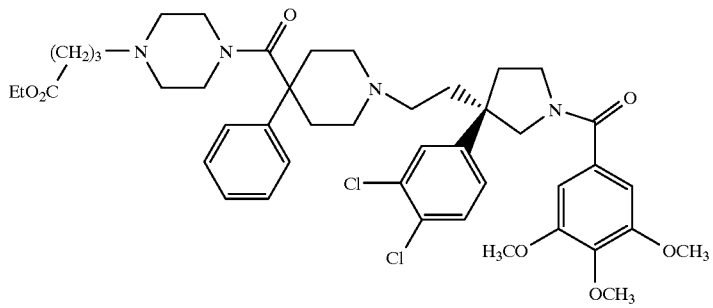

29.1 Synthesis of (R)-1-(3,4,5-trimethoxybenzoyl)-3-(2-(4-phenyl-4-((4-carboethoxypropylpiperazin-1-yl)carboxamido),iperidine)ethyl)-3-(3,4-dichiorophenyl)pyrrolidine Prepare by the method of 28.1 using (S)-1-(3,4,5-trimethoxybenzoyl)-3-(3,4-dichlorophenyl)-3-(2-methanesulfonyloxyethyl)pyrrolidine (4.0 g) and 4-phenyl-4-((4-carboethoxypropylpiperazin-1-yl)carboxamido)piperidine hydriodic acid salt. Purify by chromatography on silica gel eluting sequentially with ethyl acetate, 2% methanol/dichloromethane 3% methanol/dichloromethane, and then 4% methanol/dichloromethane to give the title compounds R$_f$=0.31 (silica gels 6% methanol/dichloromethane).

29.2 Synthesis of (R)-1-(3,4,5-trimethoxybenzoyl)-3-(2-(4-phenyl-4-((4-carboethoxyeproplpiperazin-1-yl)carboxamido)piperidine)ethyl)-3-(3,4-dichlorophenyl)pyrrolidine fumaric acid salt Combine (R)-1-(3,4,5-trimethoxybenzoyl)-3-(2-(4-phenyl-4-((4-carboethoxypropylpiperazin-1-yl)carboxamido)piperidine)ethyl)-3-(3,4-dichlorophenyl)pyrrolidine (0.7 g 0.86 mmol) and ethanol (15 mL). Heat to reflux. Add fumaric acid (202 mg) and continue to heat at reflux. After 30 minutes, cool, concentrate in vacuo, and triturate with diethyl ether (50 mL). Filter and dry to give the title compound.

29.3 Synthesis of (R)-1-(3,4,5-trimethoxybenzoyl)-3-(2-(4-phenyl-4-((4-carboethoxypropylpiperazin-1-yl)carboxamido)piperidine)ethyl)-3-(3,4-dichlorophenyl)pyrrolidine hydrochloric acid salt Combine (R)-1-(3,4,5-trimethoxybenzoyl)-3-(2-(4-phenyl-4-((4-carboethoxypropylpiperazin-1-yl)carboxamido)piperidine)ethyl)-3-(3,4-dichlorophenyl)pyrrolidine (0.5 g) and ethyl acetate (8 mL). Add a solution of hydrochloric acid in diethyl ether (1.4 mL, 1M) to give a solid. After 30 minutes, filter and dry to give the title compound.

EXAMPLE 30

(R)-1-(3,4,5-Trimethoxybenzoyl)-3-(2-(4-phenyl-4-((4-carboxypropylpiperazin-1-yl)carboxamido)piperidin-1-yl)ethyl)-3-(3,4-dichlorophenyl)pyrrolidine

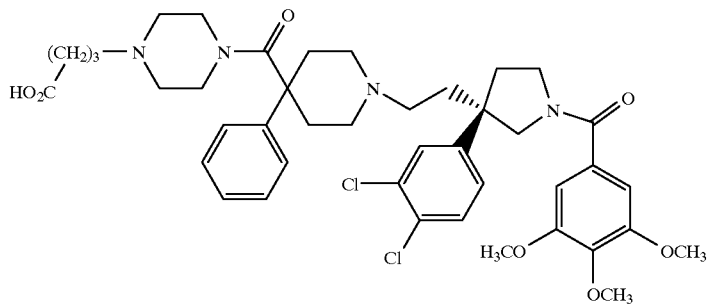

30.1 Synthesis of (R)-1-(3,4,5-trimethoxybenzoyl)-3-(2-(4-phenyl-4-((4-carboxypropylpiperazin-1-yl)carboxamido)piperidine ethyl)-3-(3,4-dichlorophenyl)pyrrolidine Prepare by the method of Example 28.1 using (R)-1-(3,4,5-trimethoxybenzoyl)-3-(2-(4-phenyl-4-((4-carboethoxypropylpiperazin-1-yl)carboxamido)piperidine)ethyl)-3-(3,4-dichlorophenyl)pyrrolidine to give the title compounds.

30.2 Synthesis of (R)-1-(3,4,5-trimethoxybenzoyl)-3-(2-(4-phenyl-4-((4-carboxypropylpiperazin-1-yl)carboxamido)piperidine)ethyl)-3-(3,4-dichlorophenyl)pyrrolidine hydrochloric acid salt Prepare by the method of Example 28.2 using (R)-1-(3,4,5-trimethoxybenzoyl)-3-(2-(4-phenyl-4-((4-carboxypropylpiperazin-1-yl)carboxamido)piperidine)ethyl)-3-(3,4-dichlorophenyl)pyrrolidine (0.63 g) to give the title compound.

PREPARATION 11

4-Phenyl-4-((4-carbo(ethoxycarbonyloxymethoxy)methylpiperazin-1-yl)carboxamido)piperidine hydrochloric acid salt Combine 4-carboethoxymethylpiperazine (100 g 580 mmol) and dichloromethane (750 mL). Cool in and ice-methanol bath. Add a solution of di-t-butyl dicarbonate (131 g, 600 mmol) in dichloromethane (250 mL). After 18 hours, evaporate in vacuo to obtain a residue. Divide the residue into three portions and chromatograph on silica gel eluting with 1/1 ethyl acetate/dichloromethane to give the product as the first eluting material. Evaporate the product containing fractions and recyrstallize from ethyl acetate/hexane to give 1-t-butoxycarbonyl-4-carboethoxymethylpiperazine as a solid, mp: 67–69° C. IR (KBr) nmax 2980, 1748, 1679, 1461, 1423, 1366, 1296, 1251, 1214, 1188, 1170, 1131, 1035 cm$^{-1}$; $^1$H NMR (CDCl$_3$) ppm 4.19 (q, 2 H, J=7.1 Hz), 3.49 (t, 4 H, J=4.7 Hz), 3.23 (s, 2 H), 2.53 (t, 4 H, J=4.9 Hz), 1.46 (s, 9 H), 1.28 (t, 3 H, J=7.1 Hz); $^{13}$C NMR (CDCl$_3$) ppm 170.06, 154.64, 79.68, 60.68, 59.39, 52.65, 28.39, 14.20; MS (CI/NH$_3$) m/z 273 (M+l)$^+$.

Combine 1-t-butoxycarbonyl-4-carboethoxymethylpiperazine (20.8 g, 76.5 mmol) and lithium hydroxide (6.71 g, 160 mmol) in tetrahydrofuran (100 mL) and water (100 mL). After 60 minutes, concentrate in vacuo to give a solid. Combine the solid and water, extract with diethyl ether. Combine the aqueous layer and a 1M aqueous solution of potassium hydrogensulfate (160 mL). Extract three times with chloroform. Evaporate the aqueous layer to give a solid. Triturate the solid repeatedly with warm ethyl acetate and isopropanol and filter. Evaporate each triturate to give solids. Combine the solids obtained by evaporation of the triturates, dissolve in chloroform and evaporate to remove solvent. Dry in vacuo at 50° C. to give 1-t-butoxycarbonyl-4-carboxymethylpiperazine as a solid, mp: 195–197° C. IR (KBr) nmax 3007, 2934, 1691, 1631, 1479, 1453, 1427, 1415, 1393, 1366, 1301, 1283, 1232, 1209, 1177, 1139, 1084 cm$^{-1}$; $^1$H NMR (CDCl$_3$) ppm 3.71 (br s, 4 H), 3.56 (br s, 2 H), 3.12 (br s, 4 H), 1.46 (s, 9 H); $^{13}$C NMR (CDCl$_3$) ppm 169.10, 154.13, 80.70, 58.49, 52.38, 28.25; MS (CI/NH$_3$) m/z 245 (M+1)$^+$.

Combine chloromethyl chloroformate (19 mL) and ichloromethane (300 mL) and cool in an ice bath. Add dropwise over about i hour, a solution of ethanol (11.7 mL and triethylamine (30.7 mL) in dichloromethane (100 mL). After 3.5 hours, filter and concentrate the filtrate to give a residue. Partition the residue between diethyl ether and water. Separate the organic layer and dry over MgSOA, filter and evaporate in vacuo to give ethyl chloromethyl carbonate.

Combine 1-t-butoxycarbonyl-4-carboxymethylpiperazine (10 g, 40.9 mmol), sodium iodide (6.15 g), cesium carbonate (13.3 g), ethyl chloromethyl carbonate (9.6 g) in dimethylformamide (250 mL). Heat to 65° C. After 3 hours, cool to ambient temperature and continue to stir. After 18 hours, concentrate in vacuo to give a residue. Chromatograph the residue on silica gel eluting sequentially with 5% ethyl acetate/hexane, 10% ethyl acetate/hexane, 15% ethyl acetate/hexane, and then 20% ethyl acetate/hexane to give 1-t-butoxycarbonyl-4-carbo(ethoxycarbonyloxymethoxy) methylpiperazine.

Combine 1-t-butoxycarbonyl-4-carbo(ethoxycarbonyloxymethoxy)methylpiperazine (9.5 g, dichloromethane (500 mL). Cool in an ice bath and purge with hydrochloric acid gas. After 1 hour, concentrate in vacuo to give a residue. Combine the residue and diethyl ether and evaporate to obtain a residue, dry in vacuo at 56° C. to give the title compound.

PREPARATION 12

(R)-1-(3,4,5-Trimethoxybenzoyl)-3-(2-(4-phenyl-4-carboxypiperidin-1-yl)ethyl)-3-(3,4-dichlorophenyl) pyrrolidine Combine (+)-1-(2-(3-(3,4-dichlorophenyl)-1-(3,4,5-trimethoxybenzoyl)-pyrrolidin-3-yl)-ethyl)-4-phenylpiperidine-4-carboxylic acid amide prepared by the method of U.S. Pat. No. 5,635,510, issued Jun. 3, 1997 (200 g, 300 mmol), dioxane (400 mL), concentrated aqueous hydrochloric acid (400 mL), and water (400 mL). Heat to reflux. After 26 hours, cool to ambient temperature and concentrate the reaction mixture in vacuo at about 60° C. to a volume of about 700 mL. Add water (400 mL) and extract with 9/1 ethyl acetate/hexaneo Separate the layers and extract the aqueous layer twice with 1/1 ethyl acetate/hexane. Adjust the pH of the aqueous layer to about 7 using sodium hydroxide to form a solid. Filter and dry to give (S)-3-(2-(4-phenyl-4-carboxypiperidin-1-yl)ethyl)-3-(3,4-dichlorophenyl)pyrrolidine.

Combine (S)-3-(2-(4-phenyl-4-carboxypiperidin-1-yl) ethyl)-3-(3,4-dichlorophenyl)pyrrolidine (50 g, 112 mmol) and sodium bicarbonate (30 g) in tetrahydrofuran (1300 mL) and water (300 mL). Add portionwise over about 45 minutes, a solution of 3,4,5-trimethoxybenzoyl chloride (26 g, 112 mmol) in tetrahydrofuran (130 mL). After 2 hours, dilute with water (1000 mL). Adjust the pH to about 4 using concentrated aqueous hydrochloric acid to give a solid. Collect the solid by filtration and rinse with water. Triturate the solid with methanol (1300 mL) and water (1300 mL). Filter, rinse with water and dry in vacuo to give the title compound.

Alternately prepare by a method similar to Example 5.4.1 using (S)-1-(3,4,5-trimethoxybenzoyl)-3-(3,4-dichlorophenyl)-3-(2-methanesulfonyloxyethyl)pyrrolidine and 4-phenylpiperidine-4-carboxylic acid to give the title compound.

EXAMPLE 31

(R)-1-(3,4,5-Trimethoxybenzoyl)-3-(2-(4-phenyl-4-((4-carbo(ethoxycarbonyloxymethoxy) methylpiperazin-1-yl)carboxamido)piperidin-1-yl) ethyl)-3-(3,4-dichlorophenyl)pyrrolidine

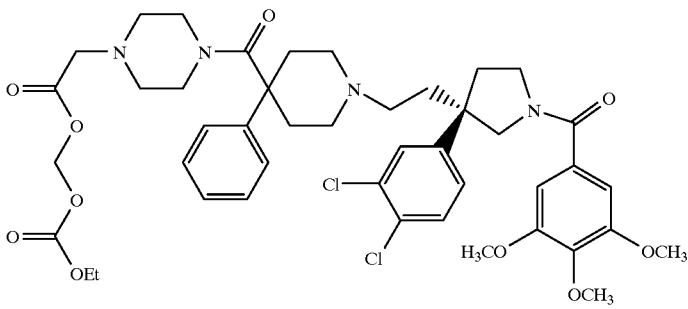

31.1 Synthesis of (R)-1-(3,4,5-trimethoxybenzoyl)-3-(2-(4-phenyl-4-((4-carbo(ethoxycarbonyloxymethoxy)methylpiperazin-1-yl)carboxamido)piperidine)ethyl)-3-(3,4-dichlorophenylpyrrolidine Combine (R)-1-(3,4,5-trimethoxybenzoyl)-3-(2-(4-phenyl-4-carboxypiperidin-1-yl)ethyl)-3-(3,4-dichlorophenyl)pyrrolidine (10 g, 15.52 mmol) and 4-phenyl-4-((4-carbo(ethoxycarbonyloxymethoxy)methylpiperazin-1-yl)carboxamido)piperidine hydrochloric acid salt (6 g, 18.8 mmol), and N,N-diisopropylethylamine (13 mL) in dichloromethane (400 mL). Add 1-hydroxybenzotriazole hydrate (2.1 g, 15.5 mmol) in dichloromethane and 1-(3-dimethylaminopropyl)-3-ethylcarbodiimide hydrochloride (3 g, 1505 mmol). After 18 hours, extract the reaction mixture with water. dry the organic layer over MgSO$_4$, filter, and concentrate in vacuo to give a residue. Chromatograph the residue on silica gel eluting sequentially with 0.3% methanol/dichloromethane, 0.6% methanol/dichloromethane, 100% methanol/dichloromethane, 1.5% methanol/dichloromethane, and then 2.5% methanol/dichloromethane to give a residue. Rechromatograph the residue on silica gel eluting sequentially with 1.0% methanol/dichloromethane, 2.0% methanol/dichloromethane, and then 3.0% methanol/dichloromethane to give the title compound.

31.2 Synthesis of (R)-1-(3,4,5-trimethoxybenzoyl)-3-(2-(4-phenyl-4-((4-carbo(ethoxycarbonyloxymethoxy)methylpiperazin-1-yl)carboxamido)piperidine)ethyl)-3-(3,4-dichlorophenyl)pyrrolidine fumaric acid salt Combine (R)-1-(3,4,5-trimethoxybenzoyl)-3-(2-(4-phenyl-4-((4-carbo(ethoxycarbonyloxymethoxy)methylpiperazin-1-yl)carboxamido)piperidine)ethyl)-3-(3,4-dichlorophenyl)pyrrolidine (0.51 g, 0.59 mmol) and fumaric acid (0.14 g, 1.17 mmol) in 2-butanone (40 mL). Heat to reflux. After 20 minutes, cool to ambient temperature. Concentrate in vacuo to give a residue. Triturate the residue with diethyl ether to give a solid. Collect the solid by filtration, rinse with diethyl ether, and dry to give the title compound.

PREPARATION 13

4-Phenyl-4-((4-carbo(t-butylcarbonyloxymethoxy)methylpiperazin-1-yl)carboxamido)piperidine hydrochloric acid salt Combine 1-t-butoxycarbonyl-4-carboxymethylpiperazine (1.22 g, 5 mmol) and cesium carbonate (1.63 g, 5 mmol) in anhydrous dimethylformamide (20 mL). After 1.5 hours, add chloromethyl pivalate (828 mg, 5.5 mmol) and sodium iodide (750 mg, 5 mmol). Heat to 60° C. After 3 hours, allow to cool to ambient temperature. After 18 hours, evaporate in vacuo to obtain a residue. Partition the residue between ethyl acetate and water. Separate the layers and extract the aqueous layer twice with ethyl acetate. Combine the organic layers and extract several times with water and then with brine. Dry over MgSO$_4$ and concentration in vacuo gave a residue. Chromatograph the residue on silica gel eluting with 75% ethyl acetate/hexane to give 1-t-butoxycarbonyl-4-carbo(t-butylcarbonyloxymethoxy)methylpiperazine: IR (KBr) nmax 2977, 1756, 1698, 1458, 1421, 1279, 1247, 1173, 1107, 1019, 1009, 986 cm$^{-1}$; $^1$H NMR (CDCl$_3$) ppm 5.79 (s, 2 H), 3.48 (t, 4 H, J=4.7 Hz), 3.23 (s, 2 H), 2.53 (t, 4 H, J=5.0 Hz), 1.46 (s, 9 H), 1.21 (s, 9 H); $^{13}$C NMR (CDCl$_3$) ppm 177.07, 168.84, 154.61, 79.75, 79.45, 77.20, 58.92, 52.49, 38.76, 28.41, 26.84; MS (CI/CH$_4$) m/z 359 (M+1)$^+$. Elemental Analysis Calculated for C$_{17}$H$_{30}$N$_2$O$_6$: C, 56.96; H, 8.44; N, 7.82. Found: C, 56.93; H, 8.43; N, 7.77.

Combine 1-t-butoxycarbonyl-4-carbo(t-butylcarbonyloxymethoxy)methylpiperazine (960 mg, 2.7 mmol) in anhydrous dioxane (20 mL). Cool in an ice bath. Add a solution of hydrochloric acid in dioxane (6 mL, 4M). After 3 hours, remove the cooling bath and allow to warm to ambient temperature. Evaporate in vacuo to give a solids mp 156–159° C.; IR (KBr) nmax 2981, 2937, 2923, 2719, 1763, 1459, 1417, 1396, 1209, 1156, 1123, 1006 cm$^{-1}$; $^1$H NMR (DMSO-d$_6$) ppm 9.53 (br s, 2 H), 5.77 (s, 2 H), 3.99 (br s, 2 H), 3.26 (br s, 4 H), 3.19 (br s, 4 H), 1.15 (s, 9 H); $^{13}$C NMR (DMSO-d$_6$) ppm 176.10, 166.31, 79.78, 55.14, 51.21, 48.26, 26.48; MS (CI/NH$_3$) m/z 259 (M+1)$^+$. Elemental Analysis Calculated for C$_{12}$H$_{22}$N$_2$O$_4$•2 HCl: C, 43.51; H, 7.30; N, 8.46. Found: C, 43.90; H, 7.55; N, 7.94.

EXAMPLE 32

(R)-1-(3,4,5-Trimethoxybenzoyl)-3-(2-(4-phenyl-4-((4-carbo(t-butylcarbonyloxymethoxy)methylpiperazin-1-yl)carboxamido)piperidin-1-yl)ethyl)-3-(3,4-dichlorophenyl)pyrrolidine

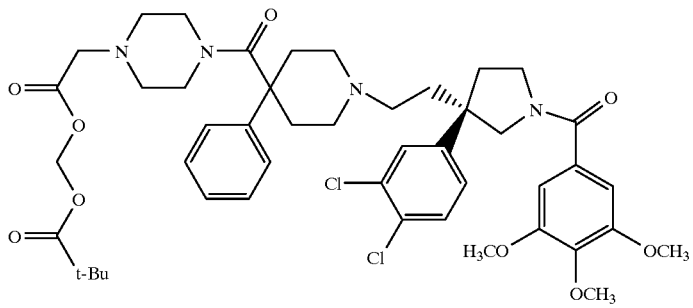

32.1 Synthesis of (R)-1-(3,4,5-trimethoxybenzoyl)-3-(2-(4-phenyl-4-((4-carbo(t-butylcarbonyloxymethoxy)methylpiperazin-1-yl)carboxamido)piperidine)ethyl)-3-(3,4-dichlorophenyl)pyrrolidine Combine (R)-1-(3,4,5-trimethoxybenzoyl)-3-(2-(4-phenyl-4-carboxypiperidin-1-yl)ethyl)-3-(3,4-dichlorophenyl)pyrrolidine (11.7 g, 18.24 mmol) and 4-phenyl-4-((4-carbo(t-butylcarbonyloxymethoxy)methylpiperazin-1-yl)carboxamido)piperidine hydrochloric acid salt (6 g, 18.1 mmol), and N,N-diisopropylethylamine (9.5), HATU (O-7-azabenzotriazol-1-yl)-N,N,N',N'-tetramethyluronium hexafluorophosphate)(7 g, 18.4 mmol), and anhydrous dimethylformamide 100 mL) in an oven-dried flaskb. After 48 hours, partition the reaction mixture between ethyl acetate (500 mL) and 0.1M aqueous hydrochloric acid solution. Separate the layers and extract the aqueous layer with ethyl acetate. Combine the organic layers and extract with water and then brine. Dry the organic layer over MgSO₄, filter, and evaporate in vacuo to give a residues Chromatograph the residue on silica gel eluting sequentially with (1%, methanol/dichloromethane, 2% methanol/dichloromethanea and then 3% methanol/dichloromethane to give the title compound% $R_f$=0.14 (silica gel, 6% methanol/ethyl acetate).

32.2 Synthesis of (R)-1-(3,4,5-trimethoxybenzoyl)-3-(2-(4-phenyl-4-((4-carbo(t-butylcarbonyloxymethoxy)methylpiperazin-1-yl)carboxamido)piperidine)ethyl)-3-(3,4-dichlorophenyl)pyrrolidine fumaric acid salt Heat to nearly refluxing a solution of (R)-1-(3,4,5-trimethoxybenzoyl)-3-(2-(4-phenyl-4-((4-carbo(t-butylcarbonyloxymethoxy) methylpiperazin-1-yl) carboxamido)piperidine)ethyl)-3-(3,4-dichlorophenyl)pyrrolidine (830 mg) in 2-butanone (5 mL). Combine with a solution of fumaric acid (221 mg, 1.90 mmol) in 2-butanone (30 mL) heated to nearly refluxing. After 30 minutes, cool to ambient temperature and evaporate in vacuo to give a residue. Triturate the residue with diethyl ether and stir. After about 1 hour, allow the solids to settles carefully decant the solvent and add more diethyl ether. Repeatedly, decant and add more diethyl ether. Filter and dry to give the title compound: mp 135–140° C.

PREPARATION 14

4-Phenyl-4-((4-carbo(N,N-diethylcarboxamidomethoxy) methylpiperazin-1-yl) carboxamido)piperidine hydrochloric acid salt Combine 1-t-butoxycarbonyl-4-carboxymethylpiperazine (1.0 g, 4.1 mmol) and cesium carbonate (133 g) in dimethylformamide (20 mL). After 2.5 hours, add 2-chloro-N,N-diethylacetamide (0.67 g) and sodium iodide (0.6 g). Heat to 65° C. After 3 hours, allow to cool to ambient temperature. After 18 hours, partition the residue between diethyl ether and a saturated aqueous solution of sodium bicarbonate. Extract the aqueous layer with diethyl ether. Combine the organic layers and extract several times with water and then with brine. Dry over MgSO₄, filter, and concentration in vacuo to give a residue. Chromatograph the residue on silica gel eluting sequentially with 1% methanol/dichloromethane, 2% methanol/dichloromethane, and then 3% methanol/dichloromethane to give 1-t-butoxycarbonyl-4-carbo(N,N-diethylcarboxamidomethoxy)methylpiperazine.

Combine 1-t-butoxycarbonyl-4-carbo(N,N-diethylcarboxamidomethoxy)methylpiperazine (0.3 g) and dichloromethane (10 mL). Cool in an ice bath. Purge with hydrochloric acid gas. After 2 hours, evaporate in vacuo, add dichloromethane and evaporate, dry in vacuo to give the title compound.

EXAMPLE 33

(R)-1-(3,4,5-Trimethoxybenzoyl)-3-(2-(4-phenyl-4-((4-carbo(N,N-diethylcarboxamidomethoxy) methylpiperazin-1-yl)carboxamido)piperidin-1-yl) ethyl)-3-(3,4-dichlorophenyl)pyrrolidine

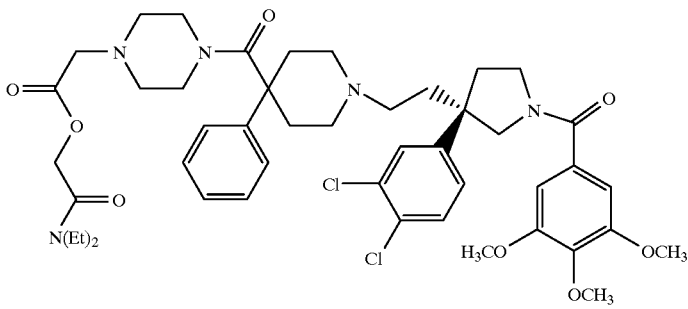

33.1 Synthesis of (R)-1-(3,4,5-trimethoxybenzoyl)-3-(2-(4-phenyl-4-((4-carbo(N,N-diethylcarboxamidomethoxy) methylpiperazin-1-yl)carboxamido)piperidine)ethyl)-3-(3,4-dichlorophenyl)pyrrolidine Combine (R)-1-(3,4,5-trimethoxybenzoyl)-3-(2-(4-phenyl-4-carboxypiperidin-1-yl)ethyl)-3-(3,4-dichlorophenyl)pyrrolidine (1.0 g, 1.5 mmol) and 4-phenyl-4-((4-carbo(N,N-diethylcarboxamidomethoxy) methylpiperazin-1-yl)carboxamido)piperidine hydrochloric acid salt (0.49 g, mmol), N,N-diisopropylethylamine (0.58 g), 1-hydroxybenzotriazole hydrate (0.28 g, 2.1 mmol), and 1-(3-dimethylaminopropyl)-3-ethylcarbodiimide hydrochloride (0.4 g, 2.1 mmol) in dimethylformamide (20 mL). After 18 hours, combine the reaction mixture with a saturate aqueous solution of sodium bicarbonate (200 mL) and extract three times with ethyl acetate. Combine the organic layers and evaporate in vacuo to give a residue. Chromatograph the residue on silica gel eluting sequentially with (1%, methanol/dichloromethane, 2% methanol/dichloromethane, 3%, methanol/dichloromethane, 4% methanol/dichloromethane, and then 5% methanol/dichloromethane to give the title compound.

33.2 Synthesis of (R)-1-(3,4,5-trimethoxybenzoyl)-3-(2-(4-phenyl-4-((4-carbo(N,N-diethylcarboxamidomethoxy) methylpiperazin-1-yl)carboxamido)piperidine)ethyl)-3-(3,4 dichlorophenyl)pyrrolidine fumaric acid salt Combine (R)-1-(3,4,5-trimethoxybenzoyl)-3-(2-(4-phenyl-4-((4-carbo(N,N-diethylcarboxamidomethoxy) methylpiperazin-1-yl)carboxamido)piperidine)ethyl)-3-(3,4-dichlorophenyl)pyrrolidine (0.47 g) and fumaric acid (0.125 g) in 2-butanone (10 mL). Heat to about 45° C. After 15 minutes, concentrate the reaction mixture in vacuo to give a residue. Triturate the residue with diethyl ether to give a solid. Collect the solid by filtration, rinse with diethyl ethers and dry in vacuo to give the title compound. Elemental Analysis Calculated for $C_{50}H_{60}Cl_2N_5O_{13}$: C, 57.34; H, 6.15; N, 6.19. Found: C 57.71; H, 6.36; N, 6.09.

PREPARATION 15

4-Phenyl-4-((4-carbo(methylcarbonyloxymethoxy) methylpiperazin-1-yl)carboxamido)piperidine hydrochloric acid salt Combine 1-t-butoxycarbonyl-4-carboxymethylpiperazine (2.44 g) and cesium carbonate (3.3 g) in dimethylformamide (60 mL). After 1 hour, add bromomethyl acetate (2 g) and sodium iodide (5 g). Heat to 65° C. After 3 hours, allow to cool to ambient temperatures After 18 hours, filter and dilute the filtrate with diethyl ether to form a precipitate. Filter to remove the precipitate and rinse with diethyl ether and evaporate the filtrate in vacuo to give a residue. Chromatograph the residue on silica gel eluting sequentially with 5% ethyl acetate/hexane, 10% ethyl acetate/hexane, 15% ethyl acetate/hexane, 20% ethyl acetate /hexane, and then 25% ethyl acetate/hexane to give 1-t-butoxycarbonyl-4-carbo (methylcarbonyloxymethoxy) methylpiperazine.

Combine 1-t-butoxycarbonyl-4-carbo (methylcarbonyloxymethoxy)methylpiperazine (2.5 g) and dichloromethane (50 mL). Cool in an ice bath. Purge with hydrochloric acid gas. After 2 hours, evaporate in vacuo, repeatedly add diethyl ether and evaporate. Add diethyl ether, filter, and dry in vacuo to give the title compound.

EXAMPLE 34

(R)-1-(3,4,5-Trimethoxybenzoyl)-3-(2-(4-phenyl-4-((4-carbo(methylcarbonyloxymethoxy) methylpiperazin-1-yl)carboxamido)piperidin-1-yl) ethyl)-3-(3,4-dichlorophenyl)pyrrolidine

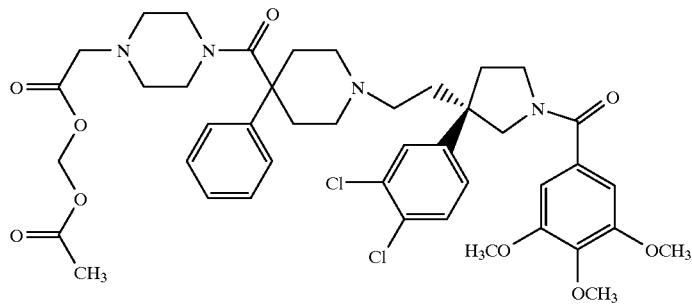

34.1 Synthesis of (R)-1-(3,4,5-trimethoxybenzoyl)-3-(2-(4-phenyl-4-(4-carbo(methylcarbonyloxymethoxy)

methylpiperazin-1-yl)carboxamido)piperidine)ethyl)-3-(3,4-dichlorophenyl)pyrrolidine Prepare by the method of Example 31.1 using (R)-1-3,4,5-trimethoxybenzoyl)-3-(2-(4-phenyl-4-carboxypiperidin-1-yl)ethyl)-3-(3,4-dichlorophenyl)pyrrolidine (3.5 g) and 4-phenyl-4-((4-carbo(methylcarbonyloxymethoxy) methylpiperazin-1-yl)carboxamido)piperidine hydrochloric acid salt (1.4 g)to give, after chromatograph on silica gel eluting sequentially with (1%, methanol/dichloromethane, 2% methanol/dichloromethane, and then 3%, methanol/dichloromethane, the title compound.

34.2 Synthesis of (R)-1-(3g4,5-trimethoxybenzoyl)-3-(2-(4-phenyl-4-((4-carbo(methylcarbonyloxymethoxy)methylpiperazin-1-yl)carboxamido)piperidine)ethyl)-3-(3,4-dichlorophenyl)pyrrolidine fumaric acid salt Prepare by the method of Example 33.2 using (R)-1-(3,4,5-trimethoxybenzoyl)-3-(2-(4-phenyl-4-((4-carbo(methylcarbonyloxymethoxy)methylpiperazin-1-yl)carboxamido)piperidine)ethyl)-3-(3,4-dichlorophenyl)pyrrolidine (0.97 g) and fumaric acid (0.27 g) to give the title compound.

PREPARATION 16

4-Phenyl-4-((4-carbo(propylcarbonyloxymethoxy) methylpiperazin-1-yldcarboxamido)piperidine hydrochloric acid salt Prepare by the method of Preparation 15 using chloromethyl butyrate to give, after chromatography on silica gel eluting with 75% ethyl acetate/hexane, 1-t-butoxycarbonyl-4-carbo(propylcarbonyloxymethoxy) methylpiperazine: IR (neat) nmax 2973, 1763, 1696, 1457, 1422, 1366, 1291, 1276, 1262, 1247, 1173, 1127, 1101, 1008, 988 cm$_{-1}$; $^1$H NMR (CDCl$_3$) ppm 5.79 (s, 2 H), 3.48 (t, 4 H, J=4.9 Hz), 3.29 (s, 2 H), 2.54 (t, 4 H, J=5.0 Hz), 2.35 (t, 2 H, J=7.3 Hz), 1.71–1.61 (m, 2 H), 1.49 (s, 9 H)g 0.96 (t, 3 H, J=7.3 Hz).

Combine 1-t-butoxycarbonyl-4-carbo (propylcarbonyloxymethoxy) methylpiperazine (1.15 g, 3.30 mmol) and anhydrous dioxane (20 mL). Cool in an ice bath. Add a solution of hydrochloric acid in dioxane (7 mL, 4M). After 18 hours concentrate in vacuo to give the title compound: mp 137–140° C.

EXAMPLE 35

(R)-1-(3,4,5-Trimethoxybenzoyl)-3-(2-(4-phenyl-4-((4-carbo(propylcarbonyloxymethoxy)methylpiperazin-1-yl)carboxamido)piperidin-1-yl) ethyl)-3-(3,4-dichlorophenyl)pyrrolidine 35.1 Synthesis of (R)-1-(3,4,5-trimethoxybenzoyl)-3-(2-(4-phenyl-4-((4-carbo(propylcarbonyloxymethoxy) methylpiperazin-1-yl)carboxamido)piperidine)ethyl)-3-(3,4-dichlorophenyl)pyrrolidine Prepare by the method of Example 32.1 using (R)-1-(3,4,5-trimethoxybenzoyl)-3-(2-(4-phenyl-4-carboxypiperidin-1-yl)ethyl)-3-(3,4-dichlorophenyl) pyrrolidine (13 g) and 4-phenyl-4-((4-carbo(propylcarbonyloxymethoxy)methylpiperazin-1-yl) carboxamido)piperidine hydrochloric acid salt (635 mg) to give, after chromatograph on silica gel eluting sequentially with (11% methanol/dichloromethane, 2% methanol/dichloromethane, and then 3%, methanol/dichloromethane, the title compound.

35.2 Synthesis of (R)-1-(3,4,5-trimethoxybenzoyl)-3-(2-(4-phenyl-4-((4-carbo(propylcarbonyloxymethoxy) methylpiperazin- 1-yl)carboxamido)piperidine)ethyl)-3-(3,4-dichlorophenyl)pyrrolidine fumaric acid salt Prepare by the method of Example 32.2 using (R)-1-(3,4,5-trimethoxybenzoyl)-3-(2-(4-phenyl-4-((4-carbo(propylcarbonyloxymethoxy)methylpiperazin-1-yl) carboxamido)piperidine)ethyl)-3-(3,4-dichlorophenyl) pyrrolidine and fumaric acid to give the title compound: IR (neat) nmax 1761, 1632, 1583, 1459, 1418, 1237, 1128, 1102, 1005, 845 cm$^{-1}$; MS (CI/NH$_3$) m/z 906 (M+1)$^+$.

PREPARATION 17

(R)-1-(3,4,5-Trimethoxybenzoyl)-3-(2-(4-phenyl-4-((4-carbo(carboxymethoxy)methylpiperazin-1-yl) carboxamido)piperidin-1-yl)ethyl)-3-(3,4-dichlorophenyl)pyrrolidine Combine 2-(trimethylsilyl)ethanol (7.3 mL) and triethylamine (25 mL) in dichloromethane (80 mL). Cool in an ice bath. Add dropwise chloroacetyl chloride (6.9 g). After the addition is complete warm the reaction mixture to ambient temperature After 5 hours, add chloroacetyl chloride (2.8 g), After 2 hours, filter the reaction mixture and extract with a saturated aqueous solution of sodium bicarbonate and then water. Dry the organic layer over MgSO$_4$, filter, and evaporate in vacuo to give a residue. Distill the residue to give 2-(trimethylsilyl)ethyl chloroacetate: bp 150° C. at 28 mm of Hg.

Combine 1-t-butoxycarbonyl-4-carboxymethylpiperazine (1.25 g, 5.1 mmol) and cesium carbonate (166 g, 5.1 mmol) in anhydrous dimethylformamide (15 mL). Add a solution of 2-(trimethylsilyl)ethyl chloroacetate (1.1 g, 5.6 mmol) in dimethylformamide (5 mL) and sodium iodide (0.77 g). Heat to 70° C. After 1.5 hours, cool to ambient temperature. After 18 hours, dilute the reaction mixture with water and extract three times with diethyl ether. Combine the organic

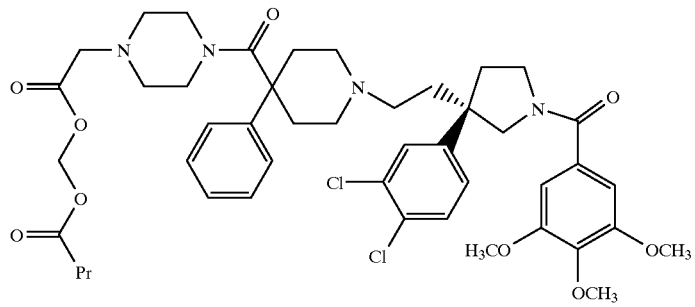

layers, dry over MgSO$_4$, and concentrate in vacuo gave a residue. Chromatograph the residue on silica gel eluting sequentially with 0.5% methanol/dichloromethane, 1% methanol/dichloromethane and then 2% methanol/dichloromethane to give 1-t-butoxycarbonyl-4-carbo-(carbo-(2-(trimethylsilyl)ethoxy)methoxy) methylpiperazine.

Combine 1-t-butoxycarbonyl-4-carbo-(carbo-(2-(trimethylsilyl)ethoxy)methoxy) methylpiperazine (2.1 g) and dichloromethane (20 mL). Cool in an ice bath. Purge with hydrochloric acid gas. After 2.5 hours, evaporate in vacuo to give a residue. Combine the residue and dichloromethane and evaporate in vacuo to give a residue. Triturate the residue with diethyl ether, filter and dry to give the 4-carbo-(carbo-(2-(trimethylsilyl)ethoxy)methoxy) methylpiperazine hydrochloric acid salt.

Combine 4-carbo-(carbo-(2-(trimethylsilyl)ethoxy) methoxy) methylpiperazine hydrochloric acid salt (0.92 g, 2.45 mmol), (2.7 g, 7.2 mmol), (R)-1-(3,4,5-trimethoxybenzoyl)-3-(2-(4-phenyl-4-carboxypiperidin-1-yl)ethyl)-3-(3,4-dichlorophenyl)pyrrolidine (5.1 g, 7.9 mmol), and N,N-diisopropylethylamine (5 mL) in dichloromethane (100 mL). After stirring for 10 minutes. add 1-hydroxybenzotriazole hydrate (1.1 g), and 1-ethyl-3-(3-dimethylaminopropyl)carbodiimide hydrochloride (153 g). After 18 hours, chromatograph the reaction mixture on silica gel eluting sequentially with 0.5% methanol/dichloromethane, 1% methanol/dichloromethane, and then 1.5% methanol/dichloromethane to give (R)-1-(3,4,5-trimethoxybenzoyl)-3-(2-(4-phenyl-4-((carbo-(carbo-(2-(trimethylsilyl)ethoxy)methoxy) methylpiperazin-1yl) carboxamido)piperidin-1-yl)ethyl)-3-(3,4-dichlorophenyl) pyrrolidine: R$_f$=0.38 (silica gel, 6% methanol/dichloromethane).

Combine (R)-1-(3,4,5-trimethoxybenzoyl)-3-(2-(4-phenyl-4-((carbo-(carbo-(2-(trimethylsilyl)ethoxy) methoxy) methylpiperazin-1yl)carboxamido)piperidin-1-yl) ethyl)-3-(3,4-dichlorophenyl)pyrrolidine (3.78 g, 4.15 mmol) and tetrahydrofuran (50 mL). Add a solution of tetrabutylammonium fluoride in tetrahydrofuran (6.6 mL, 1 M, 6.6 mmol). After 1 hour, add a solution of tetrabutylammonium fluoride in tetrahydrofuran (3.0 mL, 1 M), After 4.5 hours, evaporate the reaction mixture in vacuo to give a residue. Partition the residue between dichloromethane and water. Separate the layers, dry the organic layer over MgSO$_4$a filter, and evaporate in vacuo to the title compound.

EXAMPLE 36

(R)-1-(3,4,5-Trimethoxybenzoyl)-3-(2-(4-phenyl-4-((4-carbo(N,N-di-(2-hydroxyethyl) carboxamidomethoxy) methylpiperazin-1-yl) carboxamido)piperidin-1-yl)ethyl)-3-(3,4-dichlorophenyl)pyrrolidine

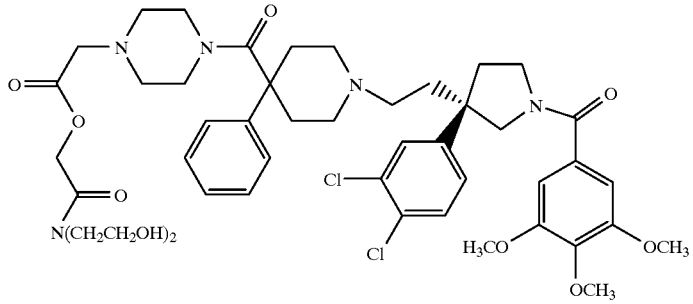

36.1 Synthesis of (R)-1-(3,4,5-trimethoxybenzoyl)-3-(2-(4-phenyl-4-((4-carbo(N,N-di-(2-hydroxyethyl) carboxamidomethoxy) methylpiperazin-1-yl)carboxamido) piperidin-1-yl)ethyl)-3-(3,4-dichlorophenyl)pyrrolidine Combine (R)-1-(3,4,5-trimethoxybenzoyl)-3-(2-(4-phenyl-4-((4-carbo(carboxymethoxy)methylpiperazin-1-yl) carboxamido)piperidin-1-yl)ethyl)-3-(3,4-dichlorophenyl) pyrrolidine (2.1 g, 2.54 mmol), diethanolamine (0.27 g, 2.54 mmol), 1-hydroxybenzotriazole hydrate (0.3 g, 2.8 mmol), 1-(3-dimethylaminopropyl)-3-ethylcarbodiimide hydrochloride (0.54 g, 2.8 mmol), and N,N-diisopropylethylamine (0.75 mL) in dichloromethane (30 mL). After 18 hours, chromatograph the reaction mixture on silica gel eluting sequentially with 2% methanol/dichloromethane, 3% methanol/dichloromethane, 4% methanol/dichloromethane, 5% methanol/dichloromethane, 6% methanol/dichloromethane, 6% methanol/dichloromethane containing 2 mL/L of concentrated ammonium hydroxide, 6% methanol/dichloromethane containing 4 mL/L of concentrated ammonium hydroxide, 6% methanol/dichloromethane containing 6 mL/L of concentrated ammonium hydroxide to give a residue. Rechromatograph the residue on silica gel eluting sequentially with 2% methanol/dichloromethane4% methanol/dichloromethane, 6% methanol/dichloromethane, and then 6% methanol/dichloromethane containing 6 mL/L of concentrated ammonium hydroxide to give a residue. Rechromatograph the residue on silica gel eluting with dichloromethane/methanol/concentrated ammonium hydroxide 95/5/0/5 to give the title compound.

36.2 Synthesis of (R)-1-(3,4,5-Trimethoxybenzoyl)-3-(2-(4-phenyl-4-((4-carbo(N,N-di-(2-hydroxyethyl) carboxamidomethoxy) methylpiperazin-1-yl)carboxamido) piperidin-1-yl)ethyl)-3-(3,4-dichlorophenyl)pyrrolidine fumaric acid salt Combine (R)-1-(3,4,5-Trimethoxybenzoyl)-3-(2-(4-phenyl-4-((4-carbo(di-(2-hydroxyethyl) carboxamidomethoxy) methylpiperazin-1-yl)carboxamido) piperidin-1-yl)ethyl)-3-(3,4-dichlorophenyl)pyrrolidine (0.75 g) and fumaric acid (0.190 g) in 2-butanone (40 mL). Heat to reflux. After 20 minutes, cool the reaction mixture and concentrate in vacuo to give a residue. Triturate the residue with diethyl ether, filter and dry to give the title compound.

EXAMPLE 37

(R)-1-(3,4,5-Trimethoxybenzoyl)-3-(2-(4-phenyl-4-((4-carbo(N-methyl-N-(2-dimethylaminoethyl))carboxamidomethoxy) methylpiperazin-1-yl)carboxamido)piperidin-1-yl)ethyl)-3-(3,4-dichlorophenyl)pyrrolidine

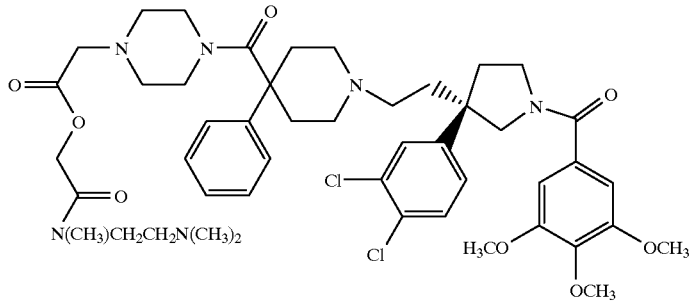

37.1 Synthesis of (R)-1-(3,4,5-trimethoxybenzoyl)-3-(2-(4-phenyl-4-((4-carbo(N-methyl-N-(2-dimethylaminoethyl))carboxamidomethoxy) methylpiperazin-1-yl)carboxamido)piperidin-1-yl)ethyl)-3-(3,4-dichlorophenyl)pyrrolidine Combine (R)-1-(3,4,5-trimethoxybenzoyl)-3-(2-(4-phenyl-4-((4-carbo(carboxymethoxy)methylpiperazin-1-yl)carboxamido)piperidin-1-yl)ethyl)-3-(3,4-dichlorophenyl)pyrrolidine (2.2 g, 2.7 mmol), N,N,N'-trimethylethylenediamine (0.3 g, 2.9 mmol), and N,N-diisopropylethylamine (0.8 mL) in dichloromethane (30 mL). After 10 minutes, add 1-hydroxybenzotriazole hydrate (0.39 g, 2.9 mmol) 1-(3-dimethylaminopropyl)-3-ethylcarbodiimide hydrochloride (0.56 g, 2.9 mmol). After 18 hours, chromatograph the reaction mixture on silica gel eluting sequentially with 2% methanol/dichloromethane, 3% methanol/dichloromethane, 4% methanol/dichloromethane, 5% methanol/dichloromethane, 6% methanol/dichloromethane 5 mL/L of concentrated ammonium hydroxide to give a residue. Combine the residue and dichloromethane (200 mL), extract with brine, dry the organic layer over $MgSO_4$, filter, and evaporate in vacuo to give the title compound: $R_f$=0.5 (silica gel, 90/10/0 dichloromethane/methanol/concentrated ammonium hydroxide).

37.2 Synthesis of (R)-1-(3,4,5-Trimethoxybenzoyl)-3-(2-(4-phenyl-4-((4-carbo(N-methyl-N-(2-dimethylaminoethyl))carboxamidomethoxy) methylpiperazin-1-yl)carboxamido)piperidin-1-yl)ethyl)-3-(3,4-dichlorophenyl)pyrrolidine fumaric acid salt Prepare by the method of Example 36.2 using (R)-1-(3,4,5-Trimethoxybenzoyl)-3-(2-(4-phenyl-4-((4-carbo(N-methyl-N-(2-dimethylaminoethyl))carboxamidomethoxy)methylpiperazin-1-yl)carboxamido)piperidin-1-yl)ethyl)-3-(3,4-dichlorophenyl)pyrrolidine to give the title compound.

PREPARATION 18

4-Carbo-(5-methyl-2-oxo-1,3-dioxol-4-ylmethoxy)methylpiperazine hydrochloric acid salt Combine 4,5-dimethyl-1,3-dioxol-2-one (3.42 g, 30 mmol), N-bromosuccinimide (5.34 g, 30 mmol) and AIBN (500 mg, 3 mmol) in anhydrous carbon tetrachloride (100 mL). Heat at reflux. After 2 hours, cool and filter. Concentrate the filtrate to give 4-bromomethyl-5-methyl-1,3-dioxol-2-one (6.5 g, crude) as an oil, which can be used for the next step without further purification.

Combine 1-t-butoxycarbonyl-4-carboxymethylpiperazine (980 mg, 4.01 mmol), crude 4-bromomethyl-5-methyl-1,3-dioxol-2-one (1.21 g, about 70% pure, 4.4 mmol), and cesium carbonate (1.30 g, 3.99 mmol) in dimethylformamide (16 mL). Heat to about 60° C. After 4 hours, cool the reaction mixture, dilute with water and extract three times with ethyl acetate. Combine the organic layers, extract with water and concentrate in vacuo to give a residue. Chromatograph the residue on silica gel eluting with ethyl acetate to give 1-t-butoxycarbonyl-4-carbo-(5-methyl-2-oxo-1,3-dioxol-4-ylmethoxy)methylpiperazine: IR (KBr) nmax 2976, 1825, 1750, 1693, 1423, 1247, 1231, 1169, 1130, 1012 $cm^{-1}$; $^1H$ NMR ($CDCl_3$) ppm 4.87 (s, 2 H), 3.47 (t, 4 H, J=5.0 Hz), 3.28 (s, 2 H), 2.53 (t, 4 H, J=5.0 Hz), 2.18 (s, 3 H), 1.71 (b, 1 H, $H_2O$), 1.45 (s, 9 H); MS (CI, $CH_4$) m/z 357 $(M+1)^+$. Elemental Analysis Calculated for $C_{16}H_{24}N_2O_7$: C, 53.93; H, 6.79; N, 7.86. Found: C, 54.11; H, 6.71; N, 7.52.

Combine 1-t-butoxycarbonyl-4-carbo-(5-methyl-2-oxo-1,3-dioxol-4-ylmethoxy)methylpiperazine (832 mg, 2.3 mmol) and anhydrous dioxane (20 mL). Cool in an ice bath. Add a solution of hydrochloric acid in dioxane (6 mL 4M HCl). After 1 hour, warm to ambient temperature. After 18 hours, evaporate in vacuo at about 50° C. to give the title compound: mp 79–82° C. Elemental Analysis Calculated for $C_{11}H_{16}N_2O_5 \cdot 2$ HCl: C, 40.14; H, 5.51; N, 8.51. Found: C, 39.89; H, 5.88; N, 7.35.

EXAMPLE 38

(R)-1-(3,4,5-Trimethoxybenzoyl)-3-(2-(4-phenyl-4-((4-carbo(5-methyl-2-oxo-1,3-dioxol-4-ylmethoxy)methylpiperazin-1-yl)carboxamido)piperidin-1-yl)ethyl)-3-(3,4-dichlorophenyl)pyrrolidine

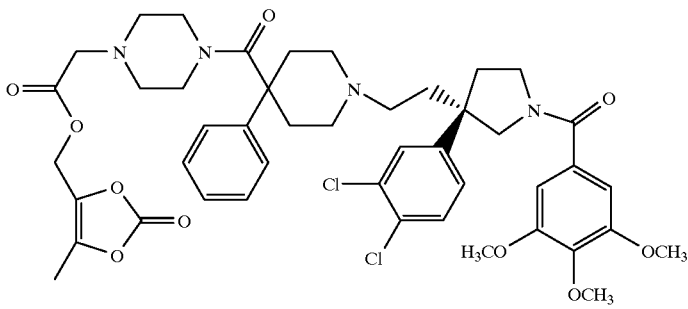

38.1 Synthesis of (R)-1-(3,4,5-Trimethoxybenzoyl)-3-(2-(4-phenyl-4-((4-carbo(5-methyl-2-oxo-1,3-dioxol-4-ylmethoxy)methylpiperazin-1-yl)carboxamido)piperidin-1-yl)ethyl)-3-(3,4-dichlorophenyl)pyrrolidine Combine (R)-1-(3,4,5-trimethoxybenzoyl)-3-(2-(4-phenyl-4-carboxypiperidin-1-yl)ethyl)-3-(3,4-dichlorophenyl)pyrrolidine (1.28 g, 2.00 mmol), HATU (O-7-azabenzotriazol-1-yl)-N,N,N',N'-tetramethyluronium hexafluorophosphate)(760 mg, 2 mmol), 4-carbo-(5-methyl-2-oxo-1,3-dioxol-4-ylmethoxy)methylpiperazine hydrochloric acid salt (658 mg, 2 mmol), and N,N-diisopropylethylamine (2.0 mL) in anhydrous dimethylformamide (10 mL). After 72 hours, evaporate in vacuo at 60° C. to remove most of the solvent. Partition the evaporated reaction mixture between ethyl acetate and a saturate aqueous sodium bicarbonate solution. Separate the layers and extract the aqueous layer with another portion of ethyl acetate. Combine the organic layers and extract with water and then brine. Concentrate in vacuo to give a residue. Chromatograph the residue on silica gel eluting sequentially with 3.75% methanol/dichloromethane, 5% methanol/dichloromethane, and then 7.5% methanol/dichloromethane to give the title compound.

38.2 Synthesis of (R)-1-(3,4,5-Trimethoxybenzoyl)-3-(2-(4-phenyl-4-((4-carbo(5-methyl-2-oxo-1,3-dioxol-4-ylmethoxy)methylpiperazin-1-yl)carboxamido)piperidin-1-yl)ethyl)-3-(3,4-dichlorophenyl)pyrrolidine fumaric acid salt Prepare by the method of Example 36.2 using (R)-1-(3,4,5-trimethoxybenzoyl)-3-(2-(4-phenyl-4-((4-carbo(5-methyl-2-oxo-1,3-dioxol-4-ylmethoxy)methylpiperazin-1-yl)carboxamido)piperidin-1-yl)ethyl)-3-(3,4-dichlorophenyl)pyrrolidine (955 mg, 1.085 mmol) and fumaric acid (252 mg, 2.17 mmol) to give the title compound: IR (KBr) nmax 3438, 2939, 1821, 1711, 1633, 1601, 1582, 1458, 1420, 1236, 1177, 1152, 1127 cm$^{-1}$; $^1$H NMR (DMSO-d$_6$) ppm 4.87 (s, 2 H), 3.47 (t, 4 H, J=5.0 Hz), 3.28 (s, 2 H), 2.53 (t, 4 H, J=5.0 Hz), 2.18 (s, 3 H), 1.71 (b, 1 H, H$_2$O), 1.45 (s, 9 H); MS (CI, CH$_4$) m/z 883, 881, 879 (H+1)$^+$. Elemental Analysis Calculated for Anal. $C_{45}H_{52}Cl_2N_4O_{10}$•1.75 $C_4H_4O_4$•0.6 $(C_2H_5)_2O$•$H_2O$: C, 57.04; H, 5.90; N, 4.89. Found: C, 57.09; H, 5.81; N, 4.52.

The tachykinins are a class of neuropeptides which share a common C-terminus sequenceb, Phe-Xaa-Gly-Leu-Met-NH$_2$. The tachykinins are widely distributed in the peripheral and central nervous systems where they bind to at least three receptors types. The NK$_1$, NK$_2$ and NK$_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions including cystitis; bronchoconstriction; hypersensitivity reactions; the treatment of pain; peripheral neuropathy; post-herpetic neuralgia; adverse immunological reactions; respiratory diseases, such as asthma, bronchitis, cough, rhinitis and allergies and the like; opthalmic diseases, such as conjuctivitis and vernal conjuctivitis; cutaneous diseases, such as contact dermatitis, atopic dermatitis, and urticaria; inflammatory diseases, such as rheumatoid arthritis and osteoarthritis and the like; gastrointestinal conditions, such as Crohn's disease, emesis, and ulcerative colitis; conditions due to vasodilation, such as angina and migraine; and central nervous system diseases and conditions, such as anxiety, depression, psychosis, schizophrenia, dementia.

It is understood that tachykinin-mediated diseases and conditions are those diseases and conditions in which the tachykinins are involved, either in whole or in part, in their clinical manifestations. Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1), and stereoisomers and pharmaceutically acceptable salts thereof. Particularly, the present invention provides compounds of formula (1) which are NK$_1$ and NK$_2$ receptor antagonists.

In a further embodiment, the present invention provides a method of treating tachykinin-mediated diseases and conditions in a patient in need thereof comprising administering to said patient a therapeutically effective amount of a compound of formula (1). Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (1).

As used herein, the term "patient" refers to a warm blooded animal such as a mammal which is afflicted with a particular tachykinin-mediated disease or condition. It is understood that guinea pigs, dogs, cats, rats, mice, horses, cattle, sheep, and humans are examples of animals within the scope of the meaning of the term. A patient is in need of treatment for tachykinin-mediated diseases and conditions when the patient is inflicted within one or more of the diseases or conditions described herein.

The identification of those patients who are in need of treatment of a tachykinin-mediated disease or condition is well within the ability and knowledge of one skilled in the art. A clinician skilled in the art can readily identify, by the use of clinical tests, physical examination and medical/family history, those patients who are in need of such treatment.

As used herein, the term "therapeutically effective amountb" of a compound of formula (1) refers to an amount which is effective in controlling tachykinin-mediated diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment of the tachykinin-mediated diseases and conditions.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with tachykinin-mediated diseases and conditions described above, a compound of formula (1) can be administered in any form or mode which makes the compound bioavailable in an effective amount, including oraly inhalation, parenteral, and topical routes. For example, compounds of formula (1) can be administered orally, by inhalation of an aerosol or dry powder, subcutaneously, intramuscularly, intravenously, intranasally, rectally, transdermally, topically, and the like. Oral or inhalation administration is generally preferred for treatment of respiratory diseases and conditions, eg. asthma, bronchitis, and cough. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practices The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds of formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1% and about 50% of the weight thereof. The amount of the active ingredient present in such compositions is such that a suitable dosage will be obtained. Preferred compositions and preparations are able to be determined by one skilled in the art.

The solutions or suspensions may also include one or more of the following adjuvants sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in amputees, disposable syringes or multiple dose vials made of glass or plastic The compounds of the present invention may also be administered by inhalation, such as by aerosol or dry powder. Delivery may be by a liquefied or compressed gas or by a suitable pump system which dispenses the compounds of the present invention or a formulation thereof. Formulations for administration by inhalation of compounds of formula (1) may be delivered in single phase, biphasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontinents, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The tachykinin receptor antagonists of the present invention can be evalutated by the procedures that follow.

EXAMPLE A

Antagonism of Iodinated Tachykinin Binding to $NK_1$ and $NK_2$ Receptors by Putative Antagonists One skilled in the art can determine the $NK_1$ receptor and $NK_2$ receptor affinity in vitro as follows. The $NK_1$ receptor affinity of tachykinin antagonists is evaluated in guinea pig lungs (Keystone Biologicals, Cleveland, Ohio) and affinity for the $NK_2$ receptor is evaluated in HSKR-1 cells (which are mouse 3T3 fibroblasts expressing the human jejunal $NK_2$ receptor). Tissues or cells are homogenized with a Polytron in 15 volumes of 50 mM Tris-HCl buffer (pH 7.4, 4° C.) and centrifuged. The pellet is resuspended in Tris-HCl buffer and is centrifuged; the pellet is washed twice by resuspension. The final pellet is resuspended at a concentration of 40 mg/ml for tissues and 20 mg/ml for cells in incubation buffer and remains at room temperature for at least 15 min prior to use. Receptor binding is initiated by addition of 250 ul membrane preparation in duplicate to 0.1 nM of the following radioligand: $^{125}$I-Bolton Hunter Lys-3 labeled substance P and $^{125}$iodohistidyl-1-neurokinin A; in a final volume of 500 ul of buffer containing 50 mM Tris-HCl (pH 7.4 at room temperature), 0.1% bovine serum albumin, 2 mM mangenese chlorides 40 ug/ml bacitracin, 4 $\mu$g/ml leupeptin and chymostatin, 10 $\mu$M thiorphan and various doses of the putative tachykinin antagonists. Incubations are performed at room temperature for 90 min ($NK_1$ receptor assays) or 2 hr ($NK_2$ receptor assay); binding is terminated by addition of 50 mM Tris-HCl buffer (pH 7.4, 4° C.) and filtration under vacuum through GF/B filters presoaked with 0.1% polyethyleneimine ($NK_1$ receptor assays) or 0.5% bovine serum albumin ($NK_2$ receptor assay). Filter bound radioactivity is quantitated in a gamma counter. Nonspecific binding is defined as binding in the presence of 1 $\mu$M substance P or neurokinin A. Specific binding is calculated by subtracting nonspecific binding from total binding. Competition of iodinated SP or NKA binding by test compounds or standards is expressed as a percentage of this maximum binding. $IC_{50}$ values (concentration required to inhibit 50% of receptor binding) are generated for each of the test compounds by nonlinear regression using an iterative curve fitting program (GraphPAD Inkplot, San Diego, Calif.).

EXAMPLE B

Antagonism of Tachykinin-Induced Phosphatidylinositol (PI) Turnover In Vitro by Putative Antagonists One skilled in the art can also determine the potency of $NK_1$ receptor and $NK_2$ receptor antagonism in vitro as follows. Tachykinin-mediated phosphatidylinositol (PI, inositol phosphate) accumulation is measured in UC11 or SKLKB82#3 cells in the presence and absence of $NK_1$ or $NK_2$ receptor antagonists, respectively. Tissues are incubated in Krebs-Henseleit buffer at 37° C. with 95% oxygen—5% carbon dioxide gassing. Tissues are then incubated with fresh buffer containing 100 $\mu$Ci of myo-[2-$^3$H (N)]inositol at 37° C. for 60 min with gentle gassing. After washing twice in 5 ml room temperature buffer containing 10 mM lithium chloride, tissues are incubated for 30 min at room temperature with a buffer change at 15 min. Buffer is removed and Krebs-Henseleit buffer (containing 40 $\mu$g/ml bacitracin, 4 $\mu$g/ml each of leupeptin and chymostatin, 0.1% bovine serum albumin and 10 $\mu$M of thiorphan and 10 mM of lithium chloride) including the test compound is added. After 15 min, SP is added to UC11 cells or NKA to SKLKB82#3 cells at various concentrations to start the reaction. After incubation for 60 min at room temperature the reaction is terminated by addition of 930 $\mu$l chloroform: methanol (1:2 by volume) to each tube, followed by 310 $\mu$l chloroform and 310 $\mu$l doubly distilled water. Samples are vortexes, centrifuged, and 0.9 ml of the aqueous (top) phase removed and added to 2 ml doubly distilled water. The mixture is vortexes and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled waters 2) 5 ml of 5 mM disodium tetraborate/60 mM sodium formate and 3) 5 ml of 1M ammonium formate/0.1M formic acid. The third elution is collected and 1 ml counted in 7 ml scintillation fluid. A 50 $\mu$l aliquot of the organic (bottom) phase is removed, dried in a scintillation vial and counted in 7 ml scintillation fluid.

The ratio of DPM in the aqueous phase aliquot (total inositol phosphates) to the DPM in the 50 $\mu$l organic phase aliquot (total [$^3$H]inositol incorporated) is calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist).

Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by the tachykinin. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. When the slope of the lines obtained by a Schild analysis are not significantly different from one (1) the compound is acting as a competitive antagonist.

EXAMPLE C

Evaluation of $NK_1$ Antagonism In Vivo

One skilled in the art can also determine that the compounds of the present invention are $NK_1$ receptor antagonists in vivo by evaluating the compoundes ability to inhibit substance P-induced plasma protein extravasation in guinea pig trachea. Substance P-induced protein leakage through post capillary venules is assessed by measuring Evans Blue dye accumulation in guinea pig trachea. Animals are anesthetized with pentobarbital then injected with Evans Blue dye (20 mg/kg, i.v., prepared in 0.9% sodium chloride solution). One minute after dye administration, the antagonist is administered (i.v.) followed by substance P (1.0 nmole/kg, i.v.) and, after 5 min, excess dye removed from the circulation by transcardiac perfusion with 50 ml 0.9% sodium chloride solution. The trachea and primary bronchi are removed, blotted dry and weighed.

Dye quantitation is performed spectrophotometrically (620 nm) after extracting tissues in formamide for 24 hr at 50° C. Values are subtracted from background (dye only, no agonist). $ED_{50}$ (dose of compound which inhibits substance P-induced plasma protein extravasation by 50%) is calculated from linear regression analysis.

EXAMPLE D

Evaluation of $NK_2$ Antagonism In Vivo

One skilled in the art can determine that the compounds of the present invention are $NK_2$ receptor antagonists in vivo by evaluating the compoundes ability to inhibit bronchoconstriction produced by a selective $NK_2$ receptor agonist, [$\beta$-Ala$^8$]NKA 4-10 in guinea pigs. Animals are anesthetized with urethane and then cannulated via the jugular vein, carotid artery, and trachea. The carotid cannula is connected to t Statham pressure transducer to measure blood pressure and the catheter placed into the jugular vein is used to administer the test compounds. The trachea cannula is inserted into a T-connector. one arm of the T-connector is connected to a respiratory pump while the other arm is connected to another pressure transducer. The respiratory pump is adjusted to deliver 64 strokes per minute and the volume of air delivered is such that the insufflation pressure is 10 cm of water. Animals are permitted to acclimate for about 15 minutes until stable breathing and blood pressure is obtained. Putative tachykinin antagonists or vehicle are administered i.v. and the line flushed with water. Dose response curves are then generated for the $NK_2$ receptor selective antagonists [$\beta$-Ala$^8$]NKA 4-10, at doses ranging form 1–30 nmole/kg, i.v. Bronchoconstriction is inferred from the dose-dependent increase in pulmonary insufflation pressure which occurs in response to the agonists. Antagonism of test compounds is inferred from a shift in the agonist dose-response curve to the right and suppression of the maximum insufflation pressure produced in response to [$\beta$-Ala$^8$]NKA 4-10.

EXAMPLE E

Evaluation of $NK_1$ and $NK_2$ Antagonism In Vivo

One skilled in the art can determine that the compounds of the present invention are $NK_2$ receptor antagonists in vivo by evaluating the compounds ability to inhibit capsaicin-induced respiratory effects, which is known to release both SP and NKA from airway sensory nerves. Antagonism of capsaicin induced respiratory effects in conscious guinea pigs is carried out as follows. In vivo experiments are performed using male Dunkin Hartley guinea pigs (250–350 g). Changes in conscious breathing patterns are monitored in four animals simultaneously using modified whole body plethysmography consisting of four small plexiglass boxes each connected to a reference box via Validyne DP 45-16 differential pressure transducers. The 4 boxes are equipped with an air supply line (also used for aerosol delivery) and an exhaust air line. Supply and exhaust lines are of the same length and narrow bore and arise from a common supply chamber and are vented to a common exhaust chamber. This system is used to ensure that fluctuations in supply air and atmospheric pressure remain in phase and are eliminated from the net signal by the differential pressure transducers. The analog pressure signals are digitalized via a Data Translation DT2821 A to D board. Data are collected at a rate of 100 samples/second/animal. Each cycle of pressure change is analyzed using the following parameters rising and falling slope determined between minimum and maximum pressures, the ratio of rising over falling slope, and the magnitude of the change between initial trough pressure and peak cycle pressure. Using these values (and observing the animals) the pressure cycles are characterized into normal breaths, forced exhalations (apparent by abdominal heaving), significant respiratory events (SREs; usually coughs, less often sneezes or gasps which are characterized by transient, extremely large pressure increases which are distinguishable from noise) and movement/noise with a PCAT 286 running a System V UNIX operating system. Dyspnea is defined as a significant, sustained increase in plethysmograph pressure which is associated with an observable shift to labored breathing in the animal.

During the course of a typical experiment in which airway responsiveness to various bronchoconstricting agents is examined, aerosols are delivered for 19 min (0.33 ml/min) using a DeVilbiss Ultraneb 99 ultrasonic nebulizer and animals monitored during this timeb. Prior to nebulization, 1 min of resting breathing is collected to establish a baseline pressure. In preliminary experiments, various concentrations of capsaicin were evaluated and the concentration of 0.001% chosen which maximized the number of animals exhibiting dyspnea but minimized the severity of the response. Putative tachykinin antagonists are administered (i.v.) 20 minutes prior to onset of aerosol exposure or orally 1 hour prior to onset of aerosol exposure.

Tackykinin receptor binding ($IC_{50}$ values) for representative compounds of the present invention are found in Table 1. The values in Table 1 were determined by the method of present Example A and represent the mean of several experiments, except where noted. Several of the compounds presented exhibit high affinity for both $NK_1$ and $NK_2$ receptors.

TABLE 1

| Example Number | Tachykinin Receptor Binding | |
|---|---|---|
| | $NK_1$ $IC_{50}$ (nM) | $NK_2$ $IC_{50}$ (nM) |
| 5.5 | 6.38 | 2.50 |
| 6.1 | 16.1 | 14.7 |
| 8.3.1 | 7.70 | 2.41 |
| 9.2 | 5.63 | 3.13 |
| 10.4 | 8.42 | 51.8 |
| 11.1 | 10.5 | 70.7 |
| 13.3 | 5.63 | 3.13 |
| 14.1 | 4.32 | 4.51 |
| 15.2 | 14.0 | 17.4 |
| 21.1 | 10.4 | 2.28 |
| 22.1 | 4.05 | 6.29 |
| 23.8 | 8.41 | 11.88 |
| 25.2 | 14.4 | 6.5 |
| 26.1 | 9.9 | 5.7 |
| 27.3 | 9.1 | 2.34 |

TABLE 1-continued

| Example Number | Tachykinin Receptor Binding | |
|---|---|---|
| | NK$_1$ IC$_{50}$ (nM) | NK$_2$ IC$_{50}$ (nM) |
| 28.2 | 19.6 | 3.73 |
| 29.2 | 11.9 | 3.21 |
| 30.2 | 3.4 | 3.6 |
| 31.2 | 11.7 | 9.1 |
| 32.2 | 21.25 | 13.93 |
| 33.2 | 3.95 | 2.43 |
| 35.2 | 14.7 | 11.7 |
| 36.1 | 2.68 | 2.32 |
| 37.2 | 2.09 | 0.90 |
| 38.2 | 7.82 | 4.3 |

What is claimed is:

1. A compound of the formula

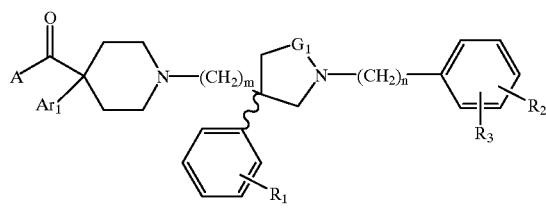

wherein

G$_1$ is CH$_2$ or C(O);
G$_2$ is CH$_2$ or C(O);
m is 2 or 3;
n is 0 or 1;
R$_1$ is from 1 to 3 substituents each independently chosen from the group consisting of hydrogen, halogen, —CF$_3$, C$_1$–C$_6$ alkyl, and C$_1$–C$_6$ alkoxy;
R$_2$ is from 1 to 3 substituents each independently chosen from the group consisting of hydrogen, halogen, cyano, —CF$_3$, C$_1$–C$_6$ alkyl, and C$_1$–C$_6$ alkoxy;
R$_3$ is hydrogen or the radical selected from the group consisting of

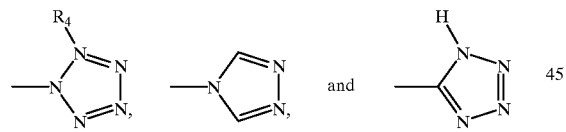

wherein
R$_4$ is selected from the group consisting of hydrogen, C$_1$–C$_4$ alkyl, and —CF$_3$;
Ar$_1$ is a radical selected from the group consisting of

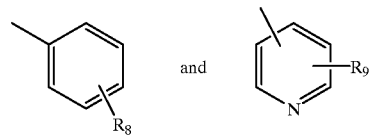

wherein
R$_8$ is from 1 to 3 substituents each independently chosen from the group consisting of hydrogen, halogen, —CF$_3$, C$_1$–C$_6$ alkyl, and C$_1$–C$_6$ alkoky;
R$_9$ is from 1 to 2 substituents each independently chosen from the group consisting of hydrogen, halogen, C$_1$–C$_6$ alkyl, and C$_1$–C$_6$ alkoxy;

A is a radical selected from the group consisting of

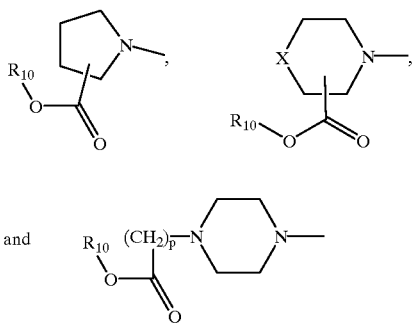

wherein
p is 1, 2, 3, or 4;
X is —O—, —S(O)$_k$— or —CH$_2$—,
wherein k is 0, 1, or 2;
R$_{10}$ is hydrogen, C$_1$–C$_6$ alkyl or a radical selected from the group consisting of

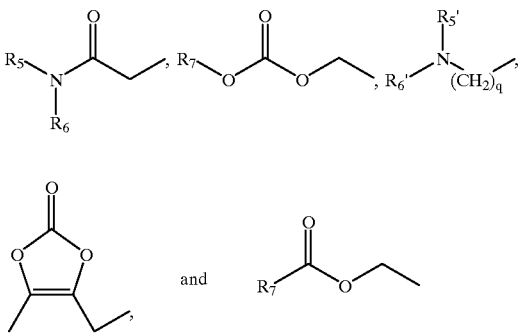

wherein
q is 2 or 3;
R$_5$ is C$_1$–C$_4$ alkyl or —(CH$_2$)$_2$OH;
R$_6$ is C$_1$–C$_4$ alkyl, —(CH$_2$)$_2$OH, or —(CH$_2$)$_2$N(CH$_3$)$_2$;
R$_5$' is C$_1$–C$_4$ alkyl;
R$_6$' is C$_1$–C$_4$ alkyl;
R$_7$' is C$_1$–C$_6$ alkyl;
provided that when G$_1$ is —C(O)— then G$_2$ is —CH$_2$—;
further provided that when G$_2$ is —C(O)— then G$_1$ is —CH$_2$—;
and stereoisomers, and pharmaceutically acceptable salts thereof.

2. A compound of claim 1 wherein n is 0.
3. A compound of claim 2 wherein m is 2.
4. A compound of claim 3 wherein G$_1$ is —CH$_2$— and G$_2$ is —C(O)—.
5. A compound of claim 4 wherein A is the radical

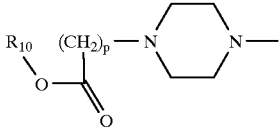

wherein p is 1 and R$_{10}$ is selected from the group consisting of hydrogen and C$_1$–C$_6$ alkyl.

6. A compound of claim 5 wherein R$_{10}$ is hydrogen.

7. A compound of claim 5 wherein $R_{10}$ is ethyl.

8. A compound of claim 1 wherein the compound is (R)-or (S)-1-(3,4,5-trimethoxybenzoyl)-3-(2-(4-phenyl-4-(((R)-or (S)-2-carboxypyrrolidin-1-yl)carboxamido)piperidin-1-yl) ethyl)-3-(3,4-dichlorophenyl)pyrrolidine or a mixture thereof.

9. A compound of claim 1 wherein the compound is (R)-or (S)-1-(3,4,5-trimethoxybenzoyl)-3-(2-(4-phenyl-4-(((R)-or (S)-2-carbomethoxypyrrolidin-1-yl)carboxamido)piperidin-1-yl)ethyl)-3-(3,4-dichlorophenyl)pyrrolidine or a mixture thereof.

10. A compound of claim 1 wherein the compound is (R)-or (S)-1-(3,4,5-trimethoxybenzoyl)-3-(2-(4-(pyrid-3-yl)-4-((4-carboethoxymethylpiperazin-1-yl)carboxamido) piperidin-1-yl)ethyl)-3-(3,4-dichlorophenyl)pyrrolidine or a mixture thereof.

11. A compound of claim 1 wherein the compound is (R)-or (S)-1-(3,4,5-trimethoxybenzoyl)-3-(2-(4-(pyrid-3-yl)-4-((4-carboxymethylpiperazin-1-yl)carboxamido) piperidin-1-yl)ethyl)-3-(3,4-dichlorophenyl)pyrrolidine or a mixture thereof.

12. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidin-1-yl)ethyl)-3-(3,4-dichlorophenyl)pyrrolidine or a mixture thereof.

13. A compound of claim 1 wherein the compound is (R)-or (S)-1-(3,4,5-trimethoxybenzoyl)-3-(2-(4-phenyl-4-((4-carboxymethylpiperazin-1-yl)carboxamido)piperidin-1-yl)ethyl)-3-(3,4-dichlorophenyl)pyrrolidine or a mixture thereof.

14. A compound of claim 1 wherein the compound is (R)-or (S)-1-(2-methoxy-5-(1H-tetrazol-1-yl)benzoyl)-3-(2-(4-phenyl-4-((4-carboethoxymethylpiperazin-1-yl) carboxamido)piperidin-1-yl)ethyl)-3-(3,4-dichlorophenyl) pyrrolidine or a mixture thereof.

15. A compound of claim 1 wherein the compound is (R)-or (S)-1-(2-methoxy-5-(1H-tetrazol-1-yl)benzoyl)-3-(2-(4-phenyl-4-((4-carboxymethylpiperazin-1-yl) carboxamido) piperidin-1-yl)ethyl)-3-(3,4-dichlorophenyl) pyrrolidine or a mixture thereof.

16. A compound of claim 1 wherein the compound is (R)-or (S)-1-(3,4,5-trimethoxybenzoyl)-3-(2-(4-phenyl-4-((4-carboethoxypiperidin-1-yl)carboxamido)piperidin-1-yl) ethyl)-3-(3,4-dichlorophenyl)pyrrolidine or a mixture thereof.

17. A compound of claim 1 wherein the compound is (R)-or (S)-1-(3,4,5-trimethoxybenzoyl)-3-(2-(4-phenyl-4-((4-carboxypiperidin-1-yl)carboxamido)piperidin-1-yl) ethyl)-3-(3,4-dichlorophenyl)pyrrolidine or a mixture thereof.

18. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine oxalic acid salt or a mixture thereof.

19. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine hydrochloric acid salt or a mixture thereof.

20. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine maleic acid salt or a mixture thereof.

21. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine fumaric acid salt or a mixture thereof.

22. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine citric acid salt or a mixture thereof.

23. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine methanesulfonic acid salt or a mixture thereof.

24. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine 2-hydroxyethanesulfonic acid salt- or a mixture thereof.

25. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine hydrobromic acid salt or a mixture thereof.

26. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine tartaric acid salt or a mixture thereof.

27. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine ethanesulfonic acid salt or a mixture thereof.

28. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidine)ethyl)-3-(3,4-dichlorophenyl)pyrrolidine (1R)-(–)-10-camphorsulfonic acid salt or a mixture thereof.

29. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidin-1-yl)ethyl)-3-(3,4-difluorophenyl)pyrrolidine or a mixture thereof.

30. A compound of claim 1 wherein the compound is (R)-or (S)-1-(3,4,5-trimethoxybenzoyl)-3-(2-(4-phenyl-4-((4-carboethoxymethylpiperazin-1-yl)carboxamido) piperidin- 1-yl)ethyl)-3-(3,4-difluorophenyl)pyrrolidine hydrochloric acid salt or a mixture thereof.

31. A compound of claim 1 wherein the compound is (R)-or (S)-1-(3,4,5-trimethoxybenzoyl)-3-(2-(4-phenyl-4-((4-carboxymethylpiperazin-1-yl)carboxamido)piperidin-1-yl)ethyl)-3-(3,4-difluorophenyl)pyrrolidine or a mixture thereof.

32. A compound of claim 1 wherein the compound is (R)-or (S)-(R)-1-(3,4,5-trimethoxybenzoyl)-3-(2-(4-phenyl-4-((2-carboethoxymorpholin-4-yl)carboxamido)piperidin-1-yl)ethyl)-3-(3,4-dichlorophenyl)pyrrolidine or a mixture thereof.

33. A compound of claim 1 wherein the compound is (R)-or (S)-1-(3,4,5-trimethoxybenzoyl)-3-(2-(4-phenyl-4-((2-carboethoxymorpholin-4-yl)carboxamido)piperidin-1-yl)ethyl)-3-(3,4-dichlorophenyl)pyrrolidine fumaric acid salt or a mixture thereof.

34. A compound of claim 1 wherein the compound is (R)-or (S)-1-(3,4,5-trimethoxybenzoyl)-3-(2-(4-phenyl-4-((2-carboxymorpholin-4-yl)carboxamido)piperidin-1-yl) ethyl)-3-(3,4-dichlorophenyl)pyrrolidine or a mixture thereof.

35. A compound of claim 1 wherein the compound is (R)-or (S)-1-(3,4,5-trimethoxybenzoyl)-3-(2-(4-phenyl-4-((4-carboethoxyethylpiperazin-1-yl)carboxamido)piperidin-1-yl)ethyl)-3-(3,4-dichlorophenyl)pyrrolidine or a mixture thereof.

36. A compound of claim 1 wherein the compound is (R)-or (S)-1-(3,4,5-trimethoxybenzoyl)-3-(2-(4-phenyl-4-

((4-carboethoxyethylpiperazin-1-yl)carboxamido)piperidin-1-yl)ethyl)-3-(3,4-dichlorophenyl)pyrrolidine fumaric acid salt or a mixture thereof.

37. A compound of claim 1 wherein the compound is (R)-or (S)-1-(3,4,5-trimethoxybenzoyl)-3-(2-(4-phenyl-4-((4-carboethoxyethylpiperazin-1-yl)carboxamido)piperidin-1-yl)ethyl)-3-(3,4-dichlorophenyl)pyrrolidine hydrochloric acid salt or a mixture thereof.

38. A compound of claim 1 wherein the compound is (R)-or (S)-1-(3,4,5-trimethoxybenzoyl)-3-(2-(4-phenyl-4-((4-carboxyethylpiperazin-1-yl)carboxamido)piperidine)ethyl)-3-(3,4-dichlorophenyl)pyrrolidine or a mixture thereof.

39. A compound of claim 1 wherein the compound is (R)-or (S)-1-(3,4,5-trimethoxybenzoyl)-3-(2-(4-phenyl-4-((4-carboxyethylpiperazin-1-yl)carboxamido)piperidine)ethyl)-3-(3,4-dichlorophenyl)pyrrolidine hydrochloric acid salt or a mixture thereof.

40. A compound of claim 1 wherein the compound is (R)-or (S)-1-(3,4,5-Trimethoxybenzoyl)-3-(2-(4-phenyl-4-((4-carboethoxypropyl piperazin-1-yl)carboxamido)piperidin-1-yl)ethyl)-3-(3,4-dichlorophenyl)pyrrolidine or a mixture thereof.

41. A compound of claim 1 wherein the compound is (R)-or (S)-1-(3,4,5-trimethoxybenzoyl)-3-(2-(4-phenyl-4-((4-carboethoxyeproplpiperazin-1-yl)carboxamido)piperidine)ethyl)-3-(3,4-dichlorophenyl)pyrrolidine fumaric acid salt or a mixture thereof.

42. A compound of claim 1 wherein the compound is (R)-or (S)-1-(3,4,5-trimethoxybenzoyl)-3-(2-(4-phenyl-4-((4-carboethoxypropyl piperazin-1-yl)carboxamido)piperidine)ethyl)-3-(3,4-dichlorophenyl)pyrrolidine hydrochloric acid salt or a mixture thereof.

43. A compound of claim 1 wherein the compound is (R)-or (S)-1-(3,4,5-trimethoxybenzoyl)-3-(2-(4-phenyl-4-((4-carboxypropylpiperazin-1-yl)carboxamido)piperidine)ethyl)-3-(3,4-dichlorophenyl)pyrrolidine or a mixture thereof.

44. A compound of claim 1 wherein the compound is (R)-or (S)-1-(3,4,5-trimethoxybenzoyl)-3-(2-(4-phenyl-4-((4-carboxypropylpiperazin-1-yl)carboxamido)piperidine)ethyl)-3-(3,4-dichlorophenyl)pyrrolidine hydrochloric acid salt or a mixture thereof.

45. A compound of claim 1 wherein the compound is (R)-or (S)-1-(3,4,5-Trimethoxybenzoyl)-3-(2-(4-phenyl-4-((4-carbo(ethoxycarbonyloxymethoxy)methylpiperazin-1-yl)carboxamido)piperidin-1-yl)ethyl)-3-(3,4-dichlorophenyl)pyrrolidine or a mixture thereof.

46. A compound of claim 1 wherein the compound is (R)-or (S)-1-(3,4,5-Trimethoxybenzoyl)-3-(2-(4-phenyl-4-((4-carbo(ethoxycarbonyloxymethoxy)methylpiperazin-1-yl)carboxamido)piperidin-1-yl)ethyl)-3-(3,4-dichlorophenyl)pyrrolidine fumaric acid salt or a mixture thereof.

47. A compound of claim 1 wherein the compound is (R)-or (S)-1-(3,4,5-trimethoxybenzoyl)-3-(2-(4-phenyl-4-((4-carbo(t-butylcarbonyloxymethoxy) methylpiperazin-1-yl)carboxamido)piperidine)ethyl)-3-(3,4-dichlorophenyl)pyrrolidine or a mixture thereof.

48. A compound of claim 1 wherein the compound is (R)-or (S)-1-(3,4,5-trimethoxybenzoyl)-3-(2-(4-phenyl-4-((4-carbo(t-butylcarbonyloxymethoxy) methylpiperazin-1-yl)carboxamido)piperidine)ethyl)-3-(3,4-dichlorophenyl)pyrrolidine fumaric acid salt or a mixture thereof.

49. A compound of claim 1 wherein the compound is (R)-or (S)-1-(3,4,5-trimethoxybenzoyl)-3-(2-(4-phenyl-4-((4-carbo(N,N-diethylcarboxamidomethoxy)methylpiperazin-1-yl)carboxamido)piperidine)ethyl)-3-(3,4-dichlorophenyl)pyrrolidine or a mixture thereof.

50. A compound of claim 1 wherein the compound is (R)-or (S)-1-(3,4,5-trimethoxybenzoyl)-3-(2-(4-phenyl-4-((4-carbo(N,N-diethylcarboxamidomethoxy)methylpiperazin-1-yl)carboxamido)piperidine)ethyl)-3-(3,4-dichlorophenyl)pyrrolidine fumaric acid salt or a mixture thereof.

51. A compound of claim 1 wherein the compound is (R)-or (S)-1-(3,4,5-trimethoxybenzoyl)-3-(2-(4-phenyl-4-((4-carbo(methylcarbonyloxymethoxy)methylpiperazin-1-yl)carboxamido)piperidine)ethyl)-3-(3,4-dichlorophenyl)pyrrolidine or a mixture thereof.

52. A compound of claim 1 wherein the compound is (R)-or (S)-1-(3,4,5-trimethoxybenzoyl)-3-(2-(4-phenyl-4-((4-carbo(methylcarbonyloxymethoxy)methylpiperazin-1-yl)carboxamido)piperidine)ethyl)-3-(3,4-dichlorophenyl)pyrrolidine fumaric acid salt or a mixture thereof.

53. A compound of claim 1 wherein the compound is (R)-or (S)-1-(3,4,5-trimethoxybenzoyl)-3-(2-(4-phenyl-4-((4-carbo(propylcarbonyloxymethoxy)methylpiperazin-1-yl)carboxamido)piperidine)ethyl)-3-(3,4-dichlorophenyl)pyrrolidine or a mixture thereof.

54. A compound of claim 1 wherein the compound is (R)-or (S)-1-(3,4,5-trimethoxybenzoyl)-3-(2-(4-phenyl-4-((4-carbo(propylcarbonyloxymethoxy)methylpiperazin-1-yl)carboxamido)piperidine)ethyl)-3-( 3,4-dichlorophenyl)pyrrolidine fumaric acid salt or a mixture hereof.

55. A compound of claim 1 wherein the compound is (R)-or (S)-1-(3,4,5-trimethoxybenzoyl)-3-(2-(4-phenyl-4-((4-carbo(N,N-di-(2-hydroxyethyl)carboxamidomethoxy)methylpiperazin-1-yl)carboxamido)piperidin-1-yl)ethyl)-3-3,4-dichlorophenyl)pyrrolidine or a mixture thereof.

56. A compound of claim 1 wherein the compound is (R)-or (S)-1-(3,4,5-trimethoxybenzoyl)-3-(2-(4-phenyl-4-((4-carbo(N,N-di-(2-hydroxyethyl)carboxamidomethoxy)methylpiperazin-1-yl)carboxamido)piperidin-1-yl)ethyl)-3-(3,4-dichlorophenyl)pyrrolidine fumaric acid salt or a mixture thereof.

57. A compound of claim 1 wherein the compound is (R)-or (S)-1-(3,4,5-trimethoxybenzoyl)-3-(2-(4-phenyl-4-((4-carbo(N-methyl-N-(2-dimethylaminoethyl))carboxamidomethoxy) methylpiperazin-1-yl)carboxamido)piperidin-1-yl)ethyl)-3-(3,4-dichlorophenyl)pyrrolidine or a mixture thereof.

58. A compound of claim 1 wherein the compound is (R)-or (S)-1-(3,4,5-trimethoxybenzoyl)-3-(2-(4-phenyl-4-((4-carbo(N-methyl-N-(2-dimethylaminoethyl))carboxamidomethoxy) methylpiperazin-1-yl)carboxamido)piperidin-1-yl)ethyl)-3-(3,4-dichlorophenyl)pyrrolidine fumaric acid salt or a mixture thereof.

59. A compound of claim 1 wherein the compound is (R)-or (S)-1-(3,4,5-trimethoxybenzoyl)-3-(2-(4-phenyl-4-((4-carbo(5-methyl-2-oxo-1,3-dioxol-4-ylmethoxy)methylpiperazin-1-yl)carboxamido)piperidin-1-yl)ethyl)-3-(3,4-dichlorophenyl)pyrrolidine or a mixture thereof.

60. A compound of claim 1 wherein the compound is (R)-or (S)-1-(3,4,5-trimethoxybenzoyl)-3-(2-(4-phenyl-4-((4-carbo(5-methyl-2-oxo-1,3-dioxol-4-ylmethoxy)methylpiperazin-1-yl)carboxamido)piperidin-1-yl)ethyl)-3-(3,4-dichlorophenyl)pyrrolidine fumaric acid salt or a mixture thereof.

61. A pharmaceutical composition comprising a compound of claim 1 and a pharmaceutically acceptable carrier.

62. A method for treating asthma in a patient in need thereof comprising administering to said patient a therapeutically effective amount of a compound of claim 1.

63. A method for treating cough in a patient in need thereof comprising administering to said patient a therapeutically effective amount of a compound of claim 1.

64. A method for treating bronchitis in a patient in need thereof comprising administering to said patient a therapeutically effective amount of a compound of claim 1.

* * * * *

UNITED STATES PATENT AND TRADEMARK OFFICE
CERTIFICATE OF CORRECTION

PATENT NO.    : 5,977,139
DATED         : November 2, 1999
INVENTOR(S)   : Timothy P. Burkholder, George D. Maynard and Elizabeth M. Kudlacz It is certified that error appears in the above-identified patent and that said Letters Patent is hereby corrected as shown below:

Column 1,
Line 44, reads as " 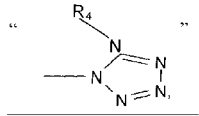 " and should read as -- 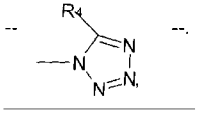 --.

Line 51, reads as "C4" and should read as -- $C_4$ --.

Column 2,
Line 63, reads as "3,13-" and should read as -- 3,3- --.

Column 3,
Line 13, reads as "are know" as should read as -- are known --.
Line 19, reads as "may exists" and should read as -- may exist --.
Line 56, reads as "micrgrams" and should read as -- micrograms --.

Column 4,
Line 1, reads as "μm" a refers" and should read as -- "μm" refers --.
Line 63, reads as "for examples" and should read as -- for example --.
Lines 65 and 66, read as "hydroxymaleicD benzoicD hydroxy-benzoicD" and should read as -- hydroxymaleic, benzoic, hydroxy-benzoic, --.

Column 7,
Line 16, reads as "caboxardido" and should read as -- carboxamido --.
Line 64, reads as "-1-y1y1)" and should read as -- -1-yl) --.

Column 8,
Line 67, reads as "(3g4-" and should read as -- (3,4- --.

Column 9,
Line 32, reads as "(4fluoro…" and should read as -- (4-fluoro --.
Line 37, reads as "(4-trifulor" and should read as -- (4-trifluor --.
Line 44, reads as "dimhoxphenyl" and should read as -- dimethoxyphenyl --.
Line 49, reads as "carboxamnido" should read as -- carboxamido --.

Column 13,
Line 51, reads as "arboxy" and should read as -- carboxy --.

UNITED STATES PATENT AND TRADEMARK OFFICE
CERTIFICATE OF CORRECTION

PATENT NO.    : 5,977,139
DATED         : November 2, 1999
INVENTOR(S)   : Timothy P. Burkholder, George D. Maynard and Elizabeth M. Kudlacz It is certified that error appears in the above-identified patent and that said Letters Patent is hereby corrected as shown below:

Column 14,
Line 13, reads as "arboxy" and should read as -- carboxy --.
Line 21, reads as "bentoyl" and should read as -- benzoyl --.
Line 34, reads as "pyrroelidine" and should read as -- pyrrolidine --.
Lines 63 and 66, reads as "arboxy" and should read as -- carboxy --.

Column 16,
Line 26, reads as "arboxy" and should read as -- carboxy --.
Line 47, reads as "arts" and should read as -- art. --.

Column 17,
Line 45, reads as "576357510" and should read as -- 5,635,510 --.
Line 50, reads as "bromom" and should read as -- bromo --.

Column 19,
Line 16, reads as "ipiperidine" and should read as -- piperidine --.

Column 23,
Line 21, reads as "RI" and should read as -- $R_1$ --.
Line 25, reads as "groupb" and should read as -- group --.
Line 27, reads as "chlorol bromob" and should read as -- chloro, bromo, --.
Line 33, reads as "tetrahyropyran" and should read as -- tetrahydropyran --.
Line 36, reads as "10" and should read as -- 1.0 --.
Line 39, reads as "hydrideb," and should read as -- hydride, --.
Line 40, reads as "amideb" and should read as -- amide --.

Column 25,
Line 4, reads as "bromob" and should read as -- bromo --.

Column 26,
Line 16, reads as "hydroxides" and should read as -- hydroxide. --.
Line 25, reads as "an an" and should read as -- an --.

Column 28,
Line 3, reads as "Bb." and should read as -- B. --.
Line 5, reads as "preferredb." and should read as -- preferred --.

Column 31,
Line 14, reads as "is one is one" and should read as -- A.1 and A.2 --.

UNITED STATES PATENT AND TRADEMARK OFFICE
CERTIFICATE OF CORRECTION

PATENT NO. : 5,977,139
DATED : November 2, 1999
INVENTOR(S) : Timothy P. Burkholder, George D. Maynard and Elizabeth M. Kudlacz It is certified that error appears in the above-identified patent and that said Letters Patent is hereby corrected as shown below:

Column 32,
Line 18, reads as "Ab.1 and Ab.2" and should read as -- A.1 and A.2 --.
Line 52, reads as "of of" and should read as -- of --.

Column 33,
Line 17, reads as "phaseb" and should read as -- phase --.
Line 28, reads as "extractions evaporations" and should read as -- extraction, evaporation, --.

Column 34,
Line 22, reads as "(trimethylsiilyl)" and should read as -- trimethylsilyl --.
Line 40, reads as "esters" and should read as -- ester, --.
Lines 46 and 60, reads as "ethylcarbodiimideb" and should read
as -- ethylcarbodiimide --.
Line 64, reads as "an about an" and should read as -- then about an --.

Column 35,
Line 8, reads as "an about an" and should read as -- then about an --.
Line 35, reads as "an appropriate a" and should read as -- an appropriate --.
Lines 55 and 58, reads as "amideb" and should read as -- amide --.

Column 37,
Line 32, reads as "chlorides" and should read as -- methanol --.
Line 45, reads as "bathe" and should read as -- bath, --.
Line 54, reads as "methanolo" and should read as -- methanol --.

Column 38,
Line 19, reads as "an salt-ice" and should read as -- an ice-salt --.
Line 41, reads as "212" and should read as -- 21.2 --.
Line 43, reads as "an salt-ice bathe" and should read as -- an ice-salt bath. --.
Line 56, reads as "filtered" and should read as -- filter, --.

Column 39,
Line 5, reads as "an salt-ice" and should read as -- an ice-salt --.
Line 9, reads as "iceb" and should read as -- ice --.
Line 37, reads as "(60 mgb," and should read as -- (60 mg, --.
Line 66, reads as "(30.0 gg" and should read as -- (30.0 g. --.

UNITED STATES PATENT AND TRADEMARK OFFICE
CERTIFICATE OF CORRECTION

PATENT NO. : 5,977,139
DATED : November 2, 1999
INVENTOR(S) : Timothy P. Burkholder, George D. Maynard and Elizabeth M. Kudlacz It is certified that error appears in the above-identified patent and that said Letters Patent is hereby corrected as shown below:

Column 40,
Line 39, reads as "bottleb" and should read as -- bottle --.
Line 57, reads as "a residues" and should read as a -- residue. --.

Column 41,
Lines 16 and 20, reads as "filters" and should read as -- filter --.
Line 27, reads as "a ice" and should read as -- an ice --.

Column 43,
Line 17, reads as "waters" and should read as --water, --.
Lines 53 and 56, reads as "hydrogenb" and should read as -- hydrogen. --.

Column 44,
Line 7, reads as "hydrogenb" and should read as -- hydrogen. --.
Line 21, reads as "compounds" and should read as -- compound. --.
Line 23, reads as "13" and should read as 1.3 --.
Line 45, reads as "NgSO$_4$" and should read as -- Mg SO$_4$,--.
Line 61, reads as "and and" and should read as -- and --.

Column 45,
Lines 1 and 6, reads as "Prepared" and should read as -- Prepare --.
Line 1, reads as "14.1" and should read as -- 1.4.1 --.
Line 6, reads as "14.2" and should read as -- 1.4.2 --.

Column 46,
Line 13, reads as "weights" and should read as -- weight, --.
Line 39, reads as "a residues" and should read as -- a residue, --.
Line 42, reads as "slurryb" and should read as -- slurry --.

Column 47,
Line 30, reads as "(106 g," and should read as -- (1.6 g --.
Line 32, reads as "an salt-ice" and should read as -- an ice-salt --.

Column 49,
Line 14, reads as "an salt-ice" and should read as -- an ice-salt --.
Line 28, reads as "(3-73 g" and should read as -- (3.73 g --.
Line 43, reads as "181 mmol" and should read as -- 1.81 mmol --.

Column 50,
Line 26, reads as "gallons remainsb" and should read as -- gallons remain --.

UNITED STATES PATENT AND TRADEMARK OFFICE
CERTIFICATE OF CORRECTION

PATENT NO.    : 5,977,139
DATED         : November 2, 1999
INVENTOR(S)   : Timothy P. Burkholder, George D. Maynard and Elizabeth M. Kudlacz It is certified that error appears in the above-identified patent and that said Letters Patent is hereby corrected as shown below:

Column 51,
Line 29, reads as "bathe" and should read as -- bath, --.
Line 36, reads as "gels" and should read as -- gel, --.

Column 52,
Line 2, reads as "peridin" and should read as -- piperidin --.
Line 29, reads as "(15 L)" and should read as -- (1.5 L) --.
Line 47, reads as "waters" and should read as -- water, --.

Column 53,
Line 5, reads as "to gives" and should read as -- water, --.
Line 6, reads as "gels" and should read as -- gel, --.
Line 17, reads as "filters" and should read as -- filter, --.

Column 55,
Line 38, reads as "filters" and should read as -- filter, --.

Column 56,
Line 67, reads as "(10 g," and should read as --(1.0 g,--.

Column 57,
Line 67, reads as "filters" and should read as -- filter, --.

Column 58,
Line 23, reads as "-1- carboxamido)" and should read as -- -1-yl)carboxamido --.
Line 31, reads as "5 hour" and should read as -- 5 hours --.
Line 58, reads as "filters" and should read as -- filter, --.
Line 63, reads as "gels" and should read as -- gel, --.

Column 59,
Line 4, reads as "filters" and should read as -- filter, --.
Line 5, reads as "methdxy" and should read as -- methoxy --.

Column 60,
Line 4, reads as "temperatures" and should read as -- temperature. --.
Line 25, reads as "compounds" and should read as -- compound: --.
Line 47, reads as "filters" and should read as -- filter, --.
Line 50, reads as "gels" and should read as -- gel, --.
Line 65, reads as "1 hours" and should read as -- 1 hour, --.
Line 66, reads as "residues" and should read as -- residue. --.

UNITED STATES PATENT AND TRADEMARK OFFICE
CERTIFICATE OF CORRECTION

PATENT NO.  : 5,977,139
DATED       : November 2, 1999
INVENTOR(S) : Timothy P. Burkholder, George D. Maynard and Elizabeth M. Kudlacz It is certified that error appears in the above-identified patent and that said Letters Patent is hereby corrected as shown below:

Column 61,
Line 33, reads as "waters stirs" and should read as -- water, stir, --.
Line 34, reads as "residues" and should read as -- residue. --.

Column 62,
Line 35, reads as "15%" and should read as -- 1.5% --.

Column 63,
Line 6, reads as "1-3." and should read as -- -1(3, --.
Line 7, reads as "carboxymethyi" and should read as -- carboxymethyl --.
Line 8, reads as "dichlorophenyipyrrolidine" and should read as -- dichlorophenyl) pyrrolidine --.

Column 65,
Line 18, reads as "(110 g," and should read as -- (1.10 g, --.
Line 50, reads as "1716.0-179.0ºC" and should read as -- 176.0-179.0ºC --.
Line 63, reads as "solids" and should read as -- solid. --.

Column 66,
Lines 21 and 22, reads as "5 mL/minute" and should read as -- 1.5 mL/minute --.
Line 66, reads as "a a" and should read as -- a --.

Column 67,
Line 45, reads as "filters" and should read as -- filter, --.
Lines 56 and 57, reads as "After minutes" and should read as -- After 30 minutes --.
Line 59, reads as "completes" and should read as -- complete, --.
Line 61, reads as "waters" and should read as -- water, --.
Line 61, reads as "solutions" and should read as -- solution, --.
Line 62, reads as "filters" and should read as -- filter, --.

Column 68,
Line 62, reads as "invacubo" and should read as -- in vacuo --.

Column 69,
Line 8, reads as "residues" and should read as -- residue. --.
Line 16, reads as "8 hour" and should read as -- 8 hours --.

Column 70,
Line 4, reads as "Prepare be" and should read as -- Prepare by --.

UNITED STATES PATENT AND TRADEMARK OFFICE
CERTIFICATE OF CORRECTION

PATENT NO.    : 5,977,139
DATED         : November 2, 1999
INVENTOR(S)   : Timothy P. Burkholder, George D. Maynard and Elizabeth M. Kudlacz It is certified that error appears in the above-identified patent and that said Letters Patent is hereby corrected as shown below:

Column 74,
Lines 28 and 29, reads as "$C_{42}H_{51}Cl_2N_3)_7$" and should read as -- $C_{42}H_{51}Cl_2N_3O_7$ --.

Column 75,
Line 30, reads as "residues" and should read as -- residue. --.
Line 32, reads as "13 g" and should read as -- 1.3 g --.

Column 76,
Line 36, reads as "(0 g," and should read as -- (1.0 g, --.
Line 38, reads as "temperatures" and should read as -- temperature. --.

Column 77,
Line 13, reads as "filters" and should read as -- filter, --.

Column 79,
Line 40, reads as "etherg" and should read as -- ether, --.

Column 81,
Line 19, reads as "(7.3 gb," and should read as -- (7.3 g, --.
Line 25, reads as "solids" and should read as -- solid, --.
Line 27, reads as "chlorides" and should read as -- chloride, --.
Line 29, reads as "filters" and should read as -- filter, --.

Column 83,
Line 23, reads as "bathe" and should read as -- bath, --.
Line 25, reads as "(15 mL)" and should read as -- (1.5 mL) --.
Line 33, reads as "carboxamidodpiperidine" and should read as -- carboxamido) piperidine ) --.

Column 84,
Line 41, reads as "heazne" and should read as -- hexane --.

Column 85,
Line 43, reads as "compounds" and should read as -- compound: --.
Line 43, reads as "gels" and should read as -- gel, --.
Line 46, reads as "carboethoxyepropl" and should read as -- carboethoxypropyl --.

Column 86,
Line 48, reads as "compounds" and should read as -- compound. --.

UNITED STATES PATENT AND TRADEMARK OFFICE
CERTIFICATE OF CORRECTION

PATENT NO. : 5,977,139
DATED : November 2, 1999
INVENTOR(S) : Timothy P. Burkholder, George D. Maynard and Elizabeth M. Kudlacz It is certified that error appears in the above-identified patent and that said Letters Patent is hereby corrected as shown below:

Column 87,
Line 5, reads as "recrystallize" and should read as -- recrystallize --.
Lines 34 & 35, reads as "ichloromethane" and should read as -- dichloromethane --.
Line 36, read as "i hour" and should read as -- 1 hour --.
Line 40, read as "MgSOA" and should read as -- $MgSO_4$ --.

Column 88,
Line 23, reads as "hexaneo" and should read as -- hexane. --.

Column 89,
Line 29, reads as "1505 mmol)" and should read as -- 15.5 mmol) --.

Column 90,
Line 45, reads as "solids" and should read as -- solid: --.

Column 91,
Line 29, reads as "flaskb" and should read as -- flask --.
Line 34, reads as "residues" and should read as -- residue. --.
Line 38, reads as "compound%" and should read as -- compound: --.
Line 53, reads as "settles" and should read as -- settle, --.

Column 93,
Line 24, reads as "(0.49 g, mmol)" and should read as -- (0.49 g, 1.49 mmol) --.

Column 94,
Line 25, reads as "(5 g)" and should read as -- (1.5 g) --.

Column 95,
Lines 3 and 4, reads as "-1-3,4,5-" and should read as -- -1-(3,4,5- --.
Line 8, reads as "(1.4 g)to" and should read as -- (1.4 g) to --.
Line 12, reads as "(3g4," and should read as -- (3,4, --.
Line 26, reads as "-1-yldcarbo" and should read as -- -1-yl)carbo --.
Line 36, reads as "(s, 9 H)g" and should read as -- (s, 9 H), --

Column 96,
Line 6, reads as "(13 g)" and should read as -- (1.3 g) --.
Line 35, reads as "temperature After" and should read as -- temperature. After --.

Column 97,
Line 67, reads as "$MgSO_4$a" and should read as -- $MgSO_4$, --.

UNITED STATES PATENT AND TRADEMARK OFFICE
CERTIFICATE OF CORRECTION

PATENT NO.     : 5,977,139
DATED          : November 2, 1999
INVENTOR(S)    : Timothy P. Burkholder, George D. Maynard and Elizabeth M. Kudlacz It is certified that error appears in the above-identified patent and that said Letters Patent is hereby corrected as shown below:

Column 98,
Line 47, reads as "dichloromethane4%" and should read as -- dichloromethane, 4% --.

Column 101,
Line 55, reads as "(H + 1)$^+$" and should read as -- (M+1)$^+$ --.
Line 59, reads as "sequenceb" and should read as -- sequence, --.

Column 102,
Line 30, reads as "manifestations" and should read as -- manifestation(s). --.

Column 103,
Line 2, reads as "amountb" and should read as -- amount --.
Line 34, reads as "oraly" and should read as -- oral --.
Line 51, reads as "chlorides" and should read as -- chloride, --.

Column 105,
Line 51, reads as "chlorides" and should read as -- chloride, --.

Column 106,
Lines 29 and 31, reads as "vortexes" and should read as -- vortexed --.

Column 107,
Line 4, reads as "post capillary" and should read as -- postcapillary --.
Line 26, reads as "compoundes" and should read as -- compound's --.
Line 45, reads as "form 1-30" and should read as -- from 1-30 --.

Column 108,
Line 32, reads as "timeb." and should read as -- time --.

Column 109,
Line 21, reads as "N-$(CH_2)_n$" and should read as -- N- $G_2$-$(CH_2)_n$ --.

UNITED STATES PATENT AND TRADEMARK OFFICE
CERTIFICATE OF CORRECTION

PATENT NO. : 5,977,139
DATED : November 2, 1999
INVENTOR(S) : Timothy P. Burkholder, George D. Maynard and Elizabeth M. Kudlacz It is certified that error appears in the above-identified patent and that said Letters Patent is hereby corrected as shown below:

<u>Column 113,</u>
Line 24, reads as "carboethoxyepropl" and should read as -- carboethoxypropyl --.

Signed and Sealed this

Fourteenth Day of September, 2004

JON W. DUDAS
*Director of the United States Patent and Trademark Office*